(12) United States Patent
Labrie

(10) Patent No.: US 8,957,054 B2
(45) Date of Patent: *Feb. 17, 2015

(54) PHARMACEUTICAL COMPOSITIONS

(75) Inventor: Fernand Labrie, Quebec (CA)

(73) Assignee: Endorecherche, Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,407

(22) Filed: Jul. 9, 2012

(65) Prior Publication Data

US 2012/0283230 A1 Nov. 8, 2012

Related U.S. Application Data

(62) Division of application No. 12/221,847, filed on Aug. 7, 2008, now Pat. No. 8,268,806.

(60) Provisional application No. 60/964,270, filed on Aug. 10, 2007, provisional application No. 60/964,673, filed on Aug. 13, 2007.

(51) Int. Cl.
*A61K 31/56* (2006.01)
*A61K 9/00* (2006.01)
(Continued)

(52) U.S. Cl.
CPC ............. *A61K 31/453* (2013.01); *A61K 9/0034* (2013.01); *A61K 9/0014* (2013.01); *A61K 31/56* (2013.01); *A61K 31/5685* (2013.01)
USPC ........................................................ 514/182

(58) Field of Classification Search
USPC ........................................................ 514/182
See application file for complete search history.

(56) References Cited

U.S. PATENT DOCUMENTS

| 4,789,669 A | 12/1988 | Sugimoto et al. ............. 514/178 |
| 5,246,704 A | 9/1993 | Sakaguchi et al. ............ 424/433 |

(Continued)

FOREIGN PATENT DOCUMENTS

| CA | 1320132 | 7/1993 |
| CA | 2154161 | 8/1994 |

(Continued)

OTHER PUBLICATIONS

International Search Report and Written Opinion dated Oct. 24, 2008, issued in corresponding PCT International Application No. PCT/CA2008/001444.

(Continued)

*Primary Examiner* — San-Ming Hui
(74) *Attorney, Agent, or Firm* — Ostrolenk Faber LLP

(57) ABSTRACT

Novel methods for treating or reducing the likelihood of acquiring symptoms or diseases due to the menopause, in postmenopausal women, particularly osteoporosis, vaginal atrophy and dryness, hypogonadism, diminished libido, skin atrophy, connective tissue disease, urinary incontinence, breast, endometrial, ovarian and uterine cancers, hot flashes, loss of muscle mass, insulin resistance, fatigue, loss of energy, aging, physical symptoms of menopause, in susceptible warm-blooded animals including humans involving administration of a sex steroid precursor are disclosed. Said method comprising novel ways of administering and dosing dehydroepiandrosterone (DHEA) in order to take advantage of positive androgenic effects in the vaginal layers lamina propia and/or the layer muscularis, without undesirably causing systemic estrogenic effects in order to avoid the risk of breast and uterine cancer. Pharmaceutical compositions for delivery of active ingredient(s) useful to the invention are also disclosed.

28 Claims, 31 Drawing Sheets

(51) Int. Cl.
*A61K 31/5685* (2006.01)
*A61K 31/453* (2006.01)

(56) References Cited

U.S. PATENT DOCUMENTS

| | | | |
|---|---|---|---|
| 5,407,684 A | 4/1995 | Loria et al. | 424/442 |
| 5,629,303 A | 5/1997 | Labrie et al. | 514/169 |
| 5,728,688 A * | 3/1998 | Labrie | 514/178 |
| 5,824,671 A | 10/1998 | Labrie | 514/178 |
| 5,834,451 A | 11/1998 | Ohsawa | 514/177 |
| 5,840,735 A | 11/1998 | Labrie et al. | 514/320 |
| 6,007,824 A | 12/1999 | Druckett et al. | 424/195.1 |
| 6,013,665 A | 1/2000 | DeMichele et al. | 514/458 |
| 6,087,351 A | 7/2000 | Nyce | 514/178 |
| 6,087,362 A | 7/2000 | El-Rashidy | 514/253 |
| 6,294,550 B1 | 9/2001 | Place et al. | 514/302 |
| 6,340,480 B1 | 1/2002 | Druckett et al. | 424/728 |
| 6,569,463 B2 | 5/2003 | Patel et al. | 424/497 |
| 6,583,129 B1 | 6/2003 | Mazer et al. | 514/167 |
| 6,740,327 B2 | 5/2004 | Yu et al. | 424/401 |
| 6,824,786 B2 | 11/2004 | Yu et al. | 424/401 |
| 6,923,988 B2 | 8/2005 | Patel et al. | 424/489 |
| 7,045,513 B1 | 5/2006 | Parasrampuria et al. | 514/170 |
| 7,226,910 B2 | 6/2007 | Wilson et al. | 514/12 |
| 8,268,806 B2 | 9/2012 | Labrie | 514/182 |
| 2002/0013304 A1 | 1/2002 | Wilson et al. | 514/177 |
| 2002/0022052 A1 | 2/2002 | Dransfield | 424/449 |
| 2002/0032160 A1 | 3/2002 | Nyce | 514/26 |
| 2002/0099003 A1 | 7/2002 | Wilson et al. | 514/2 |
| 2002/0107230 A1 | 8/2002 | Waldon et al. | 514/171 |
| 2002/0119936 A1 | 8/2002 | Nyce | 514/26 |
| 2002/0128276 A1 | 9/2002 | Day et al. | 514/256 |
| 2002/0165429 A1 | 11/2002 | Thompson | 600/38 |
| 2002/0198179 A1 | 12/2002 | Labrie | |
| 2003/0004145 A1 | 1/2003 | Leonard | 514/170 |
| 2003/0022875 A1 | 1/2003 | Wilson et al. | 514/171 |
| 2003/0125319 A1 | 7/2003 | Day et al. | 514/217.06 |
| 2003/0138434 A1 | 7/2003 | Campbell et al. | 424/184.1 |
| 2003/0181353 A1 | 9/2003 | Nyce | 514/1 |
| 2003/0216329 A1 | 11/2003 | Robinson et al. | 514/26 |
| 2004/0014761 A1 | 1/2004 | Place et al. | 514/247 |
| 2004/0033963 A1 | 2/2004 | Yu et al. | 514/23 |
| 2004/0044080 A1 | 3/2004 | Place et al. | 514/573 |
| 2004/0082522 A1 | 4/2004 | Nyce | 514/26 |
| 2004/0092583 A1 | 5/2004 | Shanahan-Prendergast | 514/469 |
| 2004/0157812 A1 | 8/2004 | Labrie | 514/177 |
| 2004/0180854 A1 | 9/2004 | Yu et al. | 514/54 |
| 2004/0198706 A1 | 10/2004 | Carrara et al. | 514/169 |
| 2004/0219123 A1 | 11/2004 | Astruc et al. | 424/70.12 |
| 2005/0020552 A1 | 1/2005 | Aschkenasy et al. | 514/171 |
| 2005/0070487 A1 | 3/2005 | Nyce | 514/26 |
| 2005/0070516 A1 | 3/2005 | Wilson et al. | 514/177 |
| 2005/0118272 A1 | 6/2005 | Besse et al. | 424/489 |
| 2005/0181057 A1* | 8/2005 | Rosenberg et al. | 424/488 |
| 2005/0215592 A1 | 9/2005 | Day et al. | 514/319 |
| 2005/0245494 A1 | 11/2005 | Thompson et al. | 514/171 |
| 2006/0018937 A1 | 1/2006 | Friedman et al. | 424/401 |
| 2006/0252734 A1 | 11/2006 | Woodward | 514/170 |
| 2006/0276442 A1 | 12/2006 | Woodward | 514/177 |
| 2007/0021360 A1 | 1/2007 | Nyce | 514/44 |
| 2007/0042060 A1 | 2/2007 | Thompson | 424/742 |
| 2007/0253941 A1 | 11/2007 | Naidu | 424/94.1 |
| 2007/0270394 A1 | 11/2007 | El-Alfy et al. | 514/178 |
| 2008/0090772 A1 | 4/2008 | Yu et al. | 514/25 |
| 2008/0119445 A1 | 5/2008 | Woodward | 514/177 |
| 2008/0145418 A1 | 6/2008 | Zeligs | 424/451 |
| 2008/0206161 A1 | 8/2008 | Tamarkin et al. | 424/45 |

FOREIGN PATENT DOCUMENTS

| | | |
|---|---|---|
| CA | 2334577 | 12/1999 |
| CA | 2515426 | 9/2004 |
| CA | 2584524 | 4/2006 |
| EP | 0 802 183 A1 | 10/1997 |
| EP | 1199069 A2 | 4/2002 |
| EP | 1623712 A2 | 2/2006 |
| JP | 10036347 | 2/1998 |
| JP | 2002-179593 | 6/2002 |
| JP | 2002-517433 | 6/2002 |
| JP | 2003-212793 | 7/2003 |
| JP | 2003-520817 | 7/2003 |
| JP | 2003-527304 | 9/2003 |
| RU | 2004106024 | 4/2005 |
| WO | WO 90/10462 | 9/1990 |
| WO | WO 91/00731 | 1/1991 |
| WO | WO 91/00733 | 1/1991 |
| WO | WO 93/00070 | 1/1993 |
| WO | WO 94/16709 | 1/1994 |
| WO | WO 96/26201 | 8/1996 |
| WO | WO 97/25034 | 7/1997 |
| WO | WO 97/25035 | 7/1997 |
| WO | WO 97/25036 | 7/1997 |
| WO | WO 97/25037 | 7/1997 |
| WO | WO 97/25038 | 7/1997 |
| WO | WO 99/21562 | 5/1999 |
| WO | WO 99/63973 | 12/1999 |
| WO | WO 99/63974 | 12/1999 |
| WO | WO 00/02573 | 1/2000 |
| WO | WO 01/01969 A2 | 1/2001 |
| WO | WO 01/54699 A1 | 8/2001 |
| WO | WO 03/011243 | 2/2003 |
| WO | WO 2004/037262 A2 | 5/2004 |
| WO | WO 2005/066194 A1 | 7/2005 |
| WO | WO 2006/042409 A1 | 4/2006 |
| WO | WO 2006/047859 A1 | 5/2006 |
| WO | WO 2006/133567 A1 | 12/2006 |
| WO | WO 2009/021323 | 2/2009 |

OTHER PUBLICATIONS

International Preliminary Examination Report on Patentability dated Nov. 26, 2009 issued in corresponding International Application No. PCT/CA2008/001444.

Allen, Loyd V Jr, Worthen Dennis B, and Mink Bill, Suppository bases and their characteristics, In Suppositories, Chapter 3 pp. 27-49, Published by the Pharmaceutical Press, London, UK, 2008.

Archer, D. F. (2007). Drospirenone-containing hormone therapy for postmenopausal women. Perspective on current data, J Reprod Med 52(2 Suppl): 159-64.

Ayton, R. A., G. M. Darling, et al. (1996), A comparative study of safety and efficacy of continuous low dose oestradiol released from a vaginal ring compared with conjugated equine oestrogen vaginal cream in the treatment of postmenopausal urogenital atrophy, Br J Obstet Gynaecol,103(4): 351-8.

Bachmann, G., R. A. Lobo, et al. (2008), Efficacy of low-dose estradiol vaginal tablets in the treatment of atrophic vaginitis: a randomized controlled trial, Obstet Gynecol_111(1): 67-76.

Bachmann, G. A:, M. Notelovitz, et al. (1992), Long-term non-hormonal treatment of vagina dryness, J Clin Pract Sex 8.

Baker, V. L. and R. B. Jaffe (1996), Clinical uses of antiestrogens,Obstet Gynecol Surv 51: 45-59.

E.E. Baulieu, G. Thomas, S. Legrain, N. LaWou, M. Roger, B. Debuire, V. Faucounau, L. Girard, M.P. Hervy, F. Latour, M.e. Leaud, A. Mokrane, H. Pitti-Ferrandi, C. Trivalle, O. de Lacharriere, S. Nouveau, B. Rakoto-Arison, J.e. Souberbielle, J. Raison,Y. Le Bouc, A. Raynaud, X. Girerd and F. Forette, Dehydroepiandrosterone (DHEA), DHEA sulfate, and aging: contribution of the DHEAge Study to a sociobiomedical issue, *Proc. Natl. Acad. Sci. U.S.A.* 97 (2000), pp. 4279-4284.

Baxendale, P. M., M. J. Reed, et al. (1981), Inability of human endometrium or myometrium to aromatize androstenedione, *J. Steroid Biochem* 14(3): 305-6.

Belanger, B. Candas, A. Dupont, L. Cusan, P. Diamond, J.L. Gomez and F. Labrie, Changes in serum concentrations of conjugated and unconjugated steroids in 40- to 80 year-old men, *J. Clin. Endocrinol. Metab.* 79 (1994), pp. 1086-1090.

Belanger, G. Pelletier, F. Labrie, O. Barbier and S. Chouinard, Inactivation of androgens by UDP-glucuronosyltransferase enzymes in humans, *Trends Endocrinol. Metab.* 14 (2003), pp. 473-479.

(56) References Cited

OTHER PUBLICATIONS

Beral, V. (2003), Breast cancer and hormone-replacement therapy in the Million Women Study, Lancet 362(9382): 419-27.

Beral, V., D. Bull, et al. (2005) Endometrial cancer and hormone-replacement therapy in the Million Women Study, Lancet 365(9470): 1543-51.

Berger, L., M. EI-Alfy, et al. (2005), Effects of dehydroepiandrosterone Premarin and Acolbifene on histomorphology and sex steroid receptors in the rat vagina, J Steroid Biochem Mol BioI 96(2): 201-15.

Bulun, S. E., Z. Lin, et al. (2005), Regulation of aromatase expression in estrogen-responsive breast and uterine disease: from bench to treatment.Pharmacol Rev 57(3):359-83.

J.E. Buster, P.R Casson, A.B. Straughn, D. Dale, E.S. Umstot, N. Chiamori and G.E. Abraham, Postmenopausal steroid replacement with micronized dehydroepiandrosterone: preliminary oral bioavailability and dose proportionalitystudies, Am. J. Obstet. Gynecol., 166 (1992), pp. 1163-1168 discussion 1168-1170. D.L.

Chlebowski, R T., S. L. Hendrix, et al. (2003), Influence of estrogen plus progestin on breast cancer and mammography in healthy postmenopausal women: the Women's Health Initiative Randomized Trial, Jama 289(24): 3243-53.

Coleman, E.H. Leiter and RW. Schwizer, Therapeutic effects of dehydroepiandrosterone (DHEA) in diabetic mice, Diabetes 31 (1982), pp. 830-833.

Colditz, G. A., K. M. Egn, et al. (1993), Hormone replacement therapy and riks of breast cancer: results from epidemiologic studies, Am. J. Obstet. Gynecol. 168: 1473-1480.

Colditz G. A., S. E. Hankinson, et al. (1995), The use of estrogens and progestins and the risk of breast cancer in postmenopausal women, N. Engl. J. Med. 332: 1589-1593.

Collaborative Group on Hormonal Factors in Breast Cancer (1997), Breast cancer and hormone replacement therapy: collaborative reanalysis of data from 51 epidemiological studies of 52,705 women with breast cancer and 108,411 women without breast cancer, .Lancet 350(9084): 1047-59.

Corrao, G., A. Zambon, et al. (2008), Menopause hormone replacement therapy and cancer risk: an Italian record linkage investigation, Ann Oncol., 19(1): 150-5.

Coughlin, S. S., A. Giustozzi, et al. (2000), A meta-analysis of estrogen replacement therapy and risk of epithelial ovarian cancer, J Clin Epidemiol 53(4): 367-75.

Deutsch, S., R. Ossowski, et al. (1981), Comparison between degree of systemic absorption of vaginally and orally administered estrogens at different dose levels in postmenopausal women, Am J Obstet Gyneco., 39(8): 967-8.

Dew, J. E., B. G. Wren, et al. (2003), A cohort study of topical vaginal estrogen therapy in women previously treated for breast cancer, Climacteric 6(1): 45-52.

P. Diamond, 1. Cusan, J.L. Gomez, A. Belanger and F. Labrie Metabolic effects of 12-month percutaneous DHEA replacement therapy in postmenopausal women, J. Endocrinol., 150 (1996), pp. 543-S50.

Dugal, R., K. Hesla, et al. (2000), Comparison of usefulness of estradiol vaginal tablets and estriol vagitories for treatment of vaginal atrophy, Acta Obstet Gynecol Scand 79(4): 293-7.

Englund, D. E. and E. D. Johansson (1978), Plasma levels of oestrone, oestradiol and gonadotrophins in postmenopausal women after oral and vaginal administration of conjugated equine oestrogens (Premarin), Br J Obstet Gynaecol., 85(12): 957-64.

Fallowfield, L., D. Cella, et al. (2004), Quality of life of postmenopausal women in the Arimidex, Tamoxifen, Alone or in Combination (ATAC) Adjuvant Breast Cancer Trial.J Clin Oncol, 22(21): 4261-71.

Feeley, K. M. and M. Wells (2001), Hormone replacement therapy and the endometrium, J Clin Pathol54(6): 435-40.

Furuhjelm, M., E. Karlgren, et al. (1980), Intravaginal administration of conjugated estrogens in premenopausal and postmenopausal women, .Int J Gynaecol Obstet, 17(4): 335-9.

Galhardo C. L., J. M. Soares, Jr., et al. (2006), Estrogen effects on the vaginal pH, flora and cytology in late postmenopause after a long period without hormone therapy, Clin Exp Obstet Gyneco133(2): 85-9.

Gambrell, R. D., Jr., F. M. Massey, et al. (1980), Use of the progestogen challenge test to reduce the risk of endometrial cancer, Obstet Gynecol, 55(6): 732-8.

Garg, P. P., K. Kerlikowske, et al. (1998), Hormone replacement therapy and the risk of epithelial ovarian carcinoma: a meta-analysis, Obstet Gynecol, 92(3): 472-9.

Grady, D., T. Gebretsadik, et al. (1995), Hormone replacement therapy and endometrial cancer risk: a meta-analysis, Obstet Gynecol, 85(2): 304-13.

Gupta, P., B. Ozel, et al. (2008), The effect of transdermal and vaginal estrogen therapy on markers of postmenopausal estrogen status, Menopause 15(1):94-7.

Holmberg, L. and H. Anderson (2004), HABITS (hormonal replacement therapy after breast cancer—is it safe?), a randomised comparison: trial stopped, Lancet 363(9407): 453-5.

Holmberg, L., O. E. Iversen, et al. (2008), Increased risk of recurrence after hormone replacement therapy in breast cancer survivors, J Natl Cancer Inst 100(7): 475-82.

Holmgren, P. A., M. Lindskog, et al. (1989), Vaginal rings for continuous low-dose release of oestradiol in the treatment of urogenital atrophy, Maturitas 11(1): 55-63.

Hulley, S. B. (2002), Noncardiovascular disease outcomes during 6.8 years of hormone therapy: Heart and estrogen/progestin replacement study follow-up (HERS II), JAMA 288: 58-66.

Jick, S. S., A. M. Walker, et al. (1993), Estrogens, progesterone, and endometrial cancer, Epidemiology 4(1):20-4.

C.C. Johnston Jr., S.L. Hui, RM. Witt, R Appledorn, RS. Baker and C. Longcope, Early menopausal changes in bone mass and sex steroids, J. Clin. Endocrinol. Metab. 61 (1985), pp. 905-911.

D.W. Hum, A. Belanger, E. Levesque O. Barbier, M. Beaulieu, C. Albert, M. Vallee, C. Guillemette, A. Tchernof, D. Turgeon and S. Dubois, Characterization of UDP-glucuronosyltransferases active on steroid hormones, J. Steroid Biochem. Mol. BioI. 69 (1999), pp. 413-423.

H. Kawano, H.Yasue, A. Kitagawa, N. Hirai, T. Yoshida, H. Soejima, S. Miyamoto, M. Nakano and H.Ogawa, Dehydroepiandrosterone supplementation improves endothelial function and insulin sensitivity in men, J. Clin. Endocrinol. Metab. 88 (2003), pp. 3190-3195.

Kendall, A., M. Dowsett, et al. (2006), Caution: Vaginal estradiol appears to be contraindicated in postmenopausal women on adjuvant aromatase inhibitors, Ann Oncol 17(4): 554-7.

Kvorning, J.D.N. and H.K. Jensen (1986), Pharmaceutical development of lose-dose estradiol vagitories, International Workshop, Copenhagen.

Labrie, C., A. Belanger, et al. (1988), Androgenic activity of dehydroepiandrosterone and androstenedione in the rat ventral prostate, Endocrinology, 123: 1412-1417.

Labrie, F. (1991), Intracrinology.Mol. Cell. Endocrinol. 78: C113-C118.

F. Labrie, Future perspectives of SERMs used alone and in combination with DHEA, Endocr. Relaf. Cancer 13 (2006), pp. 335-355.

Labrie, F. (2007), Drug Insight: breast cancer prevention and tissue-targeted hormone replacement therapy, Nature Clinical Practice, Endocrinology & Metabolism, 3(8): 584593.

F. Labrie, A. Belanger, J. Simard, V. Luu-The and C. Labrie, DHEA and peripheral androgen and estrogen formation: intracrinology, Ann. N.Y. Acad. Sci. 774 (1995), pp. 16-28.

Labrie, F., A. Belanger, et al. (2006), Androgen glucuronides, instead of testosterone, as the new markers of androgenic activity in women, Journal Ster Biochem & Mol Biol, 99:182-188.

Labrie, F., A. Belanger, et al. (2005), GnRH agonists in the treatment of prostate cancer, Endocrine Reviews 26(3): 361-379.

Labrie, F., A. Belanger, et al. (1997), Marked decline in serum concentrations of adrenaf C19 sex steroid precursors and conjugated androgen metabolites during aging, J. Clin Endocrinol Metab 82: 2396-2402.

Labrie, F., A. Belanger, et al. (2007), Bioavailability and metabolism of oral and percutaneous dehydroepiandrosterone in postmenopausal women, J Steroid Biochem Mol Biol, 107(1-2): 57-69.

(56) References Cited

OTHER PUBLICATIONS

Labrie, F., A. Belanger, et al. (2007), Metabolism of DHEA in postmenopausal women following percutaneous administration, J Steroid Biochem Mol Bio., 103(2):178-88.

Labrie, F., L. Cusan, et al. (2008), Effect of Intravaginal DHEA on Serum DHEA and Eleven of its Metabolites in Postmenopausal Women, Journal Ster Biochem & Mol Biol: In press.

Labrie, F., L. Cusan, et al. (2008), Effect of One-Week Treatment with Vaginal Estrogen Preparations on Serum Estrogen Levels in Postmenopausal Women, Menopause In press.

Labrie, F., L. Cusan, et al. (2008), Changes in serum DHEA and eleven of its metabolites during 12-month percutaneous administration of DHEA, J Steroid Biochem Mol Biol, 110(1-2): 1-9.

Labrie, F., P. Diamond, et al. (1997), Effect of 12-month dehydroepiandrosterone replacement therapy on bone, vagina, and endometrium in postmenopausal women, J Clin Endocrinol Metab, 82(10): 3498-505.

Labrie, F., A. Dupont, et al. (1985), Complete androgen blockade for the treatment of prostate cancer. Important Advances in Oncology, V. T. de Vita, S. Hellman and S. A. Rosenberg. Philadelphia, J.B. Lippincott: 193-217.

F. Labrie, V. Luu-The, S.X. Lin, C. Labrie, J. Simard, R. Breton and A. Belanger, The key role of 17β-HSDs in sex steroid biology, Steroids, 62 (1997), pp. 148-158.

Labrie, V. Luu-The, S.-X. Lin, J. Simard, C. Labrie, M. El-Alfy, G. Pelletier and A.Belanger, Intracrinology: role of the family of 17β-hydroxysteroid dehydrogenases in human physiology and disease, J. Mol. Endocrinol. 25 (2000), pp. 1-16.

Labrie, F., V. Luu-The, et al. (2005), Is DHEA a hormone? Starling Review.J Endocrinol, 187: 169-196.

Labrie, F., V. Luu-The, et al. (2003), Endocrine and intracrine sources of androgens in women: inhibition of breast cancer and other roles of androgens and their precursor dehydroepiandrosterone, Endocrine Reviews 24(2): 152-182.

Labrie, F., V. Luu- The, et al. (2006), Dehydroepiandrosterone (DHEA) is an anabolic steroid like dihydrotestosterone (DHT), the most potent natural androgen, and tetrahydrogestrinone (THG), J Steroid Biochem Mol Biol., 100(1-3): 52-8.

F. Labrie, J. Simard, V. Luu-The, A. Belanger, G. Pelletier, Y. Morel, F. Mebarki, R. Sanchez, F. Durocher, C. Turgeon, Y. Labrie, E. Rheaume, c. Labrie and Y. Lachance, The 3β-hydroxysteroid dehydrogenase/isomerase gene family: lessons from type II 3β-HSD congenital deficiency. In: V. Hansson, F.O. Levy and K. Tasken, Editors, Signal Transduction in Testicular Cells. Ernst Schering Research Foundation Workshop, vol Suppl. 2, Springer-Verlag, Berlin (1996), pp. 185-218.

Labrie, J. Simard, V. Luu-The, A. Belanger and G. Pelletier, Structure, function and tissue-specific gene expression of 3β-hydroxysteroid dehydrogenase/5-ene-4-ene isomerase enzymes in classical and peripheral intracrine steroidogenic tissues, J. Steroid Biochem. Mol. Biol. 43 (1992), pp. 805-826.

F. Labrie, R. Poulin, J. Simard, V. Luu-The, C. Labrie and A. Belanger, Androgens, DHEA and breast cancer, In: T. Gelfand, Editor, Androgens and Reproductive Aging, Taylor and Francis, Oxsfordshire, UK (2006), pp. 115-135.

Labrie, Y. Sugimoto, V. Luu-The, J. Simard, Y. Lachance, D. Bachvarov, G. Leblanc, F. Durocher and N. Paquet, Structure of human type II 5α-reductase, Endocrinology, 131 (1992), pp. 1571-1573.

Y. Labrie, F. Durocher, Y. Lachance C. Turgeon, J. Simard, C. Labrie and F. Labrie, The human type II 17β-hydroxysteroid dehydrogenase gene encodes two alternatively-spliced messenger RNA species, DNA Cell Biol. 14 (1995), pp. 849-861.

Lacey, J. V., P. J. Mink, et al. (2002), Menopausal hormone replacement therapy and risk of ovarian cancer, JAMA 288: 334-341.

Li, L., S. J. Plummer, et al. (2008), A common 8q24 variant and the risk of colon cancer: a population-based case-control study, Cancer Epidemiol Biomarkers Prev 17(2): 339-42.

C.H. Liu G.A. Laughlin, D.G. Fischer and S.S. Yen, Marked attenuation of ultradian and circadian rhythms of dehydroepiandrosterone in postmenopausal women: evidence for a reduced 17,20-desmolase enzymatic activity, ]. Clin. Endocrinol. Metab., 71 (1990), pp. 900-906.

Long, C. Y., C. M. Liu, et al. (2006), A randomized comparative study of the effects of oral and topical estrogen therapy on the vaginal vascularization and sexual function in hysterectomized postmenopausal women, Menopause 13(5): 737-43.

V. Luu-The, I. Dufort, N. Paquet, G. Reimnitz and F. Labrie Structural characterization and expression of the human dehydroepiandrosterone sulfotransferase gene, DNA Cell. Biol. 14 (1995), pp. 511-518.

V. Luu-The, Y. Zhang, D. Poirier and F. Labrie, Characteristics of human types I, 2 and 3 17β-hydroxy, dehydrogenase activities: oxidation-reduction and inhibition, J Steroid: Biochem. Mol. Biol., 55 (1995), pp. 581-558.

Lyytinen, H., E. Pukkala, et al. (2006), Breast cancer risk in postmenopausal women using estrogen-only therapy, Obstet Gyneco1 108(6): 1354-60.

E.G. MacEwen and I.D. Kurzman, Obesity in the dog: role of the adrenal steroid dehydroepiandrosterone (DHEA), J. Nutr. 121 (1991), pp. S51-S55.

Mandel, F. P., F. L. Geola, et al. (1983), Biological effects of various doses of vaginally administered conjugated equirie estrogens in postmenopausal women, J Clin Endocrinol Metab-57(1): 133-9.

Manonai, J., U. Theppisai, et al. (2001), The effect of estradiol vaginal tablet and conjugated estrogen cream on urogenital symptoms in postmenopausal women: a comparative study, J Obstet Gynaecol Res 27(5): 255-60.

Martin, P. L., S. S. Yen, et al. (1979), Systemic absorption and sustained effects of vaginal estrogen creams, Jama, 242(24): 2699-700.

Marx, P., G. Schade, et al. (2004), Low-dose (0.3 mg) synthetic conjugated estrogens A is effective for managing atrophic vaginitis, Maturitas, 47(1): 47-54.

Mattson, L. A., G. Culberg, et al. (1989), Vaginal administration of low dose estradiol-effects on endometrium and vaginal cytology, Maturitas, 11: 217-222.

R.B. Mazess, On aging bone loss, Clin. Orthop. 165 (1982), pp. 239-252.

Meisels, A. (1967), The maturation value, Acta Cyto111: 249.

Mertens, H. J., M. J. Heineman, et al. (1996), Androgen receptor content in human endometrium, Eur J Obstet Gynecol Reprod Biol 70(1): 11-3.

Mettler, L. and P. G. Olsen (1991), Long-term treatment of atrophic vaginitis with low-dose oestradiol vaginal tablets, Maturitas 14(1): 23-31.

C.J. Migeon, A.R. Keller, B. Lawrence and T.H. Shepart II., Dehydroepiandrosterone and androsterone levels in human plasma. Effect of age and sex: day-to-day and diurnal variations, J. Clin. Endocrinol. Metab. 17 (1957), pp. 1051-1062.

A.J. Morales, J-J. Nolan, J.C. Nelson and S.S Yen, Effects of replacement dose of dehydroepiandrosterone in men and women of advancing age, J. Clin. Endocrinol. Metab. 78 (1994), pp. 1360-1367.

Morales, L., P. Neven, et al. (2004), Acute effects of tamoxifen and third-generation aromatase inhibitors on menopausal symptoms of breast cancer patients, Anticancer Drugs 15(8): 753-60.

N.A.M.s. (2007), Position Statement of the North American Menopause Society, Menopause, 14: 357-69.

Nachtigall, L. E. (1995), Clinical trial of the estradiol vaginal ring in the U.S., Maturitas, 22 Suppl: 543-7.

Naessen, T., K. Rodriguez-Macias, et al. (2001), Serum lipid profile improved by ultra-low doses of 17 beta-estradiol in elderly women, J Clin Endocrinol Metab 86(6): 2757-62.

Nelson, H. D., K. K. Vesco, et al. (2006), Nonhormonal therapies for menopausal hot flashes: systematic review and meta-analysis, Jama 295(17): 2057-71.

J.E. Nestler, e.o. Barlascini, J.N. Clore and W.G. Blackard, Dehydroepiandrosterone reduces serum low density lipoprotein levels and body fat but does not alter insulin sensitivity in normal men, J. Clin. Endocrinol. Metab. 66 (1988), pp. 57-61.

Nilsson, K. and G. Heimer (1992), Low-dose oestradiol in the treatment of urogenital oestrogen deficiency—a pharmacokinetic and pharmacodynamic study, Maturitas 15(2): 121-7.

(56) References Cited

OTHER PUBLICATIONS

Notelovitz, M., S. Funk, et al. (2002), Estradiol absorption from vaginal tablets in postmenopausal women, Obstet Gynecol, 99(4): 556-62.

Orentreich, N., J. L. Brind, et al. (1984), Age changes and sex differences in serum dehydroepiandrosterone sulfate concentrations throughout adulthood, J. Clin. Endocrino!. Metab. 59: 551-555.

Pandit, L. and J. G. Ouslander (1997), Postmenopausal vaginal atrophy and atrophic vaginitis, Am J Med Sci 314(4): 228-31.

Persson, 1., H. O. Adami, et al. (1989), Risk of endometrial cancer after treatment with oestrogens alone or in conjunction with progestogens: results of a prospective study, Bmj 298(6667): 147-51.

Ponzone, R., N. Biglia, et al. (2005), Vaginal oestrogen therapy after breast cancer: is it safe?, Eur J Cancer 44(17): 2673-81.

Rigg, L. A., H. Hermann, et al. (1978), Absorption of estrogens from vaginal creams, N Engl J Med 298(4): 195-7.

B.L. Riggs, H.W. Wahner, W.L. Dunn, R.B. Mazess, K.P. Offord and L.J. Melton, Differential changes in bone mineral density of the appendicular and axial skeleton with aging: relationship to spinal osteoporosis, J. Clin. Invest. 67 (1981), pp. 328-335.

Riman, T., P. W. Dickman, et al. (2002), Hormone replacement therapy and the risk of invasive epithelial ovarian cacner in Swedish women, J Natl Cancer Inst 94: 497-504.

Rinaldi,S., H. Dechaud, et al. (2001), Reliability and validity of commercially available, direct radioimmunoassays for measurement of blood androgens and estrogens in postmenopausal women, Cancer Epidemiol Biomarkers Prev, 10(7): 757-65.

Rioux, J. E., C. Devlin, et al. (2000), 17beta-estradiol vaginal tablet versus conjugated equine estrogen vaginal cream to relieve menopausal atrophic vaginitis, Menopause 7(3): 156-61.

Rodriguez, C., A. V. Patel, et al. (2001), Estrogen replacement therapy and ovarian cancer mortality in a large prospective study of US women, JAMA 285: 1460-1465.

Rosenberg, L. V., C. Magnusson, et al. (2006), Menopausal hormone therapy and other breast cancer risk factors in relation to the risk of different histological subtypes of breast cancer: a case-control study, Breast Cancer Res 8(1): R11.

Rossouw, J. E., G. L. Anderson, et al. (2002), Risks and benefits of estrogen plus progestin in healthy postmenopausal women: principal results From the Women's Health Initiative randomized controlled trial, JAMA 288(3): 321-33.

Salminen, H. S., M. E. Saaf, et al. (2007), The effect of transvaginal estradiol on bone in aged women: a randomised controlled trial, Maturitas 57(4): 370-81.

Schiff, I., D. Tulchinsky, et al. (1977), Vaginal absorption of estrone and 17beta-estradiol, Fertil Steril, 28(10):1063-6.

Schmidt, G., S. B. Andersson, et al. (1994) Release of 17-beta-oestradiol from a vaginal ring in postmenopausal women: pharmacokinetic evaluation, Gynecol Obstet Invest 38(4):253-60.

E.D. Schriock, C.K. Buffington, G.D. Hubert, B.R. Kurtz, A.E. Kitabchi, J.E. Buster and J.R. Givens, Divergent correlations of circulating dehydroepiandrosterone sulfate and testosterone with insulin levels and insulin receptor binding, J. Clin. Endocrinol. Metab. 66 (1988), pp. 1329-1331.

Sillero-Arenas, M., M. Delgado-Rodriguez, et al. (1992), Menopausal hormone replacement therapy and breast cancer: a meta-analysis.Obstet. Gynecol., 79: 286-294.

Simon, J. A., K Z. Reape, et al. (2007), Randomized, multicenter, double-blind, placebo-controlled trial to evaluate the efficacy and safety of synthetic conjugated estrogens B for the treatment of vulvovaginal atrophy in healthy postmenopausal women, Fertil Steril. In press.

E.R Simpson Role of aromatase in sex steroid action, J. Mol. Endocrinol., 25 (2000), pp. 149-156.

Simunic, V., 1. Banovic, et al. (2003), Local estrogen treatment in patients with urogenital symptoms, Int J Gynaecol-Obstet 82(2): 187-97.

Smith, D.C., R Prentice, et al. (1975), Association of exogenous estrogen and endometrial carcinoma, N. Engl. J. Med. 293: 1164-1167.

Smith, P., G. Heimer, et al. (1993), Oestradiol-releasing vaginal ring for treatment of postmenopausal urogenital atrophy, Maturitas 16(2): 145-54.

Sourla, A.,M. Flamand, et al. (1998), Effect of dehydroepiandrosterone on vaginal and uterine histomorphology in the rat, J. Steroid Biochem. Mol. Biol., 66(3): 137-149.

Steinber, K.K., S. B. Thacker, et al. (1991), A meta-analysis of the effect of estrogen replacement therapy on the risk of breast cancer, JAMA 265: 1985-1990.

K.K. Steinberg, L.W. Freni- Titulaer, E.G. DePuey, D.T. Miller, D.S. Sgoutas, C.H. Coralli, D.L. Phillips, T.N. Rogers and RV. Clark, Sex steroids and bone density in premenopausal and perimenopausal women, J. Clin. Endocrinol.Metab., 69 (1989), pp. 533-539.

Suckling, J., A. Lethaby, et al. (2006), Local oestrogen for vaginal atrophy in postmenopausal women, Cochrane Database System Rev 18(4): CD001500.

Swanson, M. Lorentzon, L. Vandenput, D. Mellstrom, F. Labrie, A. Rane, J. Jakobsson, C. Ohlsson, Sex Steroid Levels and Cortical Bone Size in Young Men Are Associated with a Uridine Diphosphate Glucuronosyltransferase 2B7 Polymorphism ($H^{268}Y$) The Journal of Clinical Endocrinology & Metabolism, 92(9):3697-3704 (2007).

Tchernof, J.P. Despres, A. Belanger, A. Dupont, D. Prud'homme, S. Moorjani, P.J. Lupien and F. Labrie, Reduced testosterone and adrenal C19 steroid levels in obese men, Metabolism 44 (1995), pp. 513-519.

Turgeon, J.S. Carrier, E. Levesque, D.W. Hum and A. Belanger, Relative enzymatic activity, protein stability, and tissue distribution of human steroid-metabolizing UGT2B subfamily members, Endocrinology 142 (2001), pp. 778-787.

Utian, W. H., D. Shoupe, et al. (2001), Relief of vasomotor symptoms and vaginal atrophy with lower doses of conjugated equine estrogens and medroxyprogesterone acetate, Fertil Steril, 75(6):1065-79.

Vermeulen and L. Verdonck, Radioimmunoassays of 17β-hydroxy-5-androstan-3-one, 4-androstene-3,17-dione, dehydroepiandrosterone, 17β-hydroxyprogesterone and progesterone and its application to human male plasma, J. Steroid Biochem. 7 (1976), pp. 1-10.

D.T. Villareal and J.O. Holloszy, Effect of DHEA on abdominal fat and insulin action in elderly women and men: a randomized controlled trial, JAMA 292 (2004), pp. 2243-2248.

Voigt, L. F., N. S. Weiss, et al. (1991), Progestagen supplementation of exogenous oestrogens and risk of endometrial cancer, Lancet 338(8762): 274-7.

Weisberg, E., R. Ayton, et al. (2005), Endometrial and vaginal effects of low-dose estradiol delivered by vaginal ring or vaginal tablet, Climacteric 8(1): 83-92.

Wied, G. L. (1993), Industrial developments in automated cytology as submitted by their developers, Anal Quant Cytol Histol, 15(5): 358-70.

Wines, N. and E. Willsteed (2001), Menopause and the skin, Australas J Dermatol 42(3): 149-158; quiz 159.

Zang, H., L. Sahlin, et al. (2007), Effects of testosterone treatment on endometrial proliferation in postmenopausal women, J Clin Endocrinol Metab, 92(6): 2169-75.

B. Zumoff, C.W. Strain, L.K. Miller and W. Rosner, Twenty-four-hour mean plasma testosterone concentration declines with age in normal premenopausal women, J. Clin. Endocrinol. Metab. 80 (1995), pp. 1429-1430.

Extended European Search Report dated Oct. 4, 2010 in corresponding European Patent Application No. 08783354.7-2123 / 2185157.

F. Labrie: "Dehydroepiandrosterone (DHEA) as Potential Hormone Replacement Therapy", REF Gynecol Obstet, vol. 8, No. 5, Jan. 1, 2001, pp. 317-322, XP009109498, ISSN: 1244-8168.

Mayo Clinic definition for Vaginal Atrophy (2010), http:/www.mayoclinic.com/health/vaginal-atrophy/DS0070.

Rosenthal, Ronnie Ann; Zenilman, Michael E.; Katlic, Mark R (Editors): Principles and Practice of Geriatric Surgery, pp. 820-821, 2001, Springer, ISBN: 978-0-387-98393-7.

Berman, Jennifer R. et al.: "Effect of Estrogen Withdrawal on Nictic Oxide Synthase Expression and Apoptosis in the Rat Vagina", UROLOGY, vol. 51, No. 4, Apr. 1998, pp. 650-656, ISSN: 0090-4295.

(56) References Cited

OTHER PUBLICATIONS

Opposition against corresponding Ecuadorian Patent Application No. SP 2010-10016, filed by Asociacion de Laboratories Farmaceuticos ("ALAFAR" by its Spanish acronym) (English language translation).
Yamashita, et al., Nippon Yakurigaku Zasshi, (1991) vol. 98, No. 1, pp. 31-39, abstract.
Belayet et al., Human Reprod. (1999) vol. 14, No. 5, pp. 1361-1367.
El Maradny et al., Human Reprod. (1996) vol. 11, No. 5, pp. 1099-1104.
Rossin-Amar, 2000, *Gynecol Ostet. Fertil.*, 28(3): 245-249.
Helzlsouer et al., 1992, *Cancer Res.*, 52(1): 1-4.
Szathmári et al., 1994, *Osteoporos. Int.*, 4(2): 84-88.
Thoman and Weigle, 1989, *Adv. Immunol.*, 46: 221-261.
Casson et al., Delivery of dehydroepiandrosterone to premenopausal women: effects of micronization and nonoral administration. Am. J. Obstet. Gynecol., Feb. 1996, 174(2):649-53.
Labrie et al., "Vaginal Atrophy High internal consistency and efficacy of intravaginal DHEA for vaginal atrophy," Gynecological Endocrinology, Jul. 2010; 26(7): 524-532.
University of Maryland Medical center, "Dehydroepiandrosterone (DHEA)," Internet Article, [online] 2002, pp. 1-9, XP002506423, www.umm.edu/altmed/articles/dehydroepiandroesterone-dhea-000299.htm.
Christine Conrad, "A Woman's Guide to Natural Hormones" (2000) pp. 134-135.
Hardy, Ellen, "Women's Preferences for Vaginal Antimicrobial Contraceptives III" (1998) pp. 245-249.
Pharmasave Health Library—"Be Well Informed About Feminine Health Care".
Pfizer for Professional—CLEOCIN Vaginal Ovules.
Labrie et al., 2009, *Menopause: J. North American Menopause Society*, 16(5): 923-931.
Labrie et al., 2009, *Menopause: J. North American Menopause Society*, 16(5): 907-922.
Gauthier et al., 2008, *J. Med. Chemistry*, 40(14) 2116-2122.
Calvo et al., 2008, *J. Steroid Biochem. Mol. Biol.*, 112: 186-193.
Singh et al., 2000, *Current Med. Chemistry*, 7: 211-247.
Brzezinski et al.,2009, *Menopause: J. North American Menopause Society*, 16(5): 848-850.
Dubin et al., 1985, *Toxicology and Applied Pharmacology*, 78: 458-463.
Krogsgaard-Larsen et al., *Textbook of Drug Design and Dev.*, 154-155.
Dhareshwar et al., *Prodrugs of Alcohols and Phenols*, 3.2: 31-99.
Silverman, 1992, *Academic Press, Inc., The Org Chem of Drug Design and Drug Action*.
Glina et al., "Efficacy and Tolerability of Lodenafil Carbonate for Oral Therapy in Erectile Dysfunction, A Phase II Clinical Trial," J. SEX MED., Nov. 17, 2008, abstract only.
Hatzimouratidis et al. Looking to the future for erectile dysfunction therapies, DRUGS, 2008, 68(2):231-50.
Knudsen and Mahesh, 1975, *Endocrinol.*, 97(2): 4580-468.
Lephart et al., 1989, *Biol. Reprod.*, 40(2): 259-267.
Shao et al., 1950, *J. Biol. Chem.*, 250: 3095-3100.
Poortman et al., 1975, *J. Clin. Endocrinol Metab.* 40(3): 373-379.
Van Doorn et al., 1981, *Endocrinol.*, 108: 1587-1594.
Adams et al., 1981, *Cancer Res.*, 41: 4720-4726.
Poulin and Labrie, 1986, *Cancer Res.*, 46: 4933-4937.
Barrett-Connor et al., 1999, *J. Reprod. Med.*, 44(12): 1012-1020.
Barrett-Connor et al., 1999, *J. Am. Geriatr. Soc.*, 47 (96): 685-691.
Ross et al., 2000, *J. Natl. Cancer Inst.*, 92(4): 328-332.
Rosenberg et al., 1997, *J. Reprod. Med.*, 42(7): 394-404.
Burd et al., 2001, *Curr Women Health Rep.*, 1(3): 202-205.
Lasco et al., 2001, *European Journal of Endocrinology*, 145: 457-461.
Labrie et al., 1999, *J. Steroid Biochem. Mol. Biol.*, 69 (1-6) : 51-84.
Tremblay et al., 1998, *Endocrinology*, 139: 111-118.
Dauvois et al., 1991, *Cancer Res.*, 51: 3131-3135.
Luo et al., 1997, *Endocrinology*, 138: 4435-4444.
Willson et al., 1997, *Endocrinol.*, 138(9): 3901-3911.
Kramer, 1956, *Biometrics*, 12: 307-310.
Notelovitz, 2000, *Menopause*, 7(3): 140-142.
Berman et al., 1999, *Curr. Opin. Urol.*, 9(6): 563-568.
Labrie et al., 1996, *Endocrinol.*, 150: S107-S118.
Emmens and Martin, 1964, Dorfman Ed, Ed Academic Press NY:1.
Labrie et al., 2003, *Endocrinol.*, 144 (11): 4700-4706.
Anderson and Kang, 1975, *Am J anat*, 144(2): 197-207.
Yoshida et al., 1998, *Cancer Lett*, 134(1): 43-51.
Sourla et al., 1998, *Endocrinol.*, 139: 753-764.
Sourla et al., 2000, *J. Endocrinol.*, 166(2): 455-462.
Martel et al., 1998, *J. Endocrinol.*, 157: 433-442.
Martel et al., 2000, *J Steroid Biochem. Mol. Biol.*, 74 (1-2): 45-56.
Munarriz et al., 2003, *J. Urol.* 170 (2 Pt. 2): S40-S44, Discussion S44-S-45.
Simoncini et al., 2002, *Endocrinol.*, 143(6): 2052-2061.
Guay and Jacobson, 2002, *J. Sex Marital Ther.*, 28 Suppl. 1:129-142.
Casson et al., 1997, Obstet. Gynecol., 90(6): 995-998.
Hackenberg et al., *J. Steroid Biochem. Molec. Biol.*, vol. 46, No. 5, 1993, pp. 597-603.
Couillard et al., *Journal of the National Cancer Institute*, vol. 90, No. 10, May 20, 1998, pp. 772-778.
Luo et al., *Breast Cancer Research and Treatment*, 49:1-11, 1998.
Labrie et al., *Steroids*, 63:322-328, 1998.
Bachmann, G. et al.: "Diagnosis and Treatment of Atrophic Vaginitis", American Family Physician, 2000, vol. 61 (10), pp.-3090-3096.
Kim, N.N. et al. "Effects of Ovariectomy and Steroid Hormones on Vaginal Smooth Muscle Contractility", *Int J Impotence Res.*, (2004) 16:43-50.
The SciFinder Search dated Oct. 13, 2009, 32 pages—search refers to derivatives of acolbifene.
Additional Options, http://www.vaginaldiscomfort.com/additional_options.asp , Sep. 22, 2009.
Is Perfume an Irritant? by SweetSpotLabs, http://www.sweetspotlabs.com/isperfumeirritant.shtml , Sep. 22, 2009.
Co-pending U.S. Appl. No. 13/602,503, filed on Sep. 4, 2012 by Fernand Labrie, entitled "Pharmaceutical Compositions".
Co-pending U.S. Appl. No. 13/602,602, filed on Sep. 4, 2012 by Fernand Labrie, entitled "Pharmaceutical Compositions".

\* cited by examiner

Mean Change from Baseline (Day 1)
By Treatment in Most Bothersome Symptom

Mean change (+/− Std error) over time in vaginal color

Mean change (+/− Std error) by treatment in vaginal epithelial integrity

PHARMACEUTICAL COMPOSITIONS

CROSS REFERENCE TO RELATED APPLICATION(S)

The present application is a divisional of U.S. patent application Ser. No. 12/221,847, filed Aug. 7, 2008, in the name of Ferand Labrie entitled "PHARMACEUTICAL COMPOSITIONS" and claims benefit of and priority to U.S. Provisional Application Ser. No. 60/964,270, filed Aug. 10, 2007, and U.S. Provisional Application Ser. No. 60/964,673, filed Aug. 13, 2007, in the name of Fernand Labrie, entitled "DHEA PHARMACEUTICAL", the entire contents of which are hereby incorporated by reference herein.

FIELD OF THE INVENTION

The present invention provides novel ways of administering and dosing dehydroepiandrosterone (DHEA) in order to take advantage of positive androgenic effects (for example in the vaginal layers lamina propia and/or the layer muscularis), without undesirably causing systemic estrogenic effects. In addition to DHEA, other sex steroid precursors may be used (e.g., dehydroepiandrosterone-sulfate, androst-5-ene-3β, 17β-diol, and 4-androstene-3,17-dione).

BACKGROUND OF THE RELATED ART

Many hormone-related therapies are known. For example, many provide the sex steroids estrogen or androgen systemically and/or to target tissue. In addition to direct administration of androgens and/or estrogens, sex steroid precursors that can be converted to estrogen and/or androgen in a given tissue have also been used for many conditions. Both androgens and estrogens can be beneficial in some contexts and detrimental in others. That depends inter alia on the tissue being targeted, the specific needs presented by a patient, and the extent to which non-targeted tissue may be affected. Some therapies, though targeted, can still have undesirable activity elsewhere in the body (e.g. where local administration of the pharmaceutical agent nonetheless results in increased systemic presence of either the pharmaceutical or one of its metabolites. Also, the mechanism of action has not always been fully understood, especially the relative contributions of androgens and estrogens.

SUMMARY OF THE INVENTION

It is therefore an object of the present invention to utilize specific dosages, formulations and modes of administration to better achieve the beneficial effects of sex steroids and to better avoid their undesirable side effects.

In one aspect, the invention provides a method of treating and/or reducing the likelihood of acquiring vaginal diseases or conditions related to hormonal imbalance in postmenopausal women, said method comprising administering a sex steroid precursor selected from the group consisting of dehydroepiandrosterone, dehydroepiandrosterone-sulfate, androst-5-ene-3β,17β-diol, and 4-androsten-3,17-dione to a patient in need of said treatment wherein the said sex steroid precursor is administered at a therapeutic amount which increases the level of circulating androgen metabolites without increasing the level of estradiol above the values found in normal postmenopausal women.

In another aspect, the invention provides a method of treating and/or reducing the likelihood of acquiring symptoms or diseases due to the menopause, in postmenopausal women, said method comprising administering a sex steroid precursor selected from the group consisting of dehydroepiandrosterone, dehydroepiandrosterone-sulfate, androst-5-ene-3β,17β-diol, and 4-androsten-3,17-dione to a patient in need of said treatment wherein the said sex steroid precursor is administered at a therapeutic amount which increases the level of circulating androgen metabolites without increasing the circulating level of estradiol above the values found in normal postmenopausal women in order to avoid the risk of breast and uterine cancer.

In another aspect, the invention provides a method of treating and/or reducing the likelihood of acquiring symptoms or diseases due to the menopause, in postmenopausal women, said method comprising administering a sex steroid precursor selected from the group consisting of dehydroepiandrosterone, dehydroepiandrosterone-sulfate, androst-5-ene-3β,17β-diol, and 4-androsten-3,17-dione to a patient in need of said treatment wherein the said sex steroid precursor is administered at a therapeutic amount which increases the level of circulating androgen metabolites and further comprising administering as part of a combination therapy, a therapeutically effective amount of a Selective Estrogen Receptor Modulator in order to avoid the risk of breast and uterine cancer normally present in postmenauposal women and to prevent bone loss, fat accumulation and diabetes type 2.

In another aspect, the invention provides method of treating vaginal conditions of the layer lamina propia or layer muscularis comprising vaginal administration of DHEA in a daily dose of 3-13 mg.

In another aspect, the invention provides a pharmaceutical composition comprising a sex steroid precursor selected from the group consisting of dehydroepiandrosterone, dehydroepiandrosterone-sulfate, androst-5-ene-3β,17β-diol, and 4-androstene-3,17-dione and further comprising a pharmaceutically acceptable excipient, diluent or carrier selected from the group consisting of triglycerides of saturated fatty acids C12-C18 with varied portions of the corresponding partial glycerides (hard fat, Witepsol), butter, mixed triglycerides of oleic, palmitic, and stearic acids (cocoa butter), partially hydrogenated cottonseed oil (Cotomar), hydrogenated fatty alcohols and esters (Dehydag Base I, Base II or Base III, may also contains glycerides of saturated fatty acids C12-C16), triglycerides from palm, palm kernel, and coconut oils with self-emulsifying glyceryl monostearate and polyoxyl stearate (Fattibase), Hexaride Base 95, higher melting fractions of coconut and palm kernel oil (Hydrokote), Rearranged hydrogenated vegetable oils (S-70-XX95 and S-070-XXA), eutectic mixture of mono-, di-, triglycerides derived from natural vegetable oils (Suppocire), Tegester Triglycerides, Tween 61, triglycerides derived from coconut oil (Wecobee), theobroma oil, semi-synthetic glycerides (Japocire, Ovucire), mixture of tri- di- and monoglycerides of saturated fatty acids (Massa Estarinum) and a combination of the foregoing (see Allen et al. 2008). Any vehicle including liquid in which DHEA and other precursors are soluble covers by this invention.

In another aspect, the invention provides a vaginal suppository comprising 0.25-2.00 percent, more specially 0.5 percent DHEA, by weight relative to the total weight of the suppository, of DHEA, and further comprising a lipophilic excipient. Particularly suitable excipient is witepsol H-15.

By providing the desired androgenic effects without estrogenic systemic effects, systemic side effects of estrogen such as the increased risk of breast and endometrial cancers found with current estrogen-based local and systemic estrogen replacement therapies (Labrie, Cusan et al. Menopause, in press) can be avoided.

In addition to other forms of administering precursors, the invention provides vaginal suppositories and vaginal creams formulated with preferred excipients and preferred concentrations of precursor.

Vaginal administration is preferred because local action may provide the desired androgenic effects on desired vaginal layers at much lower dosages than when otherwise administered. Dosing by other means of administration may also be utilized by altering the foregoing dosages and concentrations for known variation between the methods of administration. The attending clinician should alter dosages appropriately in accordance with individual patient response.

In preferred embodiments, the sex steroid precursor is DHEA.

DETAILED DESCRIPTION OF THE INVENTION

Figure 1:
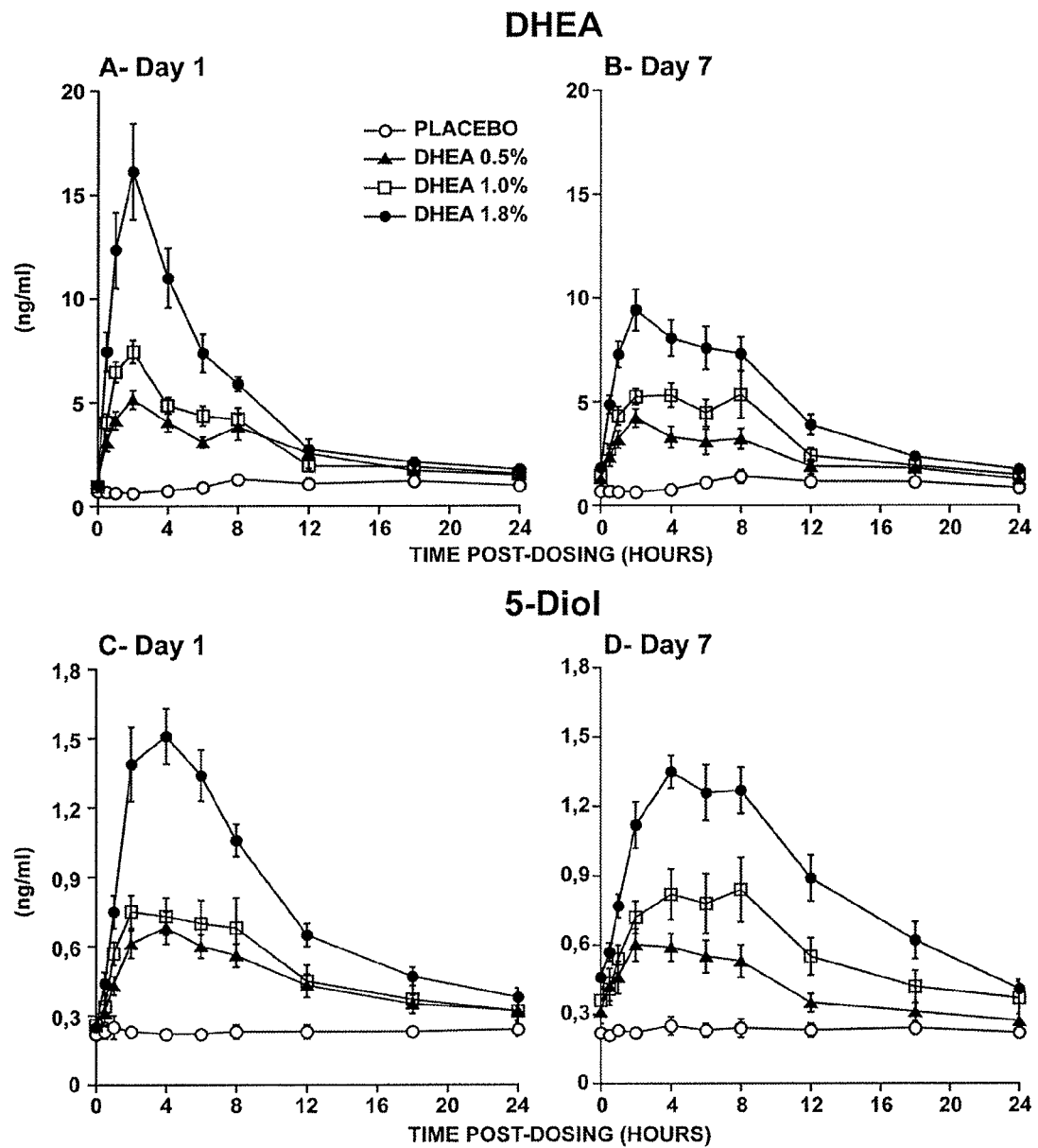
FIG. 1 shows serum Levels of DHEA and 5-Diol on Day 1 or Day 7 in 40-75 Year-Old Postmenopausal Women Following Daily Administration of Vaginal Suppositories Containing 0%, 0.5%, 1.0% or 1.8% of DHEA. Data are expressed as means±SEM (n=9 or 10).

Set Forth below are a list of articles discussed herein in short form citations:

Allen, Loyd V Jr, Worthen Dennis B, and Mink Bill, in Suppositories, Chaper 3 pages 27-49, Published by the Pharmaceutical Press, London, UK, 2008

Archer, D. F. (2007). "Drospirenone-containing hormone therapy for postmenopausal women. Perspective on current data." *J Reprod Med* 52(2 Suppl): 159-64.

Ayton, R. A., G. M. Darling, et al. (1996). "A comparative study of safety and efficacy of continuous low dose oestradiol released from a vaginal ring compared with conjugated equine oestrogen vaginal cream in the treatment of postmenopausal urogenital atrophy." *Br J Obstet Gynaecol* 103(4): 351-8.

Bachmann, G., R. A. Lobo, et al. (2008). "Efficacy of low-dose estradiol vaginal tablets in the treatment of atrophic vaginitis: a randomized controlled trial." *Obstet Gynecol* 111(1): 67-76.

Bachmann, G. A., M. Notelovitz, et al. (1992). "Long-term non-hormonal treatment of vagina dryness." *J Clin Pract Sex* 8.

Baker, V. L. and R. B. Jaffe (1996). "Clinical uses of antiestrogens." *Obstet Gynecol Surv* 51: 45-59.

E. E. Baulieu, G. Thomas, S. Legrain, N. Lahlou, M. Roger, B. Debuire, V. Faucounau, L. Girard, M. P. Hervy, F. Latour, M. C. Leaud, A. Mokrane, H. Pitti-Ferrandi, C. Trivalle, O. de Lacharriere, S, Nouveau, B. Rakoto-Arison, J. C. Souberbielle, J. Raison, Y. Le Bouc, A. Raynaud, X. Girerd and F. Forette, Dehydroepiandrosterone (DHEA), DHEA sulfate, and aging: contribution of the DHEAge Study to a sociobiomedical issue, *Proc. Natl. Acad. Sci. U.S.A.* 97 (2000), pp. 4279-4284.

Baxendale, P. M., M. J. Reed, et al. (1981). "Inability of human endometrium or myometrium to aromatize androstenedione." *J Steroid Biochem* 14(3): 305-6.

Bélanger, B. Candas, A. Dupont, L. Cusan, P. Diamond, J. L. Gomez and F. Labrie, Changes in serum concentrations of conjugated and unconjugated steroids in 40- to 80-year-old men, *J. Clin. Endocrinol. Metab.* 79 (1994), pp. 1086-1090.

Bélanger, G. Pelletier, F. Labrie, O. Barbier and S. Chouinard, Inactivation of androgens by UDP-glucuronosyltransferase enzymes in humans, *Trends Endocrinol. Metab.* 14 (2003), pp. 473-479.

Beral, V. (2003). "Breast cancer and hormone-replacement therapy in the Million Women Study." *Lancet* 362(9382): 419-27.

Beral, V., D. Bull, et al. (2005). "Endometrial cancer and hormone-replacement therapy in the Million Women Study." *Lancet* 365(9470): 1543-51.

Berger, L., M. El-Alfy, et al. (2005). "Effects of dehydroepiandrosterone, Premarin and Acolbifene on histomorphology and sex steroid receptors in the rat vagina." *J Steroid Biochem Mol Biol* 96(2): 201-15.

Bulun, S. E., Z. Lin, et al. (2005). "Regulation of aromatase expression in estrogen-responsive breast and uterine disease: from bench to treatment." *Pharmacol Rev* 57(3): 359-83.

J. E. Buster, P. R. Casson, A. B. Straughn, D. Dale, E. S. Umstot, N. Chiamori and G. E. Abraham, Postmenopausal steroid replacement with micronized dehydroepiandrosterone: preliminary oral bioavailability and dose proportionality studies, *Am. J. Obstet. Gynecol.* 166 (1992), pp. 1163-1168 discussion 1168-1170.

Chlebowski, R. T., S. L. Hendrix, et al. (2003). "Influence of estrogen plus progestin on breast cancer and mammography in healthy postmenopausal women: the Women's Health Initiative Randomized Trial." *Jama* 289(24): 3243-53.

D. L. Coleman, E. H. Leiter and R. W. Schwizer, Therapeutic effects of dehydroepiandrosterone (DHEA) in diabetic mice, *Diabetes* 31 (1982), pp. 830-833.

Colditz, G. A., K. M. Egn, et al. (1993). "Hormone replacement thrapy and riks of breast cancer: results from epidemiologic studies." *Am. J. Obstet. Gynecol.* 168: 1473-1480.

Colditz, G. A., S. E. Hankinson, et al. (1995). "The use of estrogens and progestins and the risk of breast cancer in postmenopausal women." *N. Engl. T. Med.* 332: 1589-1593.

Collaborative Group on Hormonal Factors in Breast Cancer (1997). "Breast cancer and hormone replacement therapy: collaborative reanalysis of data from 51 epidemiological studies of 52,705 women with breast cancer and 108,411 women without breast cancer." *Lancet* 350(9084): 1047-59.

Corrao, G., A. Zambon, et al. (2008). "Menopause hormone replacement therapy and cancer risk: an Italian record linkage investigation." *Ann Oncol* 19(1): 150-5.

Coughlin, S. S., A. Giustozzi, et al. (2000). "A meta-analysis of estrogen replacement therapy and risk of epithelial ovarian cancer." *J Clin Epidemiol* 53(4): 367-75.

Deutsch, S., R. Ossowski, et al. (1981). "Comparison between degree of systemic absorption of vaginally and orally administered estrogens at different dose levels in postmenopausal women." *Am J Obstet Gynecol* 139(8): 967-8.

Dew, J. E., B. G. Wren, et al. (2003). "A cohort study of topical vaginal estrogen therapy in women previously treated for breast cancer." *Climacteric* 6(1): 45-52.

P. Diamond, L. Cusan, J. L. Gomez, A. Bélanger and F. Labrie, Metabolic effects of 12-month percutaneous DHEA replacement therapy in postmenopausal women, *J. Endocrinol.* 150 (1996), pp. S43-S50.

Dugal, R., K. Hesla, et al. (2000). "Comparison of usefulness of estradiol vaginal tablets and estriol vagitories for treatment of vaginal atrophy." *Acta Obstet Gynecol Scand* 79(4): 293-7.

Englund, D. E. and E. D. Johansson (1978). "Plasma levels of oestrone, oestradiol and gonadotrophins in postmenopausal women after oral and vaginal administration of conjugated equine oestrogens (Premarin)." *Br J Obstet Gynaecol* 85(12): 957-64.

Fallowfield, L., D. Cella, et al. (2004). "Quality of life of postmenopausal women in the Arimidex, Tamoxifen, Alone or in Combination (ATAC) Adjuvant Breast Cancer Trial." *J Clin Oncol* 22(21): 4261-71.

Feeley, K. M. and M. Wells (2001). "Hormone replacement therapy and the endometrium." *J Clin Pathol* 54(6): 435-40.

Furuhjelm, M., E. Karlgren, et al. (1980). "Intravaginal administration of conjugated estrogens in premenopausal and postmenopausal women." *Int J Gynaecol Obstet* 17(4): 335-9.

Galhardo, C. L., J. M. Soares, Jr., et al. (2006). "Estrogen effects on the vaginal pH, flora and cytology in late posimenopause after a long period without hormone therapy." *Clin Exp Obstet Gynecol* 33(2): 85-9.

Gambrell, R. D., Jr., F. M. Massey, et al. (1980). "Use of the progestogen challenge test to reduce the risk of endometrial cancer." *Obstet Gynecol* 55(6): 732-8.

Garg, P. P., K. Kerlikowske, et al. (1998). "Hormone replacement therapy and the risk of epithelial ovarian carcinoma: a meta-analysis." *Obstet Gynecol* 92(3): 472-9.

Grady, D., T. Gebretsadik, et al. (1995). "Hormone replacement therapy and endometrial cancer risk: a meta-analysis." *Obstet Gynecol* 85(2): 304-13.

Gupta, P., B. Ozel, et al. (2008). "The effect of transdermal and vaginal estrogen therapy on markers of postmenopausal estrogen status." *Menopause* 15(1): 94-7.

Holmberg, L. and H. Anderson (2004). "HABITS (hormonal replacement therapy after breast cancer—is it safe?), a randomised comparison: trial stopped." *Lancet* 363(9407): 453-5.

Holmberg, L., O. E. Iversen, et al. (2008). "Increased risk of recurrence after hormone replacement therapy in breast cancer survivors." *J Natl Cancer Inst* 100(7): 475-82.

Holmgren, P. A., M. Lindskog, et al. (1989). "Vaginal rings for continuous low-dose release of oestradiol in the treatment of urogenital atrophy." *Maturitas* 11(1): 55-63.

Hulley, S. B. (2002). "Noncardiovascular disease outcomes during 6.8 years of hormone therapy: Heart and estrogen/progestin replacement study follow-up (HERS II)." *JAMA* 288: 58-66.

Jick, S. S., A. M. Walker, et al. (1993). "Estrogens, progesterone, and endometrial cancer." *Epidemiology* 4(1): 20-4.

C. C. Johnston Jr., S. L. Hui, R. M. Witt, R. Appledorn, R. S. Baker and C. Longcope, Early menopausal changes in bone mass and sex steroids, *J. Clin. Endocrinol. Metab.* 61 (1985), pp. 905-911.

D. W. Hum, A. Belanger, E. Levesque, O. Barbier, M. Beaulieu, C. Albert, M. Vallee, C. Guillemette, A. Tchernof, D. Turgeon and S. Dubois, Characterization of UDP-glucuronosyltransferases active on steroid hormones, *J. Steroid Biochem. Mol. Biol.* 69 (1999), pp. 413-423.

H. Kawano, H. Yasue, A. Kitagawa, N. Hirai, T. Yoshida, H. Soejima, S. Miyamoto, M. Nakano and H. Ogawa, Dehydroepiandrosterone supplementation improves endothelial function and insulin sensitivity in men, *J. Clin. Endocrinol. Metab.* 88 (2003), pp. 3190-3195.

Kendall, A., M. Dowsett, et al. (2006). "Caution: Vaginal estradiol appears to be contraindicated in postmenopausal women on adjuvant aromatase inhibitors." *Ann Oncol* 17(4): 584-7.

Kvorning, J. D. N. and H. K. Jensen (1986). *Pharmaceutical development of lose-dose estradiol vagitories.* International Workshop, Copenhagen.

Labrie, C., A. Bélanger, et al. (1988). "Androgenic activity of dehydroepiandrosterone and androstenedione in the rat ventral prostate." *Endocrinology* 123: 1412-1417.

Labrie, F. (1991). "Intracrinology." *Mol. Cell. Endocrinol.* 78: C113-C118.

F. Labrie, Future perspectives of SERMs used alone and in combination with DHEA, *Endocr. Relat. Cancer* 13 (2006), pp. 335-355.

Labrie, F. (2007). "Drug Insight: breast cancer prevention and tissue-targeted hormone replacement therapy." *Nature Clinical Practice, Endocrinology & Metabolism* 3(8): 584-593.

F. Labrie, A. Bélanger, J. Simard, V. Luu-The and C. Labrie, DHEA and peripheral androgen and estrogen formation: intracrinology, *Ann. N.Y. Acad. Sci.* 774 (1995), pp. 16-28.

Labrie, F., A. Belanger, et al. (2007). "Metabolism of DHEA in postmenopausal women following percutaneous administration." *J Steroid Biochem Mol Biol* 103(2): 178-88.

Labrie, F., A. Belanger, et al. (2007) "Bioavailability and metabolism of oral and percutaneous dehydroepiandrosterone in postmenopausal women" J Steroid Biochem Mol. Biol. October; 107(1-2):57-69.

Labrie, F., A. Bélanger, et al. (2006). "Androgen glucuronides, instead of testosterone, as the new markers of androgenic activity in women." *Journal Ster Biochem & Mol Biol* 99: 182-188.

Labrie, F., A. Bélanger, et al. (2005). "GnRH agonists in the treatment of prostate cancer." *Endocrine Reviews* 26(3): 361-379.

Labrie, F., A. Belanger, et al. (1997). "Marked decline in serum concentrations of adrenal C19 sex steroid precursors and conjugated androgen metabolites during aging." *J Clin Endocrinol Metab* 82: 2396-2402.

Labrie, F., A. Belanger, et al. (2007a). "Bioavailability and metabolism of oral and percutaneous dehydroepiandrosterone in postmenopausal women." *J Steroid Biochem Mol Biol* 107(1-2): 57-69.

F. Labrie, A. Bélanger, P. Bélanger, R. Bérubé, C. Martel, L. Cusan, J. Gomez, B. Candas, V. Chaussade, I. Castiel, C. Deloche and J. Leclaire, Metabolism of DHEA in postmenopausal women following percutaneous administration, *J. Steroid Biochem. Mol. Biol.* 103 (2) (2007b), pp. 178-188.

Labrie, F., L. Cusan, et al. (2008). "Effect of Intravaginal DHEA on Serum DHEA and Eleven of its Metabolites in Postmenopausal Women." *Journal Ster Biochem & Mol Biol*: In press.

Labrie, F., L. Cusan, et al. (2008). "Effect of One-Week Treatment with Vaginal Estrogen Preparations on Serum Estrogen Levels in Postmenopausal Women." *Menopause* In press.

Labrie, F., L. Cusan, et al. (2008). "Changes in serum DHEA and eleven of its metabolites during 12-month percutaneous administration of DHEA." *J Steroid Biochem Mol Biol* 110(1-2): 1-9.

Labrie, F., P. Diamond, et al. (1997). "Effect of 12-month dehydroepiandrosterone replacement therapy on bone, vagina, and endometrium in postmenopausal women." *J Clin Endocrinol Metab* 82(10): 3498-505.

Labrie, F., A. Dupont, et al. (1985). Complete androgen blockade for the treatment of prostate cancer. *Important Advances in Oncology*. V. T. de Vita, S. Hellman and S. A. Rosenberg. Philadelphia, J. B. Lippincott: 193-217.

F. Labrie, V. Luu-The, S.X. Lin, C. Labrie, J. Simard, R. Breton and A. Bélanger, The key role of 17β-HSDs in sex steroid biology, *Steroids* 62 (1997), pp. 148-158.

Labrie, V. Luu-The, S.-X. Lin, J. Simard, C. Labrie, M. El-Alfy, G. Pelletier and A. Bélanger, Intracrinology: role of the family of 17β-hydroxysteroid dehydrogenases in human physiology and disease, *J. Mol. Endocrinol.* 25 (2000), pp. 1-16.

Labrie, F., V. Luu-The, et al. (2005). "Is DHEA a hormone? Starling Review." *J Endocrinol* 187: 169-196.

Labrie, F., V. Luu-The, et al. (2003). "Endocrine and intracrine sources of androgens in women: inhibition of breast cancer and other roles of androgens and their precursor dehydroepiandrosterone." *Endocrine Reviews* 24(2): 152-182.

Labrie, F., V. Luu-The, et al. (2006). "Dehydroepiandrosterone (DHEA) is an anabolic steroid like dihydrotestosterone (DHT), the most potent natural androgen, and tetrahydrogestrinone (THG)." *J Steroid Biochem Mol Biol* 100(1-3): 52-8.

F. Labrie, J. Simard, V. Luu-The, A. Bélanger, G. Pelletier, Y. Morel, F. Mebarki, R. Sanchez, F. Durocher, C. Turgeon, Y. Labrie, E. Rhéaume, C. Labrie and Y. Lachance, The 3β-hydroxysteroid dehydrogenase/isomerase gene family: lessons from type II 3β-HSD congenital deficiency. In: V. Hansson, F. O. Levy and K. Taskén, Editors, *Signal Transduction in Testicular Cells. Ernst Schering Research Foundation Workshop, vol Suppl.* 2, Springer-Verlag, Berlin (1996), pp. 185-218.

Labrie, J. Simard, V. Luu-The, A. Bélanger and G. Pelletier, Structure, function and tissue-specific gene expression of 3β-hydroxysteroid dehydrogenase/5-ene-4-ene isomerase enzymes in classical and peripheral intracrine steroidogenic tissues, *J. Steroid Biochem. Mol. Biol.* 43 (1992), pp. 805-826.

F. Labrie, R. Poulin, J. Simard, V. Luu-The, C. Labrie and A. Bélanger, Androgens, DHEA and breast cancer. In: T. Gelfand, Editor, *Androgens and Reproductive Aging*, Taylor and Francis, Oxsfordshire, UK (2006), pp. 113-135.

Labrie, Y. Sugimoto, V. Luu-The, J. Simard, Y. Lachance, D. Bachvarov, G. Leblanc, F. Durocher and N. Paquet, Structure of human type II 5*-reductase, *Endocrinology* 131 (1992), pp. 1571-1573.

Y. Labrie, F. Durocher, Y. Lachance, C. Turgeon, J. Simard, C. Labrie and F. Labrie, The human type II 17β-hydroxysteroid dehydrogenase gene encodes two alternatively-spliced messenger RNA species, *DNA Cell Biol.* 14 (1995), pp. 849-861.

Lacey, J. V., P. J. Mink, et al. (2002). "Menopausal hormone replacement therapy and risk of ovarian cancer." *JAMA* 288: 334-341.

Li, L., S. J. Plummer, et al. (2008). "A common 8q24 variant and the risk of colon cancer: a population-based case-control study." *Cancer Epidemiol Biomarkers Prev* 17(2): 339-42.

C. H. Liu, G. A. Laughlin, U. G. Fischer and S. S. Yen, Marked attenuation of ultradian and circadian rhythms of dehydroepiandrosterone in postmenopausal women: evidence for a reduced 17,20-desmolase enzymatic activity, *J. Clin. Endocrinol. Metab.* 71 (1990), pp. 900-906.

Long, C. Y., C. M. Liu, et al. (2006). "A randomized comparative study of the effects of oral and topical estrogen therapy on the vaginal vascularization and sexual function in hysterectomized postmenopausal women." *Menopause* 13(5): 737-43.

V. Luu-The, I. Dufort, N. Paquet, G. Reimnitz and F. Labrie, Structural characterization and expression of the human dehydroepiandrosterone sulfotransferase gene, *DNA Cell Biol.* 14 (1995), pp. 511-518.

V. Luu-The, Y. Zhang, D. Poirier and F. Labrie, Characteristics of human types 1, 2 and 3 17β-hydroxysteroid dehydrogenase activities: oxidation-reduction and inhibition, *J. Steroid Biochem. Mol. Biol.* 55 (1995), pp. 581-58

Lyytinen, H., E. Pukkala, et al. (2006). "Breast cancer risk in postmenopausal women using estrogen-only therapy." *Obstet Gynecol* 108(6): 1354-60.

E. G. MacEwen and I. D. Kurzman, Obesity in the dog: role of the adrenal steroid dehydroepiandrosterone (DHEA), *J. Nutr.* 121 (1991), pp. S51-S55.

Mandel, F. P., F. L. Geola, et al. (1983). "Biological effects of various doses of vaginally administered conjugated equine estrogens in postmenopausal women." *J Clin Endocrinol Metab* 57(1): 133-9.

Manonai, J., U. Theppisai, et al. (2001). "The effect of estradiol vaginal tablet and conjugated estrogen cream on urogenital symptoms in postmenopausal women: a comparative study." *J Obstet Gynaecol Res* 27(5): 255-60.

Martin, P. L., S. S. Yen, et al. (1979). "Systemic absorption and sustained effects of vaginal estrogen creams." *Jama* 242(24): 2699-700.

Marx, P., G. Schade, et al. (2004). "Low-dose (0.3 mg) synthetic conjugated estrogens A is effective for managing atrophic vaginitis." *Maturitas* 47(1): 47-54.

Mattson, L. A., G. Culberg, et al. (1989). "Vaginal administration of low dose estradiol-effects on endometrium and vaginal cytology." *Maturitas* 11: 217-222.

R. B. Mazess, On aging bone loss, *Clin. Orthop.* 165 (1982), pp. 239-252.

Meisels, A. (1967). "The maturation value." *Acta Cytol* 11: 249.

Mertens, H. J., M. J. Heineman, et al. (1996). "Androgen receptor content in human endometrium." *Eur J Obstet Gynecol Reprod Biol* 70(1): 11-3.

Mettler, L. and P. G. Olsen (1991). "Long-term treatment of atrophic vaginitis with low-dose oestradiol vaginal tablets." *Maturitas* 14(1): 23-31.

C. J. Migeon, A. R. Keller, B. Lawrence and T. H. Shepart II., Dehydroepiandrosterone and androsterone levels in human plasma. Effect of age and sex: day-to-day and diurnal variations, *J. Clin. Endocrinol. Metab.* 17 (1957), pp. 1051-1062.

A. J. Morales, J. J. Nolan, J. C. Nelson and S. S. Yen, Effects of replacement dose of dehydroepiandrosterone in men and women of advancing age, *J. Clin. Endocrinol. Metab.* 78 (1994), pp. 1360-1367.

Morales, L., P. Neven, et al. (2004). "Acute effects of tamoxifen and third-generation aromatase inhibitors on menopausal symptoms of breast cancer patients." *Anticancer Drugs* 15(8): 753-60.

N.A.M.S. (2007). "Position Statement of the North American Menopause Society." *Menopause* 14: 357-69.

Nachtigall, L. E. (1995). "Clinical trial of the estradiol vaginal ring in the U.S." *Maturitas* 22 Suppl: S43-7.

Naessen, T., K. Rodriguez-Macias, et al. (2001). "Serum lipid profile improved by ultra-low doses of 17 beta-estradiol in elderly women." *J Clin Endocrinol Metab* 86(6): 2757-62.

Nelson, H. D., K. K. Vesco, et al. (2006). "Nonhormonal therapies for menopausal hot flashes: systematic review and meta-analysis." *Jama* 295(17): 2057-71.

J. E. Nestler, C. O. Barlascini, J. N. Clore and W. G. Blackard, Dehydroepiandrosterone reduces serum low density lipoprotein levels and body fat but does not alter insulin sensitivity in normal men, *J. Clin. Endocrinol. Metab.* 66 (1988), pp. 57-61.

Nilsson, K. and G. Heimer (1992). "Low-dose oestradiol in the treatment of urogenital oestrogen deficiency—a pharmacokinetic and pharmacodynamic study." *Maturitas* 15(2): 121-7.

Notelovitz, M., S. Funk, et al. (2002). "Estradiol absorption from vaginal tablets in postmenopausal women." *Obstet Gynecol* 99(4): 556-62.

Orentreich, N., J. L. Brind, et al. (1984). "Age changes and sex differences in serum dehydroepiandrosterone sulfate concentrations throughout adulthood." *J. Clin. Endocrinol. Metab.* 59: 551-555.

Pandit, L. and J. G. Ouslander (1997). "Postmenopausal vaginal atrophy and atrophic vaginitis." *Am J Med Sci* 314(4): 228-31.

Persson, I., H. O. Adami, et al. (1989). "Risk of endometrial cancer after treatment with oestrogens alone or in conjunction with progestogens: results of a prospective study." *Bmj* 298(6667): 147-51.

Ponzone, R., N. Biglia, et al. (2005). "Vaginal oestrogen therapy after breast cancer: is it safe?" *Eur J Cancer* 41(17): 2673-81.

Rigg, L. A., H. Hermann, et al. (1978). "Absorption of estrogens from vaginal creams." *N Engl J Med* 298(4): 195-7.

B. L. Riggs, H. W. Wahner, W. L. Dunn, R. B. Mazess, K. P. Offord and L. J. Melton, Differential changes in bone mineral density of the appendicular and axial skeleton with aging: relationship to spinal osteoporosis, *J. Clin. Invest.* 67 (1981), pp. 328-335.

Riman, T., P. W. Dickman, et al. (2002). "Hormone replacement therapy and the risk of invasive epithelial ovarian cacner in Swedish women." *J Natl Cancer Inst* 94: 497-504.

Rinaldi, S., H. Dechaud, et al. (2001). "Reliability and validity of commercially available, direct radioimmunoassays for measurement of blood androgens and estrogens in postmenopausal women." *Cancer Epidemiol Biomarkers Prev* 10(7): 757-65.

Rioux, J. E., C. Devlin, et al. (2000). "17beta-estradiol vaginal tablet versus conjugated equine estrogen vaginal cream to relieve menopausal atrophic vaginitis." *Menopause* 7(3): 156-61.

Rodriguez, C., A. V. Patel, et al. (2002). "Estrogen replacement therapy and ovarian cancer mortality in a large prospective study of US women." *JAMA* 285: 1460-1465.

Rosenberg, L. U., C. Magnusson, et al. (2006). "Menopausal hormone therapy and other breast cancer risk factors in relation to the risk of different histological subtypes of breast cancer: a case-control study." *Breast Cancer Res* 8(1): R11.

Rossouw, J. E., G. L. Anderson, et al. (2002). "Risks and benefits of estrogen plus progestin in healthy postmenopausal women: principal results From the Women's Health Initiative randomized controlled trial." *Jama* 288(3): 321-33.

Salminen, H. S., M. E. Saaf, et al. (2007). "The effect of transvaginal estradiol on bone in aged women: a randomised controlled trial." *Maturitas* 57(4): 370-81.

Schiff, I., D. Tulchinsky, et al. (1977). "Vaginal absorption of estrone and 17beta-estradiol." *Fertil Steril* 28(10): 1063-6.

Schmidt, G., S. B. Andersson, et al. (1994). "Release of 17-beta-oestradiol from a vaginal ring in postmenopausal women: pharmacokinetic evaluation." *Gynecol Obstet Invest* 38(4): 253-60.

E. D. Schriock, C. K. Buffington, G. D. Hubert, B. R. Kurtz, A. E. Kitabchi, J. E. Buster and J. R. Givens, Divergent correlations of circulating dehydroepiandrosterone sulfate and testosterone with insulin levels and insulin receptor binding, *J. Clin. Endocrinol. Metab.* 66 (1988), pp. 1329-1331.

Sillero-Arenas, M., M. Delgado-Rodriguez, et al. (1992). "Menopausal hormone replacement therapy and breast cancer: a meta-analysis." *Obstet. Gynecol.* 79: 286-294.

Simon, J. A., K. Z. Reape, et al. (2007). "Randomized, multicenter, double-blind, placebo-controlled trial to evaluate the efficacy and safety of synthetic conjugated estrogens B for the treatment of vulvovaginal atrophy in healty postmenopausal women." *Fertil Steril In press.*

E. R. Simpson, Role of aromatase in sex steroid action, *J. Mol. Endocrinol.* 25 (2000), pp. 149-156.

Simunic, V., I. Banovic, et al. (2003). "Local estrogen treatment in patients with urogenital symptoms." *Int J Gynaecol Obstet* 82(2): 187-97.

Smith, D. C., R. Prentice, et al. (1975). "Association of exogenous estrogen and endometrial carcinoma." *N. Engl. J. Med.* 293: 1164-1167.

Smith, P., G. Heimer, et al. (1993). "Oestradiol-releasing vaginal ring for treatment of postmenopausal urogenital atrophy." *Maturitas* 16(2): 145-54.

Sourla, A., M. Flamand, et al. (1998). "Effect of dehydroepiandrosterone on vaginal and uterine histomorphology in the rat." *J. Steroid Biochem. Mol. Biol.* 66(3): 137-149.

Steinberg, K. K., S. B. Thacker, et al. (1991). "A meta-analysis of the effect of estrogen replacement therapy on the risk of breast cancer." *JAMA* 265: 1985-1990.

K. K. Steinberg, L. W. Freni-Titulaer, E. G. DePuey, D. T. Miller, D. S. Sgoutas, C. H. Coralli, D. L. Phillips, T. N. Rogers and R. V. Clark, Sex steroids and bone density in premenopausal and perimenopausal women, *J. Clin. Endocrinol. Metab.* 69 (1989), pp. 533-539.

Suckling, J., A. Lethaby, et al. (2006). "Local oestrogen for vaginal atrophy in postmenopausal women." *Cochrane Database System Rev* 18(4): CD001500.

Swanson, M. Lorentzon, L. Vandenput, D. Mellström, F. Labrie, A. Rane, J. Jakobsson, C. Ohlsson, UGT2B7 H268Y polymorphism is associated with serum sex steroid levels and cortical bone size in young adult men, JCEM (2007), in press.

Tchernof, J. P. Despres, A. Bélanger, A. Dupont, D. Prud'homme, S. Moorjani, P. J. Lupien and F. Labrie, Reduced testosterone and adrenal C19 steroid levels in obese men, *Metabolism* 44 (1995), pp. 513-519.

Turgeon, J. S. Carrier, E. Levesque, D. W. Hum and A. Belanger, Relative enzymatic activity, protein stability, and tissue distribution of human steroid-metabolizing UGT2B subfamily members, *Endocrinology* 142 (2001), pp. 778-787.

Utian, W. H., D. Shoupe, et al. (2001). "Relief of vasomotor symptoms and vaginal atrophy with lower doses of conjugated equine estrogens and medroxyprogesterone acetate." *Fertil Steril* 75(6): 1065-79.

Vermeulen and L. Verdonck, Radioimmunoassays of 17β-hydroxy-5*-androstan-3-one, 4-androstene-3,17-dione, dehydroepiandrosterone, 17β-hydroxyprogesterone and progesterone and its application to human male plasma, *J. Steroid Biochem.* 7 (1976), pp. 1-10.

D. T. Villareal and J. O. Holloszy, Effect of DHEA on abdominal fat and insulin action in elderly women and men: a randomized controlled trial, *JAMA* 292 (2004), pp. 2243-2248.

Voigt, L. F., N. S. Weiss, et al. (1991). "Progestagen supplementation of exogenous oestrogens and risk of endometrial cancer." *Lancet* 338(8762): 274-7.

Weisberg, E., R. Ayton, et al. (2005). "Endometrial and vaginal effects of low-dose estradiol delivered by vaginal ring or vaginal tablet." *Climacteric* 8(1): 83-92.

Wied, G. L. (1993). "Industrial developments in automated cytology as submitted by their developers." *Anal Quant Cytol Histol* 15(5): 358-70.

Wines, N. and E. Willsteed (2001). "Menopause and the skin." *Australas J Dermatol* 42(3): 149-8; quiz 159.

Zang, H., L. Sahlin, et al. (2007). "Effects of testosterone treatment on endometrial proliferation in postmenopausal women." *J Clin Endocrinol Metab* 92(6): 2169-75.

B. Zumoff, G. W. Strain, L. K. Miller and W. Rosner, Twenty-four-hour mean plasma testosterone concentration declines with age in normal premenopausal women, *J. Clin. Endocrinol. Metab.* 80 (1995), pp. 1429-1430.

Vaginal dryness is found in 75% of postmenopausal women (Wines and Willsteed 2001; N.A.M.S. 2007). For various reasons, especially the fear of complications by estrogens, only 20 to 25% of symptomatic women with vaginal atrophy seek medical treatment (Pandit and Ouslander 1997; N.A.M.S. 2007). There is thus a clear medical need and a major opportunity to improve the quality of life of a large population of women left suffering from vaginal atrophy for a large proportion of their lifetime. In can be mentioned that while hot flashes abate spontaneously with time, vaginal atrophy symptoms, namely vaginal dryness, vulvovaginal irritation/iching and dyspareunia usually increase in severity with time in the absence of treatment.

Based upon the well known fact that estrogen secretion by the ovaries ceases at menopause, systemic and local estrogens have so-far been the exclusive approach for the treatment of vaginal atrophy. However, systemic estrogens+progestin (HRT) and estrogens alone (ERT) have been shown to increase the risk of breast cancer (Steinberg, Thacker et al. 1991; Sillero-Arenas, Delgado-Rodriguez et al. 1992; Colditz, Egn et al. 1993; Colditz, Hankinson et al. 1995; Collaborative Group on Hormonal Factors in Breast Cancer 1997; Hulley 2002; Beral 2003; Chlebowski, Hendrix et al. 2003; Holmberg and Anderson 2004; Lyytinen, Pukkala et al. 2006; Corrao, Zambon et al. 2008; Holmberg, Iversen et al. 2008; Li, Plummer et al. 2008), ovarian cancer (Garg, Kerlikowske et al. 1998; Coughlin, Giustozzi et al. 2000; Lacey, Mink et al. 2002; Riman, Dickman et al. 2002; Rodriguez, Patel et al. 2002; Rossouw, Anderson et al. 2002; Lyytinen, Pukkala et al. 2006) as well as endometrial cancer (estrogens alone) (Gambrell, Massey et al. 1980; Persson, Adami et al. 1989; Voigt, Weiss et al. 1991; Jick, Walker et al. 1993; Grady, Gebretsadik et al. 1995; Beral, Bull et al. 2005). The publicity which followed the Women's Health Initiative Study (Rossouw, Anderson et al. 2002) had the greatest impact, thus putting in doubt the safety of the available treatments of menopausal symptoms (Archer 2007).

Although intravaginal formulations were developed to avoid systemic exposure to estrogens, a long series of studies have unanimously demonstrated that all intravaginal estrogen formulations lead to relatively high serum estrogen levels measured directly or through their systemic effects (Englund and Johansson 1978; Rigg, Hermann et al. 1978; Martin, Yen et al. 1979; Furuhjelm, Karlgren et al. 1980; Deutsch, Ossowski et al. 1981; Mandel, Geola et al. 1983; Nilsson and Heimer 1992; Nachtigall 1995; Ayton, Darling et al. 1996; Dugal, Hesla et al. 2000; Rioux, Devlin et al. 2000; Manonai, Theppisai et al. 2001; Notelovitz, Funk et al. 2002; Ponzone, Biglia et al. 2005; Weisberg, Ayton et al. 2005; Galhardo, Soares et al. 2006; Kendall, Dowsett et al. 2006; Long, Liu et al. 2006; Bachmann, Lobo et al. 2008). These data showing a significant increase in serum estrogen levels clearly indicate that the use of intravaginal estrogen formulations is also potentially associated with an increased risk of breast and uterine cancer (Kvorning and Jensen 1986; Mattson, Culberg et al. 1989; Rosenberg, Magnusson et al. 2006; N.A.M.S. 2007). Concerns have in fact been officially raised about the stimulatory effects of vaginal estrogen formulations on the endometrium ((N.A.M.S. 2007).

Most previous measurements of the serum estradiol ($E_2$) levels after intravaginal administration of estrogens used radioimmunoassays, a technology lacking specificity, accuracy, reliability and sensitivity (Rinaldi, Dechaud et al. 2001).

We have measured serum estrogens using GLP (Good Laboratory Practice)-validated mass spectrometry assays following intravaginal administration of the two most commonly used estrogen formulations (Labrie, Cusan et al. 2008). This study could definitively show that both the $E_2$ pill (25 µg $E_2$/day) and conjugated estrogens cream (1 g of 0.625 mg conjugated estrogens/day), after one-week of daily treatment, cause an approximately 5-fold increase in serum $E_2$ in postmenopausal women. Such data indicate that the effects of estrogens applied locally in the vagina are unlikely to be limited to the vagina and that systemic action is expected as previously suggested (Englund and Johansson 1978; Rigg, Hermann et al. 1978; Martin, Yen et al. 1979; Furuhjelm, Karlgren et al. 1980; Deutsch, Ossowski et al. 1981; Mandel, Geola et al. 1983; Nilsson and Heimer 1992; Nachtigall 1995; Ayton, Darling et al. 1996; Dugal, Hesla et al. 2000; Rioux, Devlin et al. 2000; Manonai, Theppisai et al. 2001; Notelovitz, Funk et al. 2002; Ponzone, Biglia et al. 2005; Weisberg, Ayton et al. 2005; Galhardo, Soares et al. 2006; Kendall, Dowsett et al. 2006; Long, Liu et al. 2006; Bachmann, Lobo et al. 2008).

In addition to the above-indicated safety concerns of estrogens administered both systemically and locally, recent data have clearly demonstrated that women are not only deficient in estrogens at time of menopause but that they have also been progressively deprived, starting in the thirties, from the androgens made in specific peripheral target tissues by the intracrine transformation of dehydroepiandrosterone (DHEA) into androgens and/or estrogens (Labrie, Bélanger et al. 1988; Labrie 1991; Labrie, Luu-The et al. 2003; Labrie, Luu-The et al. 2005). In fact, serum DHEA and DHEA-sulfate progressively decrease from the peak seen at the age of 30 years (Orentreich, Brind et al. 1984; Labrie, Belanger et al. 1997; Labrie, Luu-The et al. 2003) to a value 60% lower at time of menopause (Labrie, Bélanger et al. 2006).

Concerning the role of androgens in women, it is important to mention that women secrete 50% as much androgens as observed in men (Labrie, Belanger et al. 1997; Labrie, Luu-The et al. 2005). Since serum DHEA is the predominant source of androgens which play a series of physiological roles in women (Labrie, Luu-The et al. 2003; Labrie 2007), the 60% decrease in circulating DHEA already found at time of menopause leads to a similar 60% decrease in the total androgen pool (Labrie, Bélanger et al. 2006) with the resulting potential signs and symptoms of hypoandrogenicity in the bone, muscle, skin, mammary gland, vagina, brain as well as on glucose, insulin and lipid metabolism (Labrie, Luu-The et al. 2003; Labrie 2007). Among the androgen target tissues, recent data have shown that the vagina is sensitive to androgens following DHEA administration in the rat with beneficial effects, not only on the superficial epithelial layer of the vagina but also on collagen fibers in the lamina propria and on the muscularis (Berger, El-Alfy et al. 2005).

Based upon the data of our preclinical (Sourla, Flamand et al. 1998; Berger, El-Alfy et al. 2005) and clinical (Labrie, Diamond et al. 1997; Labrie, Cusan et al. 2008) studies showing beneficial effects on the vagina of DHEA administered percutaneously or locally, the present clinical trial is a prospective, randomized and placebo-controlled study of the effect of three doses of intravaginal DHEA administered daily for 12 weeks on the changes in superficial and parabasal cells, vaginal pH and the most bothersome symptom of vaginal atrophy as primary objectives. The data clearly show that locally administered DHEA is very efficient and rapid in correcting all the signs and symptoms of vaginal atrophy, a near maximal effect being already achieved at 2 weeks at a DHEA dose causing no significant change in serum estrogens or androgens while all other steroids remain unchanged or well within the range found in normal postmenopausal women.

When DHEA is administered locally in the vagina, the beneficial effects of estrogens and androgens made locally in the vagina are achieved without any significant release of estradiol or testosterone into the blood (Labrie, Cusan et al. J. Ster. Biochem. Mol. Biol. In press). In the formation of androgens and/or estrogens from DHEA by the process of intracrinology, any tissue is unpredictable because the response depends upon the activity of the enzymatic machinery specifically present in each cell of each tissue. Thus, it is not possible to predict, from the androgens and estrogens that are produced from DHEA in one tissue, the extent to which similar androgens and estrogens may be produced in another tissue.

The results of the clinical trial ERC-210 (Example 3) clearly demonstrate for the first time that the local administration of DHEA as hormone precursor replacement therapy (HPRT) is highly efficient and rapid in correcting all the symptoms and signs of vaginal atrophy in postmenopausal women. Most importantly, this is achieved at a dose (0.5%) of DHEA which does not increase the serum levels of active estrogens or androgens and with no or minimal changes in serum DHEA and any of its metabolites which all remain well within the range of values found in normal postmenopausal women (Labrie, Cusan et al. 2008).

While 75% of postmenopausal women suffer from vaginal atrophy (Wines and Willsteed 2001; N.A.M.S. 2007), thus affecting their quality of life during a major part of their lifetime, only 20% seek treatment (Pandit and Ouslander 1997). The fear of breast cancer related to increased blood levels of estrogens is the main reason involved. Since estrogen secretion into the systemic circulation is exclusively of ovarian origin and ceases at menopause, administration of estrogens to postmenopausal women does not appear to be physiological. In the aftermath of WHI, the scientific challenge is to explore alternative hormonal therapy types and formulations that would provide all the menopausal advantages of estrogens while improving women's quality of life, minimizing risks and maximizing benefits (Archer 2007). Since the non-estrogen based treatments have not shown convincing efficacy (Nelson, Vesco et al. 2006; Suckling, Lethaby et al. 2006), women and their physicians are left with no safe treatment for vaginal atrophy.

Various forms of estrogens are an efficient treatment for vulvovaginal atrophy (Pandit and Ouslander 1997; Utian, Shoupe et al. 2001). In fact, the vaginal $E_2$ tablet has shown an efficacy similar to the $E_2$ ring (Weisberg, Ayton et al. 2005) as well as to the conjugated estrogen cream (Rioux, Devlin et al. 2000; Manonai, Theppisai et al. 2001).

This novel HPRT is in marked contrast with the 5-fold increase in serum $E_2$ measured by mass spectrometry after treatment with intravaginal $E_2$ or conjugated estrogens (Labrie, Cusan et al. 2008). These recent data on the changes in serum estrogens confirm a long series of studies showing that all intravaginal estrogen formulations lead to elevated serum estrogen concentrations measured directly by radioimmunoassays or through their systemic effects (Englund and Johansson 1978; Rigg, Hermann et al. 1978; Martin, Yen et al. 1979; Furuhjelm, Karlgren et al. 1980; Deutsch, Ossowski et al. 1981; Mandel, Geola et al. 1983; Nilsson and Heimer 1992; Nachtigall 1995; Ayton, Darling et al. 1996; Dugal, Hesla et al. 2000; Rioux, Devlin et al. 2000; Manonai, Theppisai et al. 2001; Notelovitz, Funk et al. 2002; Ponzone, Biglia et al. 2005; Weisberg, Ayton et al. 2005; Galhardo, Soares et al. 2006; Kendall, Dowsett et al. 2006; Long, Liu et al. 2006; Bachmann, Lobo et al. 2008).

The most common adverse events reported with vaginal estrogens are vaginal bleeding and breast pain, both secondary to increased serum estrogens (Suckling, Lethaby et al. 2006). These side effects have been reported for the $E_2$ ring, conjugated estrogens cream as well as $E_2$ tablet (Ayton, Darling et al. 1996; Weisberg, Ayton et al. 2005). As mentioned above, concerns also exist about the stimulatory effects of vaginal estrogens on the endometrium (N.A.M.S. 2007). Uterine bleeding, breast pain and perineal pain were reported in 9% of women who took the vaginal tablet for 24 weeks while 34% complained of the same symptoms in the vaginal conjugated estrogen cream group (Rioux, Devlin et al. 2000). (Suckling, Lethaby et al. 2006) reported no difference between the different vaginal estrogen preparations.

It is well known that atrophic vaginitis in postmenopausal women can be worsened or induced by the use of aromatase inhibitors for the treatment of breast cancer. In fact, these drugs exert their benefits on breast cancer by decreasing $E_2$ biosynthesis in all tissues, thus increasing the frequency and severity of menopausal symptoms (Fallowfield, Cella et al. 2004; Morales, Neven et al. 2004). In a recent study where seven breast cancer patients treated with aromatase inhibitors received Vagifem at a daily dose of 25 μg for 2 weeks and then, thereafter, twice weekly, serum $E_2$ rose from a median of 3 pmol/l to 72 pmol/l, at 2 weeks (range 3 to 232) (Kendall, Dowsett et al. 2006). Serum $E_2$ levels generally decreased thereafter to values of 40 pmol/l or less although values of 137 and 219 pmol/l were found at weeks 7-10. A patient who received Premarin cream had serum $E_2$ levels of 83 pmol/l at 2 weeks. It should be mentioned that blood sampling for $E_2$ measurement was performed at time of patient's visit, a timing not likely to correspond to the highest serum $E_2$ levels after Vagifem administration. It is thus more than likely that the values reported in (Kendall, Dowsett et al. 2006) underestimate, up to an unknown extent, the true elevation of serum $E_2$ after intravaginal Vagifem pill or Premarin cream administration. The authors concluded that the use of Vagifem with aromatase inhibitors is contraindicated. These findings obtained in breast cancer women treated with aromatase inhibitors raise a serious issue about the use of any vaginal as well as any oral or transdermal estrogen preparation in postmenopausal women.

The relatively high elevation of serum $E_2$ following treatment with various vaginal estrogen preparations leading to increased risk of breast cancer is a well recognized issue (Rosenberg, Magnusson et al. 2006). Although a study having a small number of events and a short follow-up (a 4.7% subgroup among 1472 women) did not find a statistically significant difference in disease-free survival in the subgroup of women who used vaginal estrogen (Dew, Wren et al. 2003), it does not appear reasonable or acceptable to increase the serum $E_2$ levels during breast cancer therapy when the objective of treatment with aromatase inhibitors is precisely to achieve the maximal inhibition of $E_2$ biosysthesis.

In an early study with Vagifem, a $E_2$ tablet, when administered at the 25 μg dose, led to serum $E_2$ levels of 80 pmol/l with values below 50 pmol/l at 14 h and later (Kvorning and Jensen 1986). In a more recent study with Vagifem, maximal and mean 24 h serum $E_2$ concentrations were measured at 180±99 pmol/l and 84 pmol/l for the μg dose while values of 81±62 pmol/l and 40 pmol/l, respectively, were found for the 10 μg dose (Notelovitz, Funk et al. 2002). Other vaginal estrogen tablets and creams have led to even higher serum estrogen levels (Schiff, Tulchinsky et al. 1977; Rioux, Devlin et al. 2000).

With the 10 μg and 25 μg $E_2$ vaginal tablets, serum $E_2$ was found to increase to maximal values of approximately 90 and 160 pmol/l, respectively, from basal values of approximately 35 pmol/l (Nilsson and Heimer 1992). Serum $E_2$ with Vagifem has been reported at a $C_{max}$ of 51±34 pg/ml on day 1, this value being practically unchanged on days 14 (47±21 pg/ml) and 84 (49±27 pg/ml) (Vagifem, Physician Package Insert 1999).

In another study, after 52 weeks of treatment with 25 μg Vagifem, the serum levels of $E_2$ were reported to have remained unchanged from 10.3±21.5 pg/ml to 9.9 pg/ml (Bachmann, Lobo et al. 2008). Such data can be explained by the fact that blood sampling was most likely performed 3 or 4 days after Vagifem application. It is also important to mention that the elevated pretreatment serum $E_2$ levels in that study most likely relate to the lack of specificity of the immuno-based assays used since normal $E_2$ serum levels measured by mass spectrometry in postmenopausal women are two to three times lower (Labrie, Bélanger et al. 2006).

In an early study, the oral and vaginal administration of 1.25 mg Premarin led to serum levels of $E_2$ and estrone up to at least 100 pg/ml and 1000 pg/ml respectively, during the 24 h following administration, the levels being somewhat higher after vaginal application. Serum gonadotropin levels were decreased in most subjects (Englund and Johansson 1978). Similar data were reported by (Rigg, Hermann et al. 1978). In a recent study, following 3 months of daily oral or intravaginal administration of 0.625 mg Premarin, the serum $E_2$ levels increased to 83.1 and 58.6 pg/ml respectively (Long, Liu et al. 2006), thus illustrating the very important systemic exposure after both intravaginal and oral estrogen administration since serum $E_2$ was only 36% lower after intravaginal compared to oral administration of conjugated estrogens. In a 12-week study with Premarin vaginal cream at the daily 2 g dose, three times a week, 21% of women experienced bleeding after a progestogen test (Nachtigall 1995). Moreover, of these women, 12% showed an increase in endometrial thickness at echography.

No increase in serum $E_1$, $E_2$ or $E_1S$ levels have been reported with the use of the vaginal ring (Nachtigall 1995; Gupta, Ozel et al. 2008) although significant increases in $E_1S$ and $E_2$ have been observed in women older than 60 years (Naessen, Rodriguez-Macias et al. 2001). In the ESTring group of a recent study, serum $E_2$ increased from 16±22 pmol/l to 49±64 pmol/l at week 24 (Weisberg, Ayton et al. 2005). In the Vagifem group, on the other hand, serum $E_2$ increased from 15±33 pmol/l to 36±51 pmol/l. These authors, nevertheless, reported that serum $E_2$ remained within or near the values found in normal postmenopausal women. At 48 weeks of treatment with ESTring or Vagifem, 30-32% of women had complaints of urinary frequency, 36-39% of urinary urgency and 18-33% complained of dyspareunia (Weisberg, Ayton et al. 2005).

Three studies have documented that the $E_2$ vaginal ring permits low serum $E_2$ during the 90-day period except for the burst in serum estrogen that reaches the lower region of those seen in normal cycling women or 100 to 200 pmoles/L during the first 0.5-8 h after insertion of the ring (Holmgren, Lindskog et al. 1989; Schmidt, Andersson et al. 1994) (Baker and Jaffe 1996). That the daily delivery of 7.5 μg of $E_2$ by the intravaginal route has systemic effects is shown by the observation of a significant increase in bone mineral density of total hip and lumbar spine after 2 years of treatment with such an intravaginal dose of $E_2$ (Salminen, Saaf et al. 2007).

As mentioned above, concerns exist about the stimulatory effects of vaginal estrogens on the endometrium (N.A.M.S. 2007). After 12 weeks of treatment of 32 women with 25 µg of intravaginal $E_2$ (Vagifem), one patient had simple hyperplasia without atypia (Bachmann, Lobo et al. 2008). In a 24-week study involving 80 women, one case of proliferative endometrium was found (Rioux, Devlin et al. 2000) and in another 52-week study of 31 women, two had a proliferative endometrium (Mettler and Olsen 1991).

In a 12-week study with Premarin vaginal cream at the dose of 2 g, three times a week, 21% of women experienced bleeding after a progestogen test (Nachtigall 1995). Of these, 12% showed an increase in endometrial thickness by echography. The use of a 0.3 mg dose of conjugated estrogens administered intravaginally, three times a week, may induce endometrial proliferation, albeit rarely, since endometrial proliferation was seen in only one of twenty cases (Nachtigall 1995).

The sustained-releaset estradiol ring (ESTring) induced endometrial proliferation similar to the 0.625 mg Premarin cream (Ayton, Darling et al. 1996) but less then the 1.25 mg Premarin cream (Nachtigall 1995). In fact, both the vaginal ring (ESTring) and conjugated estrogen cream (Premarin cream) have been shown to induce endometrial proliferation (Nachtigall 1995; Ayton, Darling et al. 1996). Two cases of moderate endometrial proliferation or hyperplasia in an endometrial polyp were found with the $E_2$ ring (Nachtigall 1995), while two cases of hyperplasia (one simple and one complex, without atypia) were found with the conjugated estrogen cream in a trial of conjugated estrogen cream versus $E_2$ tablet (Rioux, Devlin et al. 2000). The $E_2$ vaginal tablet has been associated with endometrial hyperplasia similar to the estriol vaginal tablet (Dugal, Hesla et al. 2000; Manonai, Theppisai et al. 2001) but less than the conjugated estrogens cream (Manonai, Theppisai et al. 2001).

Although serum estrogen levels are increased to a lower degree following local intravaginal application compared to oral or percutaneous HRT or ERT, the risk of breast cancer remains an issue and the safety of the intravaginal estrogens is in doubt (Suckling, Lethaby et al. 2006; N.A.M.S. 2007). In fact, although the increase in serum estrogens is lower after the intravaginal compared to the oral or percutaneous route of administration, it is significantly elevated above normal postmenopausal levels for all intravaginal estrogen formulations (Ponzone, Biglia et al. 2005).

In addition to the increased breast cancer risk associated with the administration of estrogens, it is important to remember that the true hormonal difference between the postmenopausal women who do not suffer from vaginal atrophy (estimated at 25% of the postmenopausal population) and the remaining 75% of postmenopausal women who suffer from vaginal atrophy (Wines and Willsteed 2001; N.A.M.S. 2007), is not related to the secretion of estrogens in the systemic circulation since ovarian estrogen secretion has ceased in all women at time of menopause. Consequently, a deficit in estrogen secretion is not a valid explanation for the occurrence of symptoms of vaginal atrophy in the majority of postmenopausal women.

Sex steroid formation, however, does not stop with the cessation of ovarian function at menopause. The recent progress in our understanding of the endocrine physiology in women show that after menopause, DHEA secreted by the adrenals is the only source of sex steroids made exclusively in target tissues (Labrie 1991). Contrary to the estrogens of ovarian origin which are secreted in the general circulation where they can be measured, DHEA is an inactive precursor which is transformed in the peripheral tissues at various rates according the level of expression of the steroidogenic enzymes in each tissue. The process of intracrinology permits local intratissular formation of active sex steroids with no significant release of the active steroids in the circulation (Labrie, Dupont et al. 1985; Labrie, Bélanger et al. 1988; Labrie 1991; Labrie, Luu-The et al. 2005).

The secretion of DHEA, however, decreases with age, a 60% decrease being already observed at time of menopause (Labrie, Luu-The et al. 2003; Labrie, Bélanger et al. 2005; Labrie, Luu-The et al. 2005; Labrie, Bélanger et al. 2006; Labrie, Luu-The et al. 2006; Labrie 2007). The only difference between the symptomatic and the asymptomatic postmenopausal women is the amount of DHEA secreted by the adrenals or the sensitivity of the vaginal tissue to DHEA. The difference of sensitivity of different women is likely to be related up, to an unknown extent, to the level of activity of the enzymatic machinery specific to each cell type in each tissue (Labrie 1991; Labrie, Bélanger et al. 2005). With this knowledge, DHEA and not estrogens is a physiological hormonal replacement therapy for postmenopausal women.

As well demonstrated in our previous studies (Labrie 1991; Labrie, Luu-The et al. 2003; Labrie, Luu-The et al. 2005; Labrie, Belanger et al. 2007), supplementation with physiological amounts of exogeneous DHEA permits the biosynthesis of androgens and/or estrogens only in the appropriate target tissues which contain the required steroidogenic enzymes of intracrinology (Labrie, Luu-The et al. 2005). The active androgens and estrogens synthesized locally from DHEA in peripheral target tissues exert their action in the same cells where their formation takes place. Most importantly, very little leakage of the active sex steroids into the circulation takes place, thus explaining the marked beneficial effects observed in the vagina with no significant change in circulating estrogens or androgens (Labrie, Cusan et al. 2008). This local biosynthesis, action and inactivation of estrogens and androgens in target tissues eliminates the exposure of other tissues to excess sex steroids and thus eliminates the increased risks of undesirable side effects from elevated estrogen exposure, including breast, ovarian and uterine cancer (Gambrell, Massey et al. 1980; Persson, Adami et al. 1989; Steinberg, Thacker et al. 1991; Voigt, Weiss et al. 1991; Sillero-Arenas, Delgado-Rodriguez et al. 1992; Colditz, Egn et al. 1993; Jick, Walker et al. 1993; Colditz, Hankinson et al. 1995; Grady, Gebretsadik et al. 1995; Collaborative Group on Hormonal Factors in Breast Cancer 1997; Garg, Kerlikowske et al. 1998; Coughlin, Giustozzi et al. 2000; Hulley 2002; Lacey, Mink et al. 2002; Riman, Dickman et al. 2002; Rodriguez, Patel et al. 2002; Rossouw, Anderson et al. 2002; Beral 2003; Chlebowski, Hendrix et al. 2003; Holmberg and Anderson 2004; Beral, Bull et al. 2005; Lyytinen, Pukkala et al. 2006; Corrao, Zambon et al. 2008; Holmberg, Iversen et al. 2008; Li, Plummer et al. 2008).

Change in pH is now recognized as a valid parameter which reflects the beneficial effect of vaginal atrophy therapy. After 12 weeks of intravaginal treatment with 25 µg B2, the percentage of patients having a pH less than 5.0 was 51% compared to 21% in the placebo group (Bachmann, Lobo et al. 2008). At baseline, however, 11.2% and 13% of women had a pH below 5.0 in the two corresponding groups. In the clinical trial ERC-210 (Example 3), no patient had a pH below 5.0 at start of therapy and 12%, 36%, 46% and 48% had pH values below 5.0 at 12 weeks in the 0%, 0.25%, 0.5% and 1.0% DHEA groups, respectively.

In clinical trial ERC-210 (Example 3), the effect of DHEA on the maturation of the vaginal epithelial cells is particularly rapid: with the 0.5% DHEA ovule, 79% of the maximal effect on parabasal cells was already observed at 2 weeks while 48% of the maximal stimulatory effect exerted on superficial cells was observed at the same time interval. On the other hand, 85% of the maximal effect of 0.5% DHEA on the percentage of superficial cells was achieved at 4 weeks. Similarly, 63% of the maximal effect of 0.5% DHEA on the most bothersome symptom was observed at 2 weeks and 87% was reached at 4 weeks. Moreover, only 17.8% of women reported no change in their most bothersome symptom at 12 weeks in the 0.5% DHEA group compared to 48.8% in the placebo group.

The effect of DHEA on parabasal cells is rapid since the % of parabasal cells was decreased to less than 20% at one month with the three DHEA doses used. The effect on the % of superficial cells is also very rapid with 100% of the effect being seen at 2 weeks with the high (1%) DHEA dose. In a study with vaginal estrogen cream or tablet, approximately 50% of the effect measured at 12 weeks was observed at 2 weeks (Rioux, Devlin et al. 2000). Such data indicate that the rapidity of the effect of DHEA is not inferior and possibly superior to the effect of the vaginal $E_2$ and conjugated estrogen formulations.

In a study of the effect of oral estrogens in 71 postmenopausal women, daily administration of 0.3 mg oral synthetic conjugated estrogens decreased parabasal cells from 23% to 2.3% while superficial cells increased from 2.1% to 15.9% (Marx, Schade et al. 2004). In a study comparing the 0.3 mg and 0.625 mg doses of conjugated equine estrogens (Utian, Shoupe et al. 2001), the 0.625 mg dose has shown a greater effect on the % of superficial cells.

In a recent study, the vaginal maturation value (VMV) increased from 27.45 at baseline to 56.85 (p<0.0001) in the estrogen-treated group (Simon, Reape et al. 2007). The percentage of superficial cells increased by 17.15 from baseline while the percentage of parabasal cells decreased by 41.66% in the estrogen-treated group. In the same study, the vaginal pH decreased from 6.74 at baseline to 5.05 (decrease of 1.69 or 24%) in the estrogen group). The severity of the most bothersome symptoms decreased from 2.58 to 1.04 (−1.54) in the estrogen group compared to a decrease from 2.59 to 1.84 (−0.75) in the placebo group. Such data observed with estrogens are comparable to the 1.56 decrease in severity of the most bothersome symptoms at 12 weeks in the 0.5% DHEA group and the 0.67 decrease in the placebo group observed in clinical trial ERC-210 (Example 3).

At week 12, 11% of ESTring subjects and 24% of Vagifem subjects had persistent atrophic epithelium. At week 48, the respective values were 8% and 14% (Weisberg, Ayton et al. 2005). At 48 weeks of treatment with Vagifem or ESTring, vaginal dryness was still present in 33% of women (Weisberg, Ayton et al. 2005). Pruritus vulvae, on the other hand, remained present in 15% and 20% of women after treatment with ESTring and Vagifem, respectively while 33% and 28% of women still had dyspareunia after treatment with ESTring and Vagifem, respectively. Bleeding after the progestogen test was 7% in the Vagifem group and 0% in the ESTring group.

After 3 months of daily administration of 0.625 mg Premarin orally or intravaginally (cream), respective 70.6% and 75% improvements of dyspareunia were observed (Long, Liu et al. 2006). It was concluded in that study that 1 g of 0.625 mg Premarin was the minimal dose for the treatment of sexual dysfunction.

In women who received 25 μg $E_2$ intravaginally, dyspareunia persisted in 12.4% of cases after 12 months of treatment (Simunic, Banovic et al. 2003). The success rate of therapy of local $E_2$ tablets was 84.5% as judged by patients and 86.1% as judged by doctors (Simunic, Banovic et al. 2003). Bachman et al, 1992 (Bachmann, Notelovitz et al. 1992) have reported that 40-50% of women on oral estrogen replacement therapy had persistent complaints of vaginal dryness.

As reported previously after 12 months of treatment with DHEA (Labrie, Diamond et al. 1997), the clinical trial ERC-210 (Example 3) shows no effect on endometrial histology after 3 months of intravaginal administration of the hormone precursor DHEA as shown by histopathological examination of the endometrial biopsies obtained before and after 12 weeks of treatment. These findings are in agreement with the absence of aromatase activity in the human endometrium (Baxendale, Reed et al. 1981; Bulun, Lin et al. 2005). These findings are also strongly supported by the well recognized clinical observation that endometrial atrophy is characteristic of postmenopause despite the continuous secretion of DHEA thorought life (Labrie, Luu-The et al. 2005; Labrie, Bélanger et al. 2006). The absence in the human endometrium of the steroidogenic enzymes necessary to transform DHEA into estrogens is in agreement with the physiological role of the endometrium which is active exclusively during the reproductive years when its function is essentially controlled by hormones of ovarian and placental origins. There is no physiological role of the endometrium after menopause which would justify any continued action of estrogens after cessation of estrogen secretion by the ovaries. Accordingly, the enzymes required for the synthesis of estrogens from DHEA are not expressed in the endometrium which a tissue fully dependent upon estrogens of ovarian origin.

Estrogens administered alone have long been known to stimulate endometrial proliferation (Smith, Prentice et al. 1975) while progestins administered in combination with estrogens inhibit the stimulatory effect of estrogens (Feeley and Wells 2001). Since androgen receptors are expressed in the human endometrium and stroma (Mertens, Heineman et al. 1996), it is of interest to mention that a clinical study which investigated the effect of androgens showed no effect on the endometrium of a relatively high dose of testosterone in postmenopausal women (testosterone undecanoate, 40 mg every second day) (Zang, Sahlin et al. 2007). In women who received estradiol valerate (2 mg/day), Ki labeling increased by 50% at 3 months of treatment while simultaneous administration of testosterone decreased proliferation to 28%. Ki67 labeling was increased only in the two groups receiving estrogen but it was decreased by the addition of testosterone in the stroma. While having no stimulatory effect on endometrial proliferation in women, testosterone appears to exert some antiestrogenic effect in the endometrium.

While the FDA guidance encourages sponsors to develop the lowest doses and exposures for both estrogens and progestins, we must recognize that although estrogens are efficient in correcting the symptoms of vaginal atrophy and vasomotor symptoms, systemic estrogens are not the physiological hormones that permit 25% of postmenopausal women to avoid the moderate to severe symptoms of vaginal atrophy. These women remain relatively asymptomatic thorough all their postmenopausal years. Since the only source of sex steroids in postmenopausal women, both symptomatic and asymptomatic, is local estrogen and androgen biosynthesis from adrenal DHEA, by the mechanisms of intracrinology. Replacement with DHEA is the only physiological approach which permits to provide women suffering from postmenopausal symptoms the missing amount of DHEA responsible for their symptoms. With the approach called hormone precursor replacement therapy (HPRT), vaginal atrophy and vasomotor symptoms should be corrected with no more risk than that of the fellow postmenopausal women who have no symptoms of vaginal atrophy because of a higher exposure to DHEA and the sex steroids made intracellularly by the process of intracrinology.

Sex steroid precursors administered in accordance with the invention are preferably administered in a dosage range (1) between 0.5 to 100 mg per day, (preferably 3 to 50 mg per day, and most preferably between 3 and 13 mg per day), when intravaginally administered; (2) in a dosage range between 15 to 200 mg per day (preferably 30 mg to 100 mg per day), when administered on the skin; (3) in a dosage range between 10 to 200 mg per day (preferably 25 mg to 100 mg per day), e.g., 75 mg per day, when orally administered; or (4) in a dosage range between 1.0 to 25 mg per day (preferably 3.25 to 20 mg per day), when parentally administered (i.e. intramuscular, or subcutaneous).

In a pharmaceutical composition for vaginal administration, DHEA or other precursor is preferably present in a concentration between 0.1 and 10% by weight relative to total weight of the composition more preferably between 0.2 and 3.0 percent, especially between 0.25 and 2.0 percent. For example, a 1.3 milliliter (mL) vaginal suppository having a 0.5% DHEA (by weight of total composition), administered once daily, desirably provides 6.5 mg/day of DHEA. Larger or smaller suppositories may be used, as may different concentrations, while maintaining dosage in the desired range.

In a pharmaceutical composition for administration on skin, DHEA or other precursor is preferably present in a concentration between 0.1 and 10% by weight relative to total weight of the composition more preferably between 0.2 and 2.0 percent, especially between 0.3 and 1.5 percent.

In a pharmaceutical composition for oral administration, DHEA or other precursor is preferably present in a concentration between 5 and 98% by weight relative to total weight of the composition more preferably between 10 and 50 percent, especially between 15 and 40 percent.

In a pharmaceutical composition for parental administration (i.e. intramuscular, or subcutaneous), DHEA or other precursor is preferably present in a concentration between 0.2 mg/mL and 25 mg/mL, more preferably between 0.65 and 15 mg/mL, especially between 2 mg/mL and 10 mg/mL.

EXAMPLE OF EFFICAY OF THE INVENTION

Example 1

Clinical Trail ERC-213

DHEA Bioavailability Following Administration of Vaginal Suppositories in Post Menopausal Women with Vaginal Atrophy Phase I Randomized, Placebo-Controlled Parmacokinetics and Local Action of Daily Administration of DHEA Suppositories for One Week The primary objective of that study was the evaluation of the systemic bioavailability of DHEA and its metabolites following daily intravaginal application of suppositories at four different DHEA concentrations. This study was a randomized, placebo-controlled and double-blind trial of 10-subjects per arm. Forty postmenopausal women were thus randomized to receive a daily dose of one suppository of the following DHEA concentrations: 0.0%, 0.5% (6.5 mg of DHEA/suppository), 1.0% (13 mg of DHEA/suppository) or 1.8% (23.4 mg of DHEA/suppository).

The maturation index as well as the vaginal pH were measured at pretreatment as well as after 7 days of treatment in order to obtain an indication of the local effect of DHEA during that short time period.

As illustrated in FIG. 1B, Table 1 and Table 2, daily intravaginal application of a 1.3 ml suppository containing 0.5%, 1.0% and 1.8% DHEA led to a progressive increase of serum DHEA with $AUC_{0-24h}$ values of 24.8±4.8 ng.h/ml, 56.2±8.9 ng.h/ml ($p<0.05$), 76.2±10.3 ng.h/ml ($p<0.01$) and 114.3±9.97 ng.h/ml ($p<0.01$), respectively. There was thus 127%, 207% and 361% increases over control at the 0.5%, 1.0% and 1.8% doses of DHEA, respectively. As observed for all other steroids, similar values of the $AUC_{0-24\,h}$ were observed on days 1 and 7.

In fact, the average serum value of 4.76±0.42 ng/ml of DHEA following treatment with the highest dose (Table 2) is similar to the value of 4.47±2.19 ng/ml found in forty-seven (47) 30-35 year-old premenopausal normal women (Labrie, Bélanger et al. 2006). That serum DHEA following any of the doses of DHEA used remains within the limits of normal premenopausal women is well illustrated in FIG. 7A.

As observed previously following oral or percutaneous administration of DHEA (Labrie, Bélanger et al. 2007), serum 5-diol follows a pattern almost superimposable to that of DHEA, although much lower concentrations are seen. In fact, the $AUC_{0-24\,h}$ value goes from 5.60±0.60 ng.h/ml in the placebo group on day 7 to 9.83±1.14 ($p<0.05$), 13.8±1.87 ($p<0.01$) and 21.0±1.66 ($p<0.01$) at the 0.5%, 1.0% and 1.8% DHEA doses, respectively (1D, Table 1). Such changes correspond to 75%, 147% and 276% increases over control. Only the 1.8% DHEA dose causes increases in serum 5-diol exceeding the values found in normal premenopausal women (FIG. 7B) during the 24 h following daily intravaginal administration of DHEA on day 7.

Figure 2:
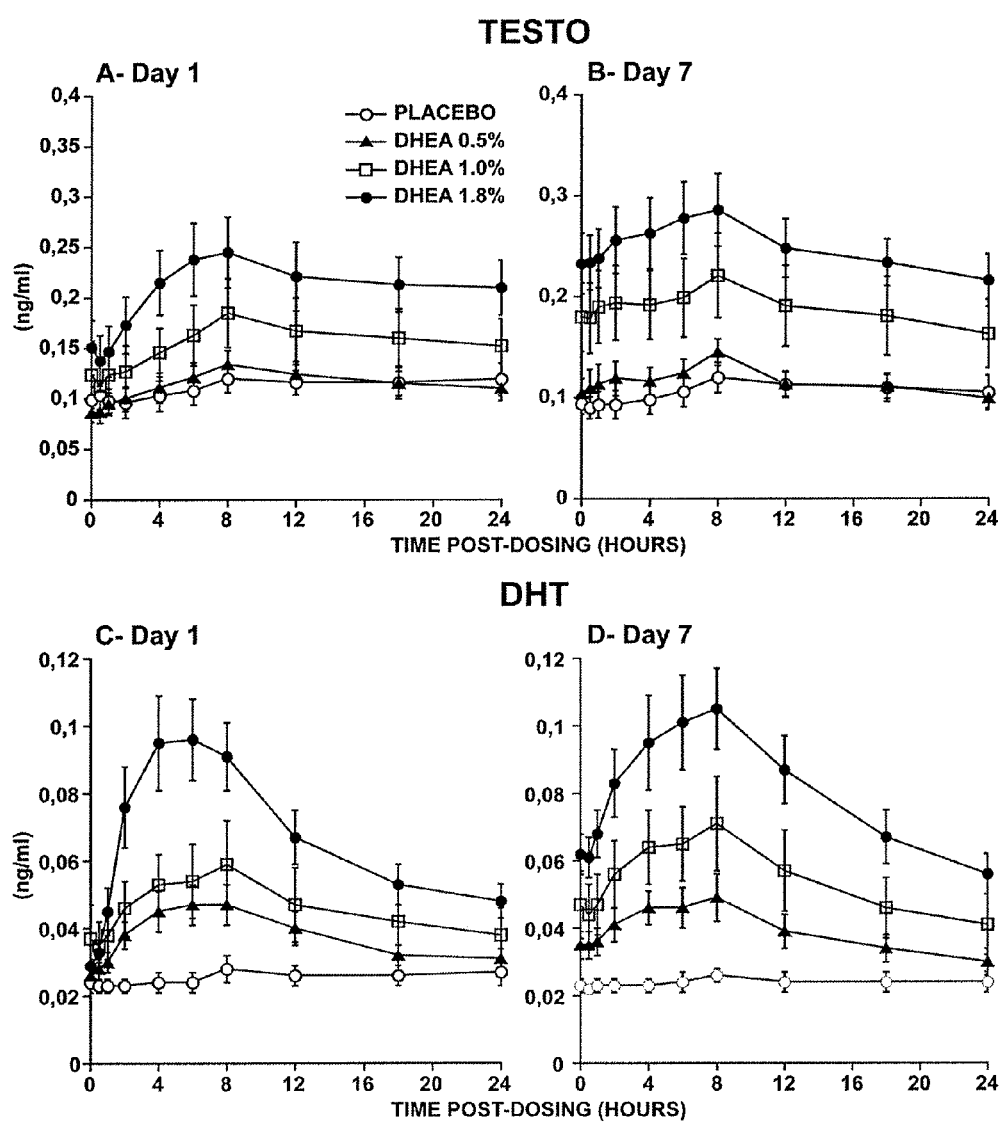
FIG. 2 shows Serum Levels of Testo and DHT on Day 1 or Day 7 in 40-75 Year-Old Postmenopausal Women Following Daily Administration of Vaginal Suppositories Containing 0%, 0.5%, 1.0% or 1.8% of DHEA (n=8). Data are expressed as means±SEM (n=8 to 9). Testo levels from one patient in the placebo group were excluded because of unexplained high levels of Testo not reflected in any other steroid.
Figure 7:
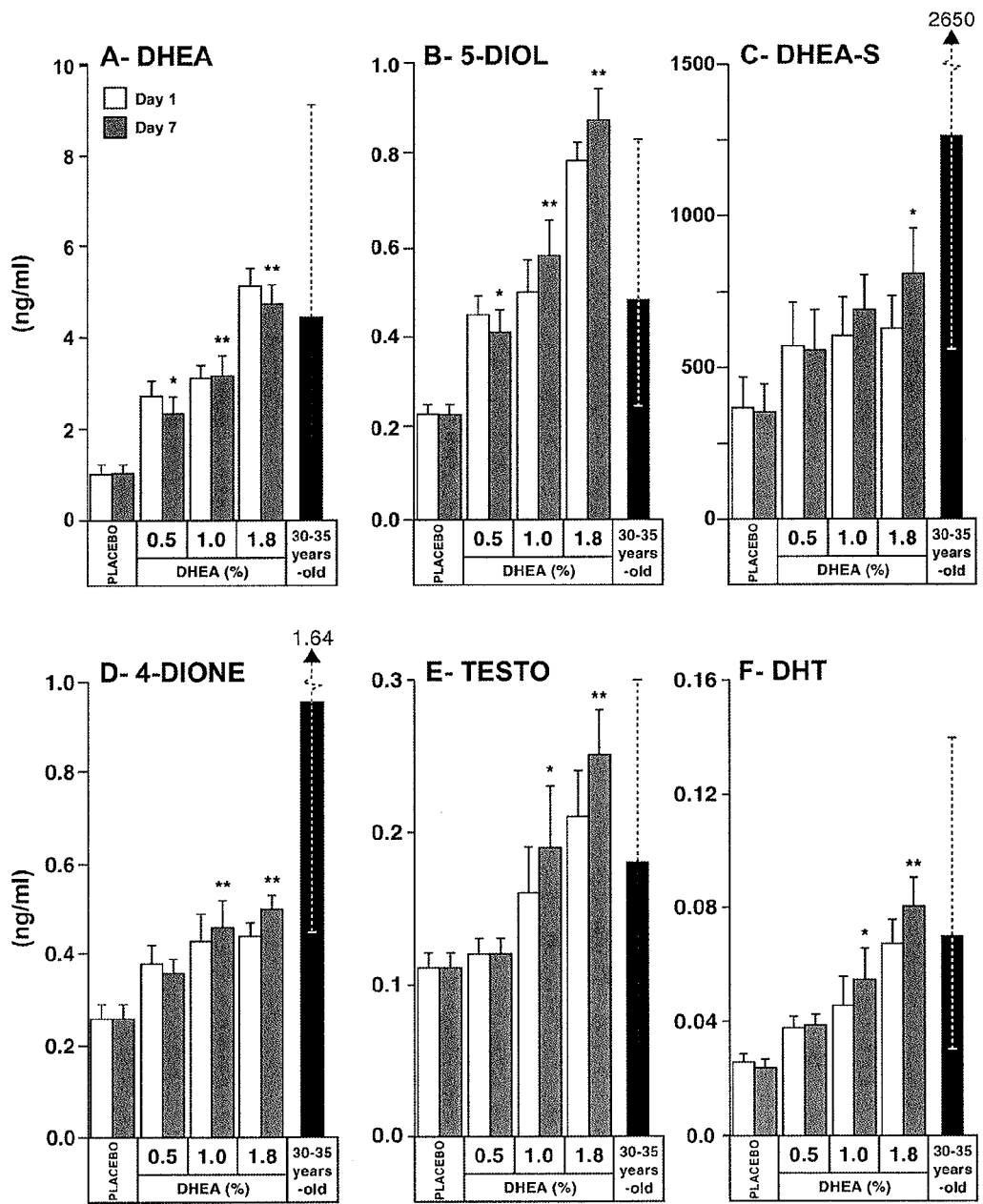
FIG. 7 shows Average 24-Hour Serum Concentration ($AUC_{0-24h}/24$) of DHEA, 5-Diol, DHEA-S, 4-Dione, Testo and DHT Measured on Day 1 or Day 7 Following Once Daily Administration of Vaginal Suppositories Containing 0%, 0.5%, 1.0% or 1.8% of DHEA. Data are expressed as means±SEM (n=8 to 10). Testo levels from one patient in the placebo group were excluded (n=8 in that group). Serum steroid concentrations measured in 30-35 year-old premenopausal women are added as reference. Data are expressed as mean (n=47) while the $5^{th}$ and $95^{th}$ centiles are indicated (dashed lines). *, p<0.05, **, p<0.01, experimental (Day 7) versus placebo (Day 7).

The AUC 0-24 h value of serum Testo showed no significant change at the 0.5% dose (2.79±0.30 ng.h/ml versus 2.58±0.33 ng.h/ml in the placebo group) (FIG. 2B). At the 1.0% and 1.8% doses, AUC 0-24h values of 4.54±0.91 ng.h/ml ($p<0.05$) and 5.97±0.69 ng.h/ml ($p<0.01$) were found (Table 1). These values translate into average serum Testo levels of 0.11±0.01 (N.S.), 0.12±0.01 (N.S.), 0.19±0.04 ($p<0.05$) and 0.25±0.03 ($p<0.01$) ng/ml, respectively. Even at the highest 1.8% DHEA dose used, serum Testo levels remained within the normal range of premenopausal women measured at 0.18±0.07 ng/ml (0.06-0.31, 5th-95th centiles) (Labrie, Bélanger et al. 2006) (FIG. 7E). The 1.0% dose (0.18±0.07 ng/ml), on the other hand, corresponds exactly to the values found in normal premenopausal women, namely 0.19±0.4 (FIG. 7E).

FIGS. 2C and D, serum DHT increased from an $AUC_{0-24\,h}$ value of 0.58±0.07 ng.h/ml in the placebo group on day 7 to 0.93±0.11 (N.S.), 1.31±0.26 ($p<0.05$) and 1.93±0.23 ($p<0.01$) ng.h/ml in the 0.5%, 1.0% and 1.8% DHEA groups, respectively (Table 2). These values correspond to average serum DHT levels of 0.02±0.01, 0.04±0.01, 0.05±0.01 and 0.08±0.01 ng/ml (Table 2), thus reaching, at the highest DHEA dose, the normal serum DHT levels of 0.07±0.03 ng/ml observed in premenopausal women (Labrie, Bélanger et al. 2006) (FIG. 7F).

Figure 3:
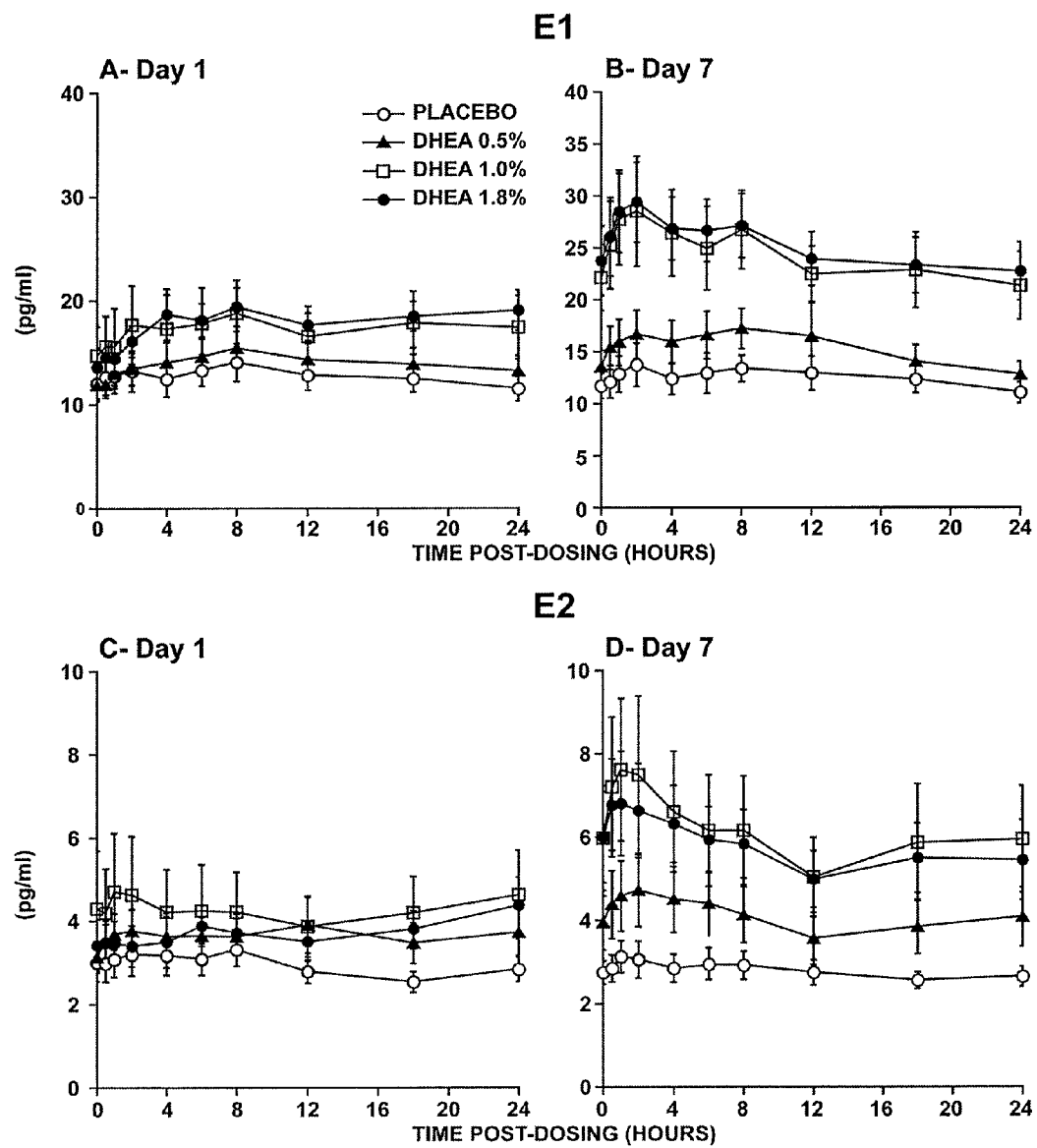
FIG. 3 shows Serum Levels of $E_1$ and $E_2$ on Day 1 or Day 7 in 40-75 Year-Old Postmenopausal Women Following Daily Administration of Vaginal Suppositories Containing 0%, 0.5%, 1.0% or 1.8% of DHEA. Data are expressed as means±SEM (n=9 or 10).

The average serum $E_1$ levels were measured at 12.6±1.41 ng/ml in the placebo group on day 7 (Table 2) while there was no significant change at the 0.5% DHEA dose (15.4±2.04 ng/ml). An increase to 24.1±3.54 ng/ml ($p<0.01$) and 25.0±2.85 ng/ml ($p<0.01$) was observed at the 1.0% and 1.5% DHEA doses, respectively. The corresponding $AUC_{0-24\,h}$ values are illustrated in FIG. 3B and are indicated in Table 1.

Average serum $E_2$ levels were measured at 2.77±0.29 pg/ml and 4.04±0.69 pg/ml (N.S.) in the placebo and 0.5% DHEA groups, respectively (Table 2). Average serum $E_2$ concentrations of 6.01±1.31 pg/ml ($p<0.05$) and 5.68±0.84 pg/ml ($p<0.05$) were found on day 7 in women who received the 1.0% and 1.8% DHEA doses for absolute increases of 3.18 and 2.85 pg/ml over placebo, respectively. Comparable findings were observed for serum $E_1$-S with average serum levels of 0.12±0.02 ng/ml and 0.13 ng/ml (N.S.) in the placebo and 0.5% DHEA groups, respectively (Table 2). Values of 0.18±0.03 ng/ml and 0.25±0.25 ng/ml were measured in the 1.0% and 1.8% DHEA groups, respectively. Only the 1.8% DHEA group shows a statistical difference (p<0.01) with the placebo group.

Figure 4:
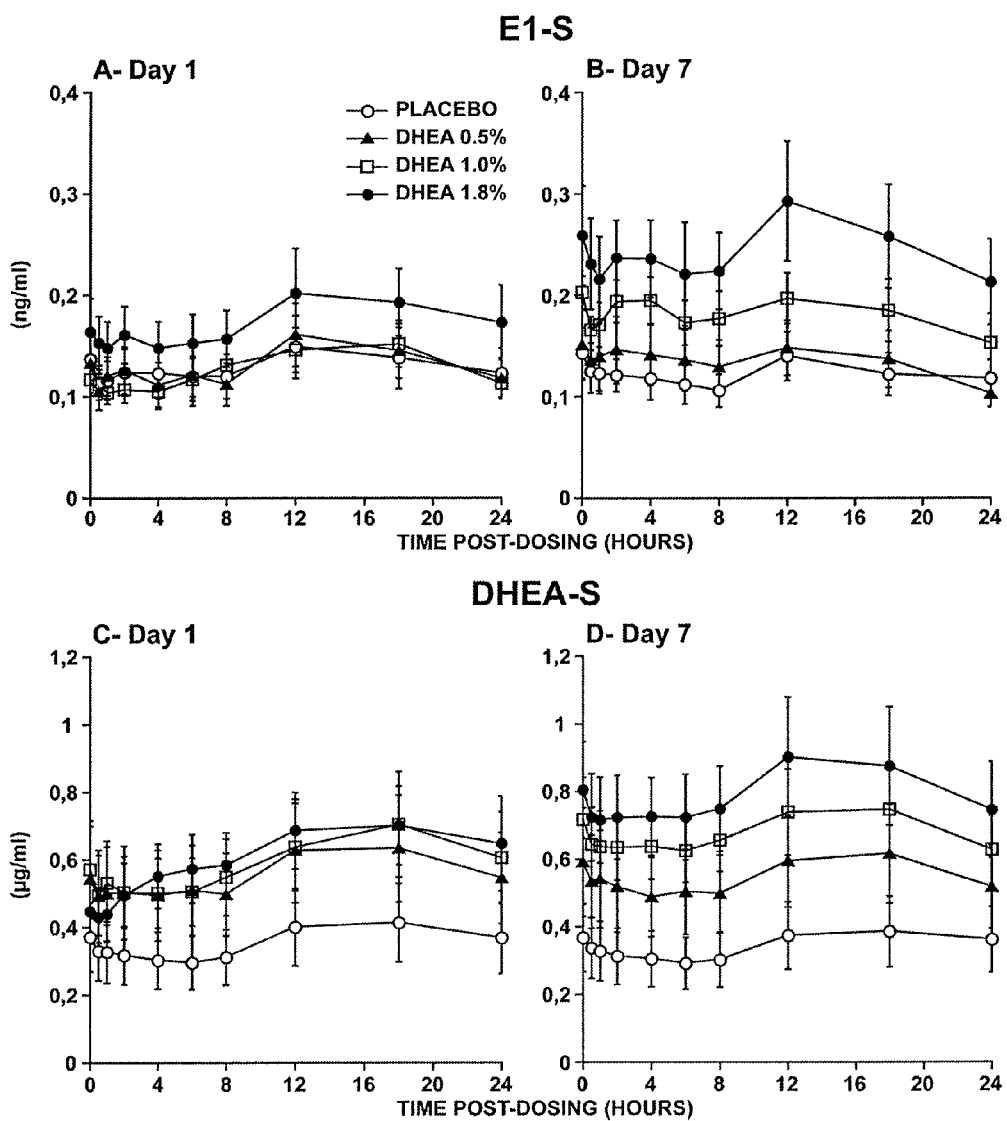
FIG. 4 shows Serum Levels of $E_1$-S and DHEA-S on Day 1 or Day 7 in 40-75 Year-Old Postmenopausal Women Following Daily Administration of Vaginal Suppositories Containing 0%, 0.5%, 1.0% or 1.8% of DHEA. Data are expressed as means±SEM (n=9 or 10).

As can be seen in 4B and D, a comparable pattern is seen for both $E_1$-S and DHEA-S. The AUC 0-24 value of serum DHEA-S was measured at 8.35±2.22 ng.h/ml in the placebo group and 13.3±3.16 ng.h/ml in the 0.5% DHEA group (N.S.). With the two higher DHEA doses, the $AUC_{0-24\,h}$ values were measured at 16.5±2.71 ng.h/ml (N.S.) and 19.3±3.59 ng.h/ml (p<0.05), respectively (FIG. 4D, Table 1). These values of DHEA-S at all doses of DHEA remain below the serum DHEA-S levels observed in premenopausal women which show an average of 1.27±0.62 ng/ml (7C).

Figure 5:
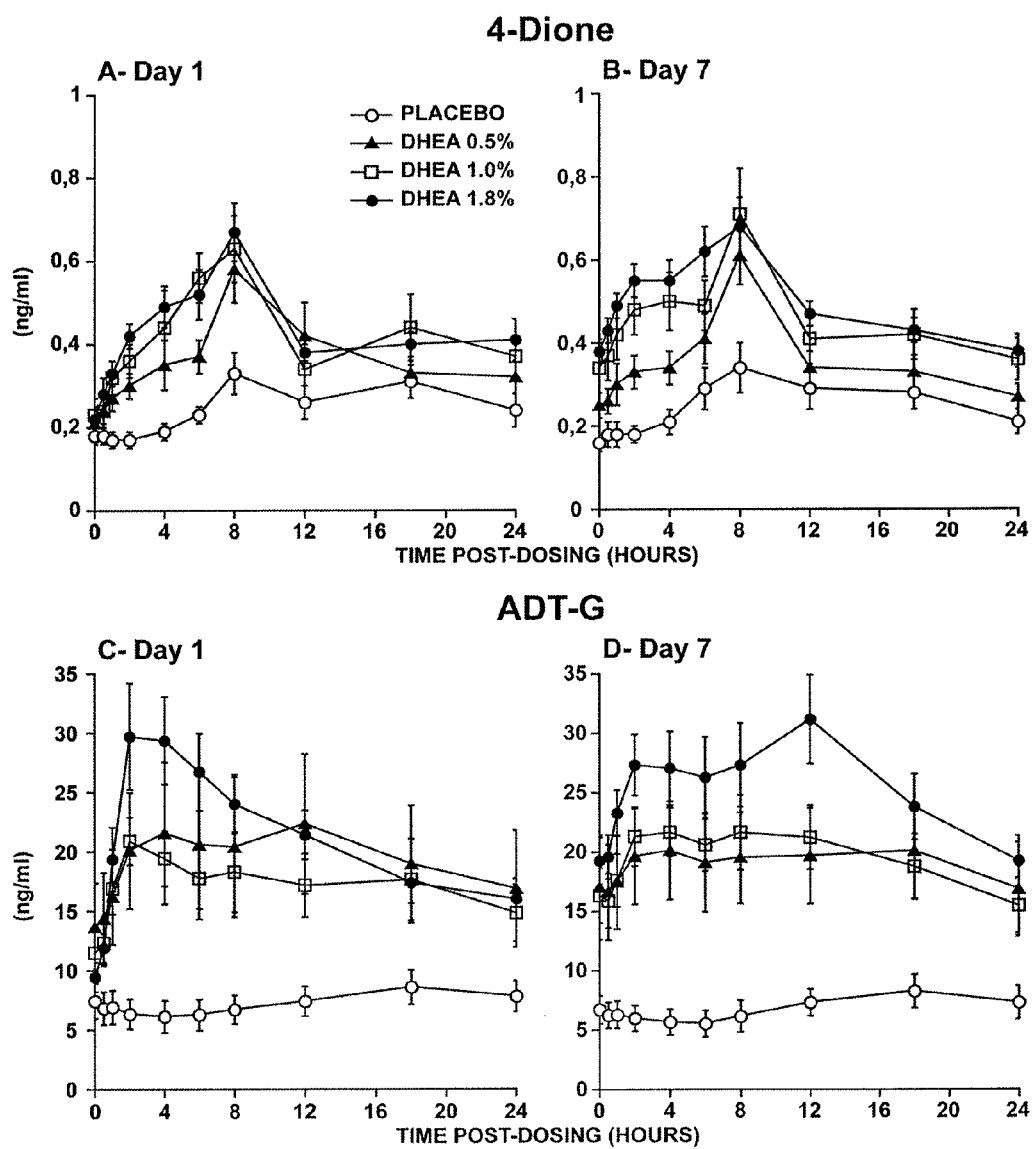
FIG. 5 shows Serum Levels of 4-Dione and ADT-G on Day 1 or Day 7 in 40-75 Year-Old Postmenopausal Women Following Daily Administration of Vaginal Suppositories Containing 0%, 0.5%, 1.0% or 1.8% of DHEA. Data are expressed as means±SEM (n=9 or 10).
Figure 6:
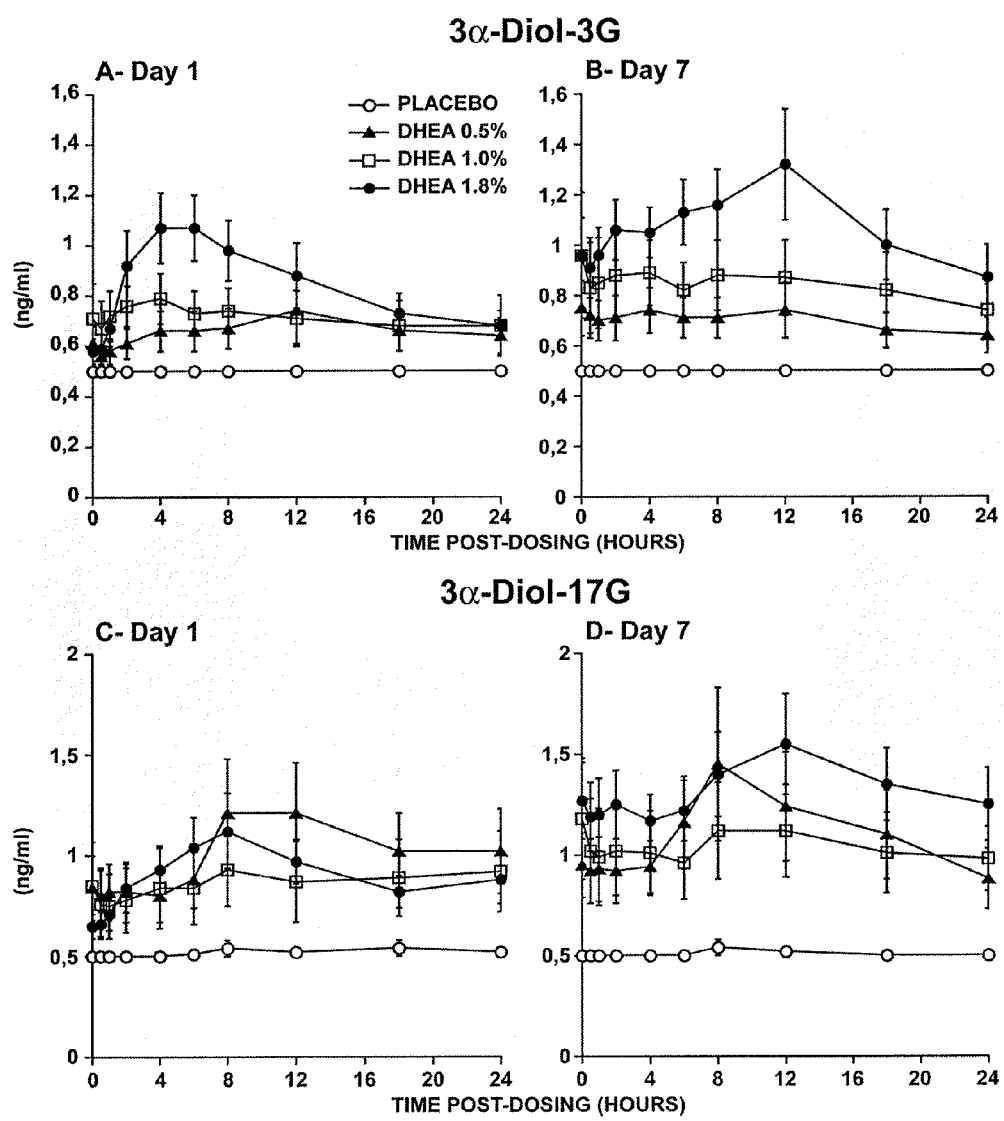
FIG. 6 shows Serum Levels of 3α-Diol-3G and 3α-Diol-17G on Day 1 or Day 7 in 40-75 Year-Old Postmenopausal Women Following Once Daily Administration of Vaginal Suppositories Containing 0%, 0.5%, 1.0% or 1.8% of DHEA. Data are expressed as means±SEM (n=9 or 10).

As illustrated in FIG. 5B, the $AUC_{0-24\,h}$ values of serum 4-dione following DHEA administration on day 7 were measured at 6.34±0.80 and 8.71±0.84 ng.h/ml (N.S.) in the placebo and 0.5% DHEA groups, respectively. At the two higher DHEA doses, the $AUC_{0-24\,h}$ values of 4-dione increased slightly to 11.1±1.51 (p<0.01) and 11.9±0.81 (p<0.01) ng.h/ml, respectively. As can be seen in 7D and Table 2, all these values of serum 4-dione remained well below the average serum 4-dione concentrations observed in normal premenopausal women. In fact, the highest DHEA dose led to average serum 4-dione concentrations of 0.50±0.03 ng/ml while the average value in 30-35 year old cycling women is 0.96±0.35 ng/ml (Labrie, Bélanger et al. 2006) (Appendix 2), thus reaching only 50% of the serum 4-dione levels observed in premenopausal women.

Figure 8:
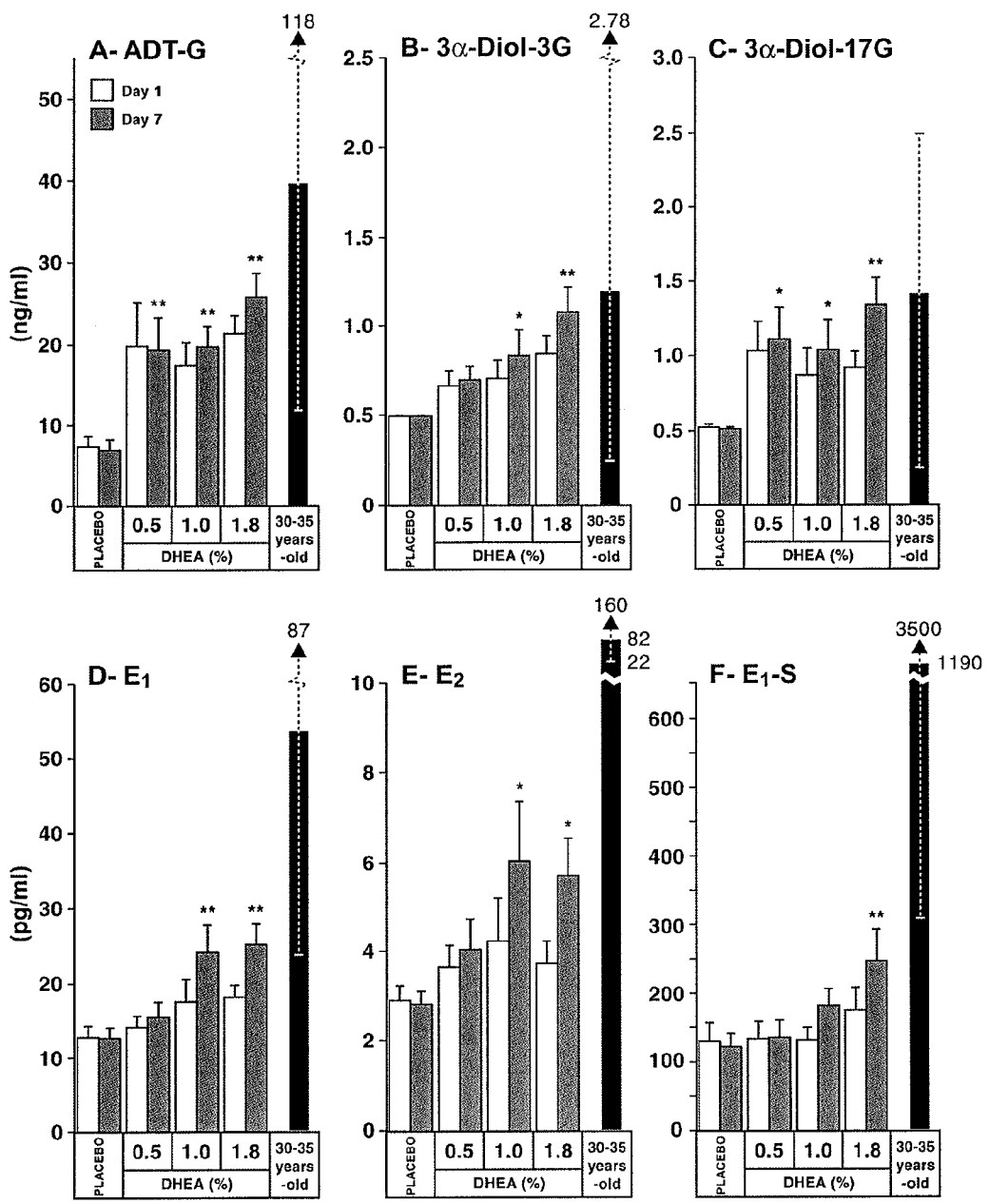
FIG. 8 shows Average 24-Hour Serum Concentration (AUC0-24h/24) of ADT-G, 3α-Diol-3G, 3α-Diol-17G, $E_1$, $E_2$ and $E_1$-S Measured on Day 1 or Day 7 Following Daily Administration of Vaginal Suppositories Containing 0%, 0.5%, 1.0% or 1.8% of DHEA. Data are expressed as means±SEM (n=9 or 10). Serum steroid concentrations measured in 30-35 year-old premenopausal women are added as reference. Data are expressed as mean (n=47) while the $5^{th}$ and $95^{th}$ centiles are indicated (dashed lines). *, p<0.05, **, p<0.01, experimental (Day 7) versus placebo (Day 7).

Considering the crucial role of measurements of the serum levels of ADT-G, 3α-diol-3G and 3α-diol-17G (Labrie, Bélanger et al. 2006) it is of interest to see in 5D and Table 2 that serum levels of ADT-G increased from an average value of 6.97±1.20 ng/ml in the placebo group to 19.2±3.99 ng.h/ml in the 0.5% DHEA group (p<0.01). Values of 19.7±2.48 and 25.7±2.88 ng.h/ml were measured in the 1.0% and 1.8% DHEA groups, respectively (p<0.01 vs placebo for both DHEA-treated groups). Similar changes can be seen for the minor androgen metabolites 3α-diol-3G and 3α-diol-17G (6B, 6D, 8B and 8C, Table 1 and Table 2). It is important to indicate, as illustrated in FIG. 8, that even at the highest dose of DHEA used, the average serum levels of ADT-G 3α-diol-3G and 3α-diol-17G remained 36%, 11% and 6% below the average serum levels found in premenopausal women.

Figure 9:
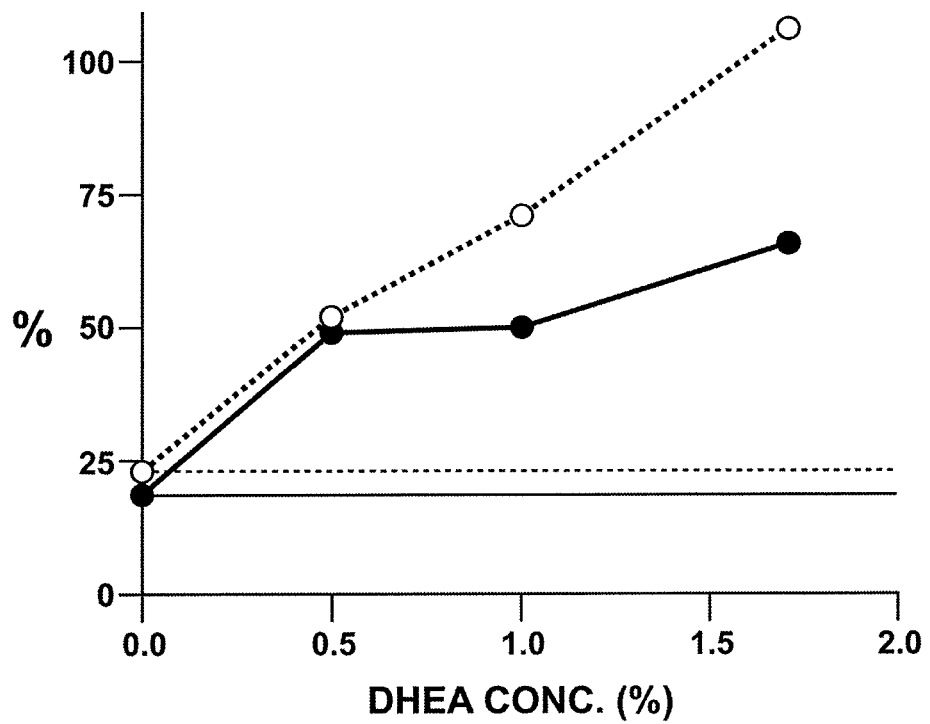
FIG. 9 shows Changes of the Serum Levels of the Sum of the Androgen Metabolites ADT-G, 3α-Diol-17G in Postmenopausal Women with Vaginal Atrophy Following Intravaginal Administration of Increasing Doses of DHEA. The data are expressed as percentage of the serum levels of the same steroid metabolites observed in young adult (30-35 year-old) cycling premenopausal women. The level of transformation is obtained by dividing the sum of the serum levels of ADT-G, 3α-diol-3G and 3α-diol-17G in women who received the 0.5%, 1.0% and 1.8% DHEA doses by the values found in premenopausal women (data from Labrie et al., 2006). The serum DHEA changes compared to normal premenopausal women are also indicated as comparison to indicate efficiency of transformation (0 - - - 0). . . . ; _____ and basal levels of androgen metabolites and DHEA, respectively.

As shown in Table 2, the sum of the androgen metabolite glucuronides measured over a 24 h period on day 7 of the administration of a 1.3 ml suppository containing 1.8% DHEA (23.4 mg DHEA) is only 28.2 ng/ml while the mean serum concentration of the same metabolite in 30-35 year-old premenopausal women is 42.8 ng/ml (Labrie, Bélanger et al. 2006) (Appendix 2). Accordingly, the highest DHEA dose used leads to only 65.7% of the value corresponding to the total androgen metabolites found in normal cycling young women. The 0.5% and 1.0% DHEA doses, on the other hand, lead to sums of androgen metabolites of 21.02 ng and 21.53 ng/ml, respectively, thus corresponding to only 49.0% and 50.2% of the values observed in premenopausal women (FIG. 9). We have previously found that daily oral administration of 100 mg of DHEA leads to 74% of the levels found in premenopausal women (Labrie, Bélanger et al. 2007).

We have previously observed that following oral or percutaneous administration of DHEA, the changes in serum DHEA are an approximately 100% overestimate of the changes in steroid formation reflected by changes in serum ADT-G, 3α-diol-3G and 3α-diol-17G (Labrie, Bélanger et al. 2007). As can be seen in FIG. 9, average serum DHEA levels went from 23% of the value observed in premenopausal women of the placebo group to 52%, 71% and 106% in women who received the 0.5%, 1.0% and 1.8% DHEA doses, respectively. The data of FIG. 9 indicate that changes in serum DHEA following intravaginal DHEA administration are also an overestimate of the changes in androgen formation and probably even more in estrogen formation as illustrated by the even smaller changes in serum $E_1$-S (Table 1). In fact, at the 1.0% dose, serum androgen metabolites increased by 31.6% of the value found in premenopausal women while serum DHEA increased by 49.1% (55% overestimate). At the highest DHEA dose, serum androgen metabolites increased by 47.1% while serum DHEA increased by 83.5% (77% overestimate).

TABLE 1

Areas Under the Curve ($AUC_{0-24\,h}$) Values of DHEA and Eleven of its Metabolites on Days 1 and 7 of Daily Administration of Intravaginal DHEA Suppositories to 40-75 Year-Old Postmenopausal Women with Vaginal Atrophy.

| GROUP | VALUE | DHEA | | 5-DIOL | | TESTO | | DHT | | E1 | | E2 | |
|---|---|---|---|---|---|---|---|---|---|---|---|---|---|
| | | DAY 1 ng·h/mL | DAY 7 ng·h/mL | DAY 1 ng·h/mL | DAY 7 ng·h/mL | DAY 1 ng·h/mL | DAY 7 ng·h/mL | DAY 1 ng·h/mL | DAY 7 ng·h/mL | DAY 1 pg·h/mL | DAY 7 pg·h/mL | DAY 1 pg·h/mL | DAY 7 pg·h/mL |
| PLACEBO | MEAN | 24.47 | 24.82 | 5.55 | 5.60 | 2.71[a] | 2.58[a] | 0.61 | 0.58 | 305.58 | 301.92 | 69.51 | 66.49 |
| | SEM | 4.80 | 4.77 | 0.59 | 0.60 | 0.34 | 0.33 | 0.08 | 0.07 | 34.56 | 33.77 | 7.63 | 6.90 |
| DHEA 0.5% | MEAN | 65.49 | 56.17 | 10.91 | 9.83 | 2.79 | 2.79 | 0.91 | 0.93 | 336.52 | 369.69 | 87.79 | 96.93 |
| | SEM | 7.80 | 8.94 | 1.03 | 1.14 | 0.29 | 0.30 | 0.10 | 0.11 | 37.96 | 48.86 | 11.34 | 16.46 |
| DHEA 1.0% | MEAN | 74.82 | 76.22 | 12.09 | 13.84 | 3.79 | 4.54 | 1.11 | 1.31 | 418.08 | 578.59 | 101.57 | 144.34 |
| | SEM | 6.71 | 10.28 | 1.66 | 1.87 | 0.70 | 0.91 | 0.23 | 0.26 | 70.91 | 84.90 | 22.97 | 31.47 |
| DHEA 1.8% | MEAN | 123.52 | 114.30 | 18.98 | 21.04 | 5.13 | 5.97 | 1.62 | 1.93 | 433.74 | 600.93 | 89.76 | 136.28 |
| | SEM | 9.43 | 9.96 | 1.05 | 1.66 | 0.72 | 0.69 | 0.19 | 0.23 | 37.68 | 68.35 | 11.65 | 20.27 |

| GROUP | E1-S | | DHEA-S | | 4-DIONE | | ADT-G | | 3α-DIOL-3G | | 3α-DIOL-17G | |
|---|---|---|---|---|---|---|---|---|---|---|---|---|
| | DAY 1 ng·h/mL | DAY 7 ng·h/mL | DAY 1 μg·h/mL | DAY 7 μg·h/mL | DAY 1 ng·h/mL | DAY 7 ng·h/mL | DAY 1 ng·h/mL | DAY 7 ng·h/mL | DAY 1 ng·h/mL | DAY 7 ng·h/mL | DAY 1 ng·h/mL | DAY 7 ng·h/mL |
| PLACEBO | 3.15 | 2.93 | 8.71 | 8.35 | 6.23 | 6.34 | 176.53 | 167.39 | 12.00 | 12.00 | 12.53 | 12.20 |
| | 0.62 | 0.47 | 2.41 | 2.22 | 0.71 | 0.80 | 30.86 | 28.87 | 0.00 | 0.00 | 0.53 | 0.20 |

TABLE 1-continued

Areas Under the Curve (AUC$_{0-24\,h}$) Values of DHEA and Eleven of its
Metabolites on Days 1 and 7 of Daily Administration of Intravaginal DHEA
Suppositories to 40-75 Year-Old Postmenopausal Women with Vaginal Atrophy.

| DHEA 0.5% | 3.19 | 3.24 | 13.59 | 13.29 | 9.03 | 8.71 | 474.10 | 461.15 | 16.01 | 16.73 | 24.68 | 26.74 |
|---|---|---|---|---|---|---|---|---|---|---|---|---|
| | 0.60 | 0.63 | 3.42 | 3.16 | 0.98 | 0.84 | 126.99 | 95.77 | 2.02 | 1.97 | 4.70 | 5.02 |
| DHEA 1.0% | 3.14 | 4.37 | 14.42 | 16.49 | 10.28 | 11.06 | 417.73 | 471.54 | 17.12 | 20.14 | 20.88 | 24.94 |
| | 0.44 | 0.60 | 3.07 | 2.71 | 1.35 | 1.51 | 66.09 | 59.54 | 2.28 | 3.26 | 4.42 | 4.75 |
| DHEA 1.8% | 4.23 | 5.93 | 14.99 | 19.33 | 10.61 | 11.94 | 510.77 | 617.73 | 20.36 | 26.02 | 22.00 | 32.23 |
| | 0.76 | 1.11 | 2.62 | 3.59 | 0.63 | 0.81 | 52.78 | 69.01 | 2.31 | 3.38 | 2.68 | 4.35 |

[a]Data from one patient were excluded

TABLE 2

Average Serum Steroid Levels of DHEA and Eleven of its Metabolites on Day 1 and 7 of Daily Administration
of Intravaginal DHEA Suppositories to 40-75 Year-Old Postmenopausal Women with Vaginal Atrophy.
The values were obtained by dividing the AUC 0-24 h values measured on days 1 and 7 by 24 thus yielding the
average serum concentration of each steroid over a 24-h period. Serum steroid concentrations measured in
30-35 year-old premenopausal women are added as reference.

| | | DHEA | | 5-DIOL | | TESTO | | DHT | | E1 | | E2 | |
|---|---|---|---|---|---|---|---|---|---|---|---|---|---|
| GROUP | VALUE | DAY 1 ng/mL | DAY 7 ng/mL | DAY 1 ng/mL | DAY 7 ng/mL | DAY 1 ng/mL | DAY 7 ng/mL | DAY 1 ng/mL | DAY 7 ng/mL | DAY 1 pg/mL | DAY 7 pg/mL | DAY 1 pg/mL | DAY 7 pg/mL |
| PLACEBO | MEAN | 1.02 | 1.03 | 0.23 | 0.23 | 0.11[a] | 0.11 | 0.026 | 0.024 | 12.73 | 12.58 | 2.90 | 2.77 |
| | SEM | 0.20 | 0.20 | 0.02 | 0.02 | 0.01 | 0.01 | 0.003 | 0.003 | 1.44 | 1.41 | 0.32 | 0.29 |
| DHEA 0.5% | MEAN | 2.73 | 2.34 | 0.45 | 0.41 | 0.12 | 0.12 | 0.038 | 0.039 | 14.02 | 15.40 | 3.66 | 4.04 |
| | SEM | 0.33 | 0.37 | 0.04 | 0.05 | 0.01 | 0.01 | 0.004 | 0.004 | 1.58 | 2.04 | 0.47 | 0.69 |
| DHEA 1.0% | MEAN | 3.12 | 3.18 | 0.50 | 0.58 | 0.16 | 0.19 | 0.046 | 0.055 | 17.42 | 24.11 | 4.23 | 6.01 |
| | SEM | 0.28 | 0.43 | 0.07 | 0.08 | 0.03 | 0.04 | 0.010 | 0.011 | 2.95 | 3.54 | 0.96 | 1.31 |
| DHEA 1.8% | MEAN | 5.15 | 4.76 | 0.79 | 0.88 | 0.21 | 0.25 | 0.068 | 0.081 | 18.07 | 25.04 | 3.74 | 5.68 |
| | SEM | 0.39 | 0.42 | 0.04 | 0.07 | 0.03 | 0.03 | 0.008 | 0.010 | 1.57 | 2.85 | 0.49 | 0.84 |
| 30-35 YEAR-OLD | MEAN | 4.47 | | 0.49 | | 0.18 | | 0.07 | | 53.96 | | 82.05 | |
| PRE- | SD | 2.19 | | 0.20 | | 0.07 | | 0.03 | | 23.28 | | 42.19 | |
| MENOPAUSAL | Median | 4.14 | | 0.44 | | 0.17 | | 0.07 | | 49.47 | | 71.38 | |
| WOMEN | 5th-95th | 1.53-9.14 | | 0.25-0.84 | | 0.06-0.31 | | 0.03-0.14 | | 23.74-87.46 | | 22.00-159.97 | |
| (n = 47) | centiles | | | | | | | | | | | | |
| | (MIN-MAX) | (1.41-10.37) | | (0.25-0.96) | | (0.05-0.32) | | (0.03-0.17) | | (18.27-123.60) | | (17.71-181.14) | |

| | | E1-S | | DHEA-S | | 4-DIONE | | ADT-G | | 3α-DIOL-3G | | 3α-DIOL-17G | |
|---|---|---|---|---|---|---|---|---|---|---|---|---|---|
| GROUP | VALUE | DAY 1 ng/mL | DAY 7 ng/mL | DAY 1 μg/mL | DAY 7 μg/mL | DAY 1 ng/mL | DAY 7 ng/mL | DAY 1 ng/mL | DAY 7 ng/mL | DAY 1 ng/mL | DAY 7 ng/mL | DAY 1 ng/mL | DAY 7 ng/mL |
| PLACEBO | MEAN | 0.13 | 0.12 | 0.36 | 0.35 | 0.26 | 0.26 | 7.36 | 6.97 | 0.50 | 0.50 | 0.52 | 0.51 |
| | SEM | 0.03 | 0.02 | 0.10 | 0.09 | 0.03 | 0.03 | 1.29 | 1.20 | 0.00 | 0.00 | 0.02 | 0.01 |
| DHEA 0.5% | MEAN | 0.13 | 0.13 | 0.57 | 0.55 | 0.38 | 0.36 | 19.75 | 19.21 | 0.67 | 0.70 | 1.03 | 1.11 |
| | SEM | 0.02 | 0.03 | 0.14 | 0.13 | 0.04 | 0.03 | 5.29 | 3.99 | 0.08 | 0.08 | 0.20 | 0.21 |
| DHEA 1.0% | MEAN | 0.13 | 0.18 | 0.60 | 0.69 | 0.43 | 0.46 | 17.41 | 19.65 | 0.71 | 0.84 | 0.87 | 1.04 |
| | SEM | 0.02 | 0.03 | 0.13 | 0.11 | 0.06 | 0.06 | 2.75 | 2.48 | 0.10 | 0.14 | 0.18 | 0.20 |
| DHEA 1.8% | MEAN | 0.18 | 0.25 | 0.62 | 0.81 | 0.44 | 0.50 | 21.28 | 25.74 | 0.85 | 1.08 | 0.92 | 1.34 |
| | SEM | 0.03 | 0.05 | 0.11 | 0.15 | 0.03 | 0.03 | 2.20 | 2.88 | 0.10 | 0.14 | 0.11 | 0.18 |
| 30-35 YEAR-OLD | MEAN | 1.19 | | 1.27 | | 0.96 | | 40.21 | | 1.21 | | 1.43 | |
| PRE- | SD | 0.93 | | 0.62 | | 0.35 | | 29.31 | | 0.83 | | 0.93 | |
| MENOPAUSAL | Median | 0.87 | | 1.04 | | 0.92 | | 31.62 | | 1.06 | | 1.35 | |
| WOMEN | 5th-95th | 0.31-3.50 | | 0.56-2.65 | | 0.45-1.64 | | 12.17-118.2 | | 0.25-2.78 | | 0.25-2.56 | |
| (n = 47) | centiles | | | | | | | | | | | | |
| | (MIN-MAX) | (0.21-4.40) | | (0.45-2.71) | | (0.31-1.77) | | (6.86-132.6) | | (0.25-4.33) | | (0.25-5.71) | |

[a]One patient excluded from the group.
(Labrie, Bélanger et al. 2006).

It should be mentioned, however, as shown in Table 3, that there was a strong tendency for lower pre-treatment values of many steroids in the placebo group. This is related to particularly low values in the placebo group for DHEA, DHEA-S, 4-dione, Testo, DHT, $E_2$, ADT-G and 3α-diol-17G. Since all the average serum steroid values observed after administration of the 0.5% and 1.0% doses of DHEA remain within or well below the values found in normal premenopausal women, no attempt was made to correct this apparent bias. It is of interest to mention that the average 24 h serum levels of all steroids measured on day 7 of daily administration of a 0.5% DHEA suppository correspond almost exactly to the values measured in normal 55- to 65-year-old women while the 1.0% DHEA suppository leads to values within the range observed in 55- to 65-year old normal women (Labrie, Bélanger et al. 2006).

Since the androgen metabolites are the most reliable measure of transformation of exogenous DHEA into active androgens, the present data indicate that even the highest dose of DHEA used in the present study meet the FDA requirements of serum steroid levels which remain within the normal range found in normal premenopausal women.

TABLE 3

Basal Serum Steroid Levels on Days 1 and 7 of Daily Administration of Intravaginal Increasing Doses of DHEA Data are Expressed in ng/ml Except for $E_1$ and $E_2$ (pg/ml) and DHEA-S (µg/ml).

| Steroid | | Placebo | DHEA 0.5% | DHEA 1.0% | DHEA 1.8% |
|---|---|---|---|---|---|
| DHEA | Day 1 | 0.72 ± 0.14 | 1.09 ± 0.24 | 0.94 ± 0.19 | 0.99 ± 0.15 |
| | Day 7 | 0.69 ± 0.14 | 1.29 ± 0.26 | 1.43 ± 0.19 | 1.83 ± 0.13 |
| 5-diol | Day 1 | 0.22 ± 0.02 | 0.26 ± 0.03 | 0.26 ± 0.05 | 0.25 ± 0.02 |
| | Day 7 | 0.22 ± 0.02 | 0.31 ± 0.05 | 0.36 ± 0.05 | 0.46 ± 0.04 |
| DHEA-S | Day 1 | 0.372 ± 0.102 | 0.543 ± 0.157 | 0.572 ± 0.144 | 0.447 ± 0.094 |
| | Day 7 | 0.368 ± 0.100 | 0.592 ± 0.160 | 0.717 ± 0.125 | 0.805 ± 0.143 |
| 4-dione | Day 1 | 0.18 ± 0.02 | 0.21 ± 0.03 | 0.23 ± 0.04 | 0.22 ± 0.03 |
| | Day 7 | 0.16 ± 0.02 | 0.25 ± 0.03 | 0.34 ± 0.06 | 0.38 ± 0.03 |
| Testo | Day 1 | 0.10 ± 0.01 | 0.09 ± 0.01 | 0.12 ± 0.03 | 0.15 ± 0.03 |
| | Day 7 | 0.09 ± 0.01 | 0.10 ± 0.01 | 0.18 ± 0.03 | 0.23 ± 0.03 |
| DHT | Day 1 | 0.024 ± 0.003 | 0.026 ± 0.003 | 0.037 ± 0.010 | 0.029 ± 0.002 |
| | Day 7 | 0.023 ± 0.002 | 0.035 ± 0.004 | 0.047 ± 0.010 | 0.062 ± 0.006 |
| $E_1$ | Day 1 | 11.98 ± 1.65 | 11.83 ± 1.28 | 14.72 ± 2.79 | 13.59 ± 1.88 |
| | Day 7 | 11.71 ± 1.19 | 13.53 ± 1.66 | 22.15 ± 3.21 | 23.77 ± 3.35 |
| $E_2$ | Day 1 | 3.00 ± 0.44 | 3.13 ± 0.37 | 4.30 ± 1.38 | 3.42 ± 0.62 |
| | Day 7 | 2.75 ± 0.28 | 3.94 ± 0.65 | 5.98 ± 1.26 | 6.00 ± 1.10 |
| $E_1$-S | Day 1 | 0.137 ± 0.024 | 0.133 ± 0.029 | 0.117 ± 0.016 | 0.164 ± 0.033 |
| | Day 7 | 0.143 ± 0.025 | 0.151 ± 0.034 | 0.203 ± 0.016 | 0.259 ± 0.049 |
| ADT-G | Day 1 | 7.42 ± 1.48 | 13.65 ± 3.71 | 11.49 ± 2.10 | 9.44 ± 1.23 |
| | Day 7 | 6.72 ± 1.17 | 17.02 ± 4.39 | 16.34 ± 2.30 | 19.26 ± 1.96 |
| 3α-diol-3G | Day 1 | 0.50[a] | 0.61 ± 0.07 | 0.71 ± 0.14 | 0.58 ± 0.05 |
| | Day 7 | 0.50[a] | 0.75 ± 0.11 | 0.96 ± 0.25 | 0.96 ± 0.15 |
| 3α-diol-17G | Day 1 | 0.50[a] | 0.84 ± 0.16 | 0.85 ± 0.22 | 0.65 ± 0.06 |
| | Day 7 | 0.50[a] | 0.95 ± 0.16 | 1.18 ± 0.30 | 1.27 ± 0.19 |

[a]Steroid levels are below the limit of quantification for all subjects (limit of quantification = 0.50 ng/mL).

Figure 10:
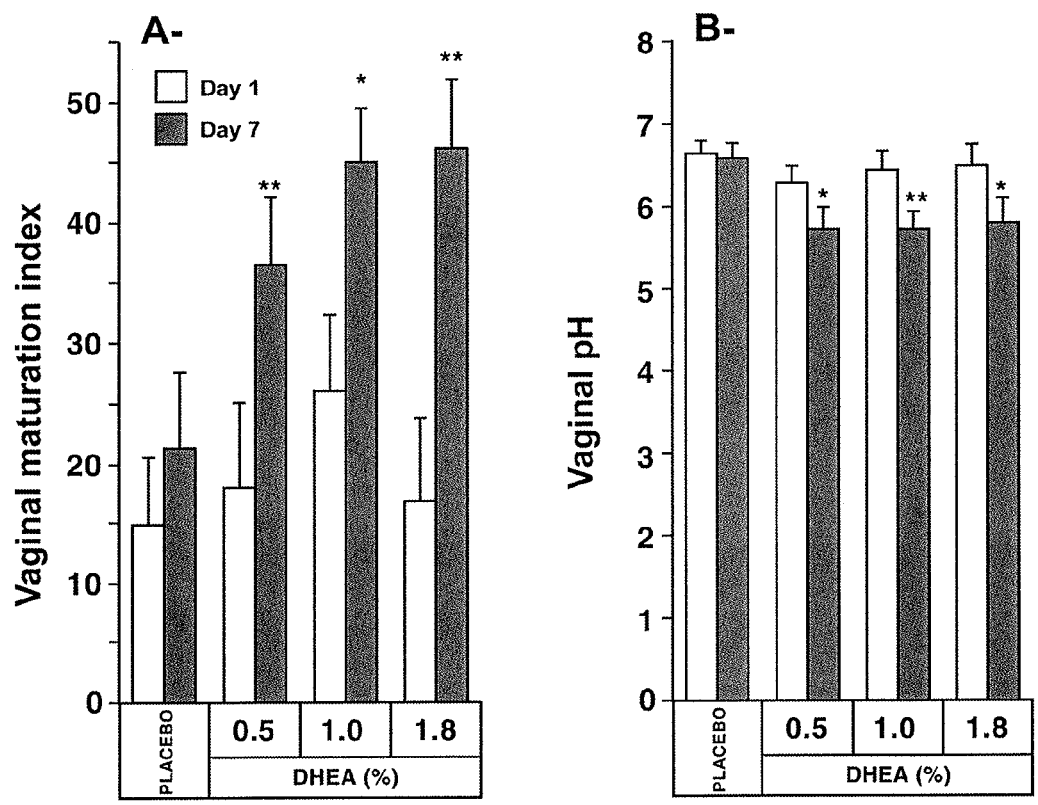
FIG. 10 shows Maturation Index (A) and Vaginal pH (B) Measured on Day 1 and Day 7 in 40-75 Year-Old Postmenopausal Women Following Daily Administration of Vaginal Suppositories Containing 0%, 0.5%, 1.0% or 1.8% of DHEA. Data are expressed as means±SEM (n=9 or 10). *, p<0.05, **, p<0.01, Data on Day 7 versus Data on Day 1.

After only one week of daily administration of the DHEA suppositories, the maturation index increased by 107% (p<0.01), 75% (p<0.05) and 150% (p<0.01) in the 0.5%, 1.0% and 1.8% DHEA groups, respectively (FIG. 10A). No change was observed in the placebo group between day 1 and day 7. Vaginal pH, on the other hand, decreased from 6.29±0.21 to 5.75±0.27 (p<0.05), 6.47±0.23 to 5.76±0.22 (p<0.01) and 6.53±0.25 to 5.86±0.28 (p<0.05), respectively in the 0.5%, 1.0% and 1.8% DHEA groups (FIG. 10B). No change of vaginal pH was observed in the placebo group.

Example 2

Bioavailability and Metabolism of Oral and Percutaneous Dehydroepiandrosterone in Postmenopausal Women 1. Introduction Humans, along with the other primates, are unique among animal species in having adrenals that secrete large amounts of the inactive precursor steroids DHEA and especially DHEA-S, which are converted into active androgens and/or estrogens in peripheral tissues (Labrie, 1991; Labrie, Bélanger et al., 1995; Labrie, Luu-The et al., 1997; Labrie, Simard et al., 1996; Labrie, Luu-The et al., 2005; Labrie, Poulin et al., 2006 and Simpson 2000). In fact, plasma DHEA-S levels in adult men and women are 100-500 times higher than those of testosterone and 1000-10,000 times higher than those of estradiol, thus providing a large reservoir of substrate for conversion into androgens and/or estrogens in the peripheral intracrine tissues which possess the enzymatic machinery necessary to transform DHEA into active sex steroids (Labrie 1991, and Labrie, Luu-The et al., 2005). In fact, the term intracrinology was first coined in 1988 (Labrie, Bélanger et al., 1988) to describe the synthesis of the active steroids made in the same cells where they exert their action with no or minimal release into the extracellular space and general circulation before being inactivated (Labrie, 1991).

The marked reduction in the formation of DHEA-S by the adrenals during aging (Bélanger et al., 1994; Vermeulen and Verdonck, 1976; and Migeon et al., 1957) results in a dramatic fall in the formation of androgens and estrogens in peripheral target tissues, a situation potentially associated with age-related diseases such as insulin resistance (Schriock et al. 1988 and Coleman et al. 1982) and obesity (Nestler et al. 1988; MacEwen and Kurman, 1991, and Tchernof et al. 1995).Moreover, much attention has been given to the benefits of DHEA administered to postmenopausal women, especially on the bone, skin, vaginum, glucose and insulin metabolism, fat mass, as well as well-being after oral (Villareal and Holloszy, 2004; Baulieu et al., 2000; Morales, et al. 1994; and Kawano et al. 2003) and percutaneous (Diamond et al., 1996 and Labrie Diamond et al. 1997) administration. It thus becomes of particular importance to obtain more precise knowledge about the bioavailability, pharmacokinetics and metabolism of DHEA following these two routes of administration.

Since we have already shown, using a pharmacological dose of DHEA administered percutaneously for 2 weeks, that measurements of serum testosterone (testo) and estradiol ($E_2$) levels do not provide a reliable assessment of the true intracellular pool of androgens and estrogens (Labrie, Bélanger et al., 1997; Labrie, Bélanger et al., 2006 and Labrie, Bélanger, et al, 2007b) we have compared the serum levels of DHEA and nine steroids known to be most closely associated with active androgens and estrogens and their metabolites. A detailed analysis of the 24 h changes of serum steroid levels was performed on the first day and after 2 weeks of daily administration of DHEA by the oral route as well as percutaneously using a DHEA cream or gel.

2. Subjects and Methods

Thirty-six healthy 60-70-year-old postmenopausal women participated in the study after IRB approval and having given their written informed consent. Body weight was within ±20% of normal body weight according to Metropolitan Life Tables.

No subject suffered from a significant metabolic or endocrine disorder, coronarian disease or hypertension. No women had treatment with androgens or anabolic steroids within 6 months prior to the screening visit. All participants had a medical history, complete physical examination and serum biochemistry profile including lipids, complete blood count, urine analysis and detailed serum hormone determinations during the screening phase of the protocol.

3. Study Design, Treatment and Measurements

This study was a randomized open-label trial of 12 subjects per arm. After written informed consent was obtained and women were found eligible, each subject was randomized to receive DHEA by cream, gel or orally. Daily, before breakfast, for 14 days, subjects received, at the research clinic, either 4 g of 10% DHEA gel or 4 g of 10% DHEA cream applied on a total 30 cm×30 cm area of the thighs or two 50 mg capsules of DHEA orally before breakfast.

Blood sampling was performed at 08:00-09:00 h at screening and before application of DHEA, on the first day of dosing, as well as on days 2, 4, 7, 10 and 14. On the 1st and 14th days, blood samples were obtained at 0.5 h, 1 h, 1.5 h, 2 h, 3 h, 4 h, 5 h, 6 h, 7 h, 8 h, 12 h and 24 h following DHEA administration.

4. Serum Steroid Analysis

DHEA, DHEA-S, androst-5-ene-3β,17β-diol (5-diol), testosterone, androstenedione (4-dione), 17β-estradiol ($E_2$), estrone ($E_1$), estrone sulfate ($E_1$-S), androsterone glucuronide (ADT-G), and androstane-3*,17β-diol glucuronide (3 α-diol-G) were measured by gas chromatography/mass spectrometry (DHEA, 5-diol, 4-dione, testosterone, $E_1$ and $E_2$) using electron impact or chemical ionization and by liquid chromatography/tandem mass spectrometry using turboionspray (DHEA-S, ADT-G and 3 α-diol-G) as described (Labrie, Bélanger et al., 2006; Labrie, Bélanger, et al, 2007b and Swanson et al. 2007).

5. Calculations and Statistical Analysis

On days 1 and 14, the area under the curve of the serum concentration of each steroid was measured between 0 h and 24 h ($AUC_{0-24\,h}$). The areas under the curves were calculated by a linear trapezoidal method (model-independent). The relative bioavailability of the DHEA gel, DHEA cream and DHEA capsules was based on the mean difference in the log-transformed AUC values. All calculations were performed with the SAS software (SAS Institute, Cary, N.C., USA).

6. Results

Figure 11:
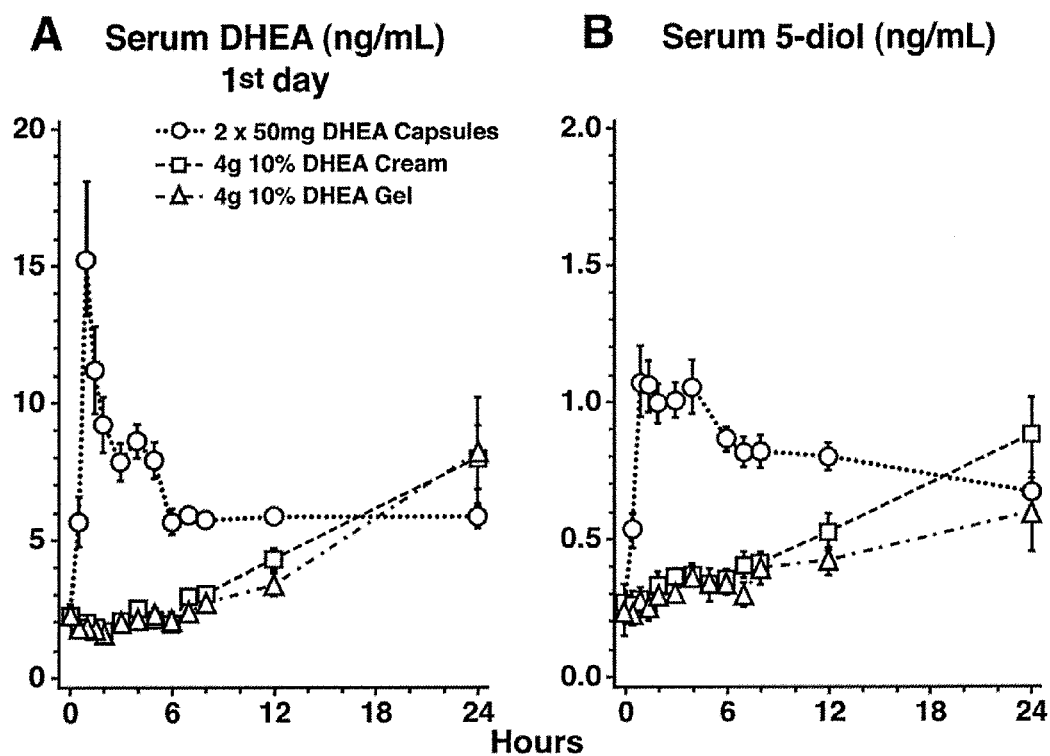
FIG. 11 shows a time-course of serum dehydroepiandrosterone (DHEA) (A) and androst-5-ene-3β,17β-diol (5-diol) (B) following single oral administration of two 50-mg capsules of DHEA or the application of 4 g of 10% DHEA cream or gel to postmenopausal women.

The oral administration of two capsules of 50 mg of DHEA led to an increase of serum DHEA from 2.3±0.3 ng/ml to a maximal value of 15.6±2.5 ng/ml at 1 h with a progressive decrease thereafter to 5.7±0.5 ng/ml at 6 h followed by a plateau up to 24 h (FIG. 11A). When 4 g of a 10% DHEA gel or cream were applied on a 30 cm×30 cm area of the skin of the thighs, serum DHEA levels only started to increase at 12 h to reach values of 8.2±2.0 and 8.0±1.2 nmol/l, respectively, at 24 h (FIG. 11A). There was no significant difference between the cream or gel in the serum levels of DHEA at any of the time intervals studied up to 24 h after first application of the precursor steroid on the skin.

When serum 5-diol was measured after oral first administration of DHEA, the concentration of 5-diol increased from a pretreatment concentration of 0.31±0.03 ng/ml to a maximal value of 1.19±0.13 ng/ml at 1 h with a slow and progressive decrease thereafter to reach 0.79±0.05 ng/ml at 24 h (FIG. 11B). It can be seen in the same figure that the serum levels of 5-diol increased much more slowly after administration of DHEA percutaneously by cream or gel to reach the first statistically significant different values of 1.00±0.14 ng/ml for the cream and 0.72±0.14 ng/ml for the gel at 24 h.

Figure 12:
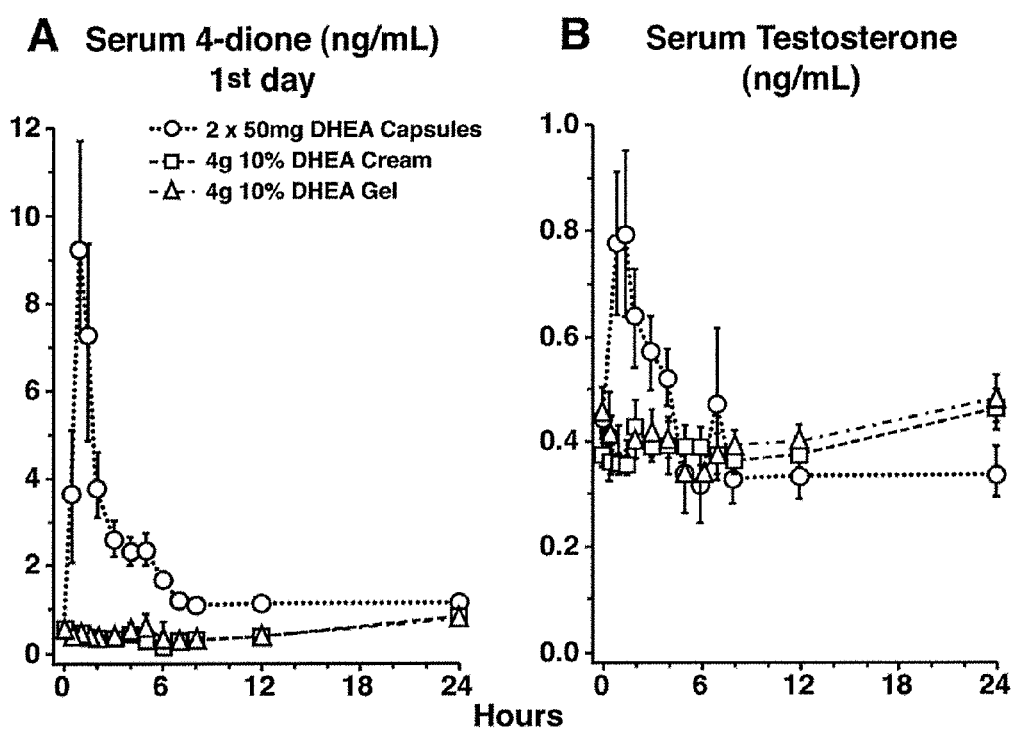
FIG. 12 shows a time-course of serum androstenedione (4-dione) (A) and testosterone (B) following single oral administration of two 50-mg capsules of DHEA or the application of 4 g of 10% DHEA cream or gel to postmenopausal women.

Following oral DHEA, serum 4-dione increased from 0.6±0.1 ng/ml to a maximal value of 9.5±2.2 ng/ml at 1 h followed by a rapid decrease thereafter to values which remained on a plateau of about 1.2 ng/ml between 8 h and 24 h (FIG. 12A). Following administration of DHEA by cream or gel, on the other hand, the first significant increase of serum 4-dione was only observed at 24 h at values of 0.9±0.1 and 0.8±0.1 ng/ml for the cream and gel, respectively.

Figure 13:
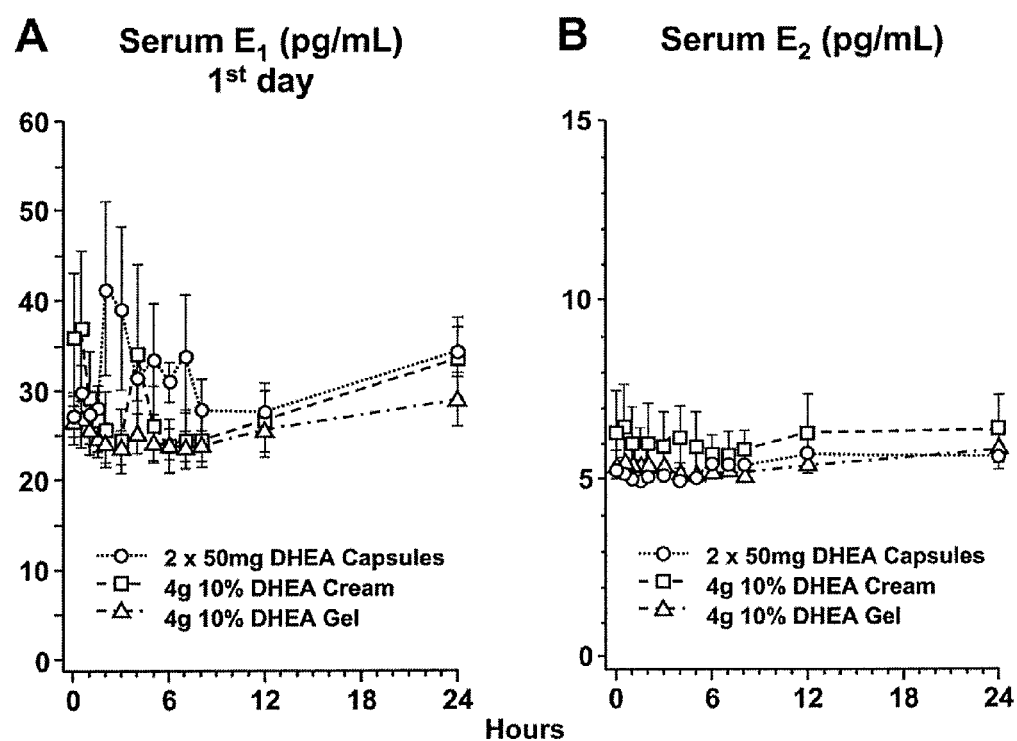
FIG. 13 shows a time-course of serum estrone ($E_1$) (A) and 17β-estradiol ($E_2$) (B) following single oral administration of two 50-mg capsules of DHEA or the application of 4 g of 10% DHEA cream or gel to postmenopausal women.

A comparable pattern was observed for serum testosterone. In fact, after oral administration of two 50 mg capsules of DHEA, serum testosterone increased from 0.38±0.03 ng/ml to a maximal value of 0.79±0.14 ng/ml at 1 h. This rise was followed by a rapid decrease to 0.30±0.08 ng/ml at 6 h followed by a plateau thereafter until 24 h (FIG. 12B). When DHEA was applied as cream or gel, the first increase was observed at 24 h at a value of approximately 0.45 ng/ml. As can be seen in FIGS. 13A and B, the first administration of DHEA by the oral or percutaneous route had no statistically significant effect on the serum levels of E1 or E2 during the first 24 h.

Figure 14:
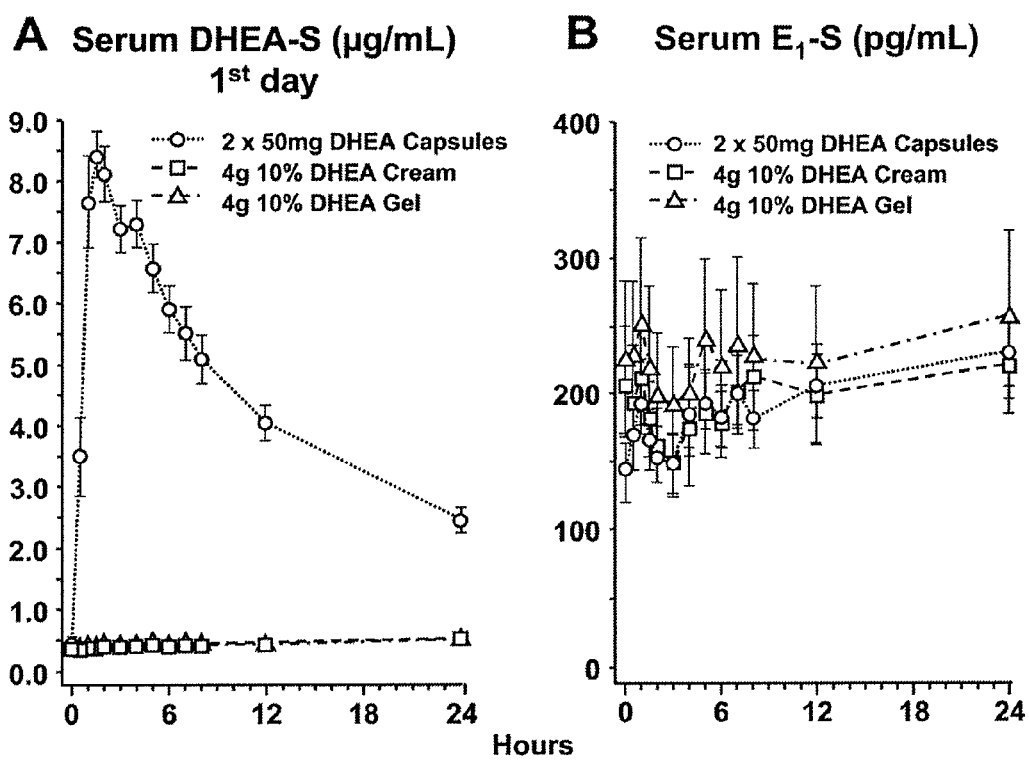
FIG. 14 shows a time-course of serum dehydroepiandrosterone sulfate (DHEA-S) (A) and estrone sulfate ($E_1$-S) (B) following single oral administration of two 50-mg capsules of DHEA or the application of 4 g of 10% DHEA cream or gel to postmenopausal women.
Figure 15:
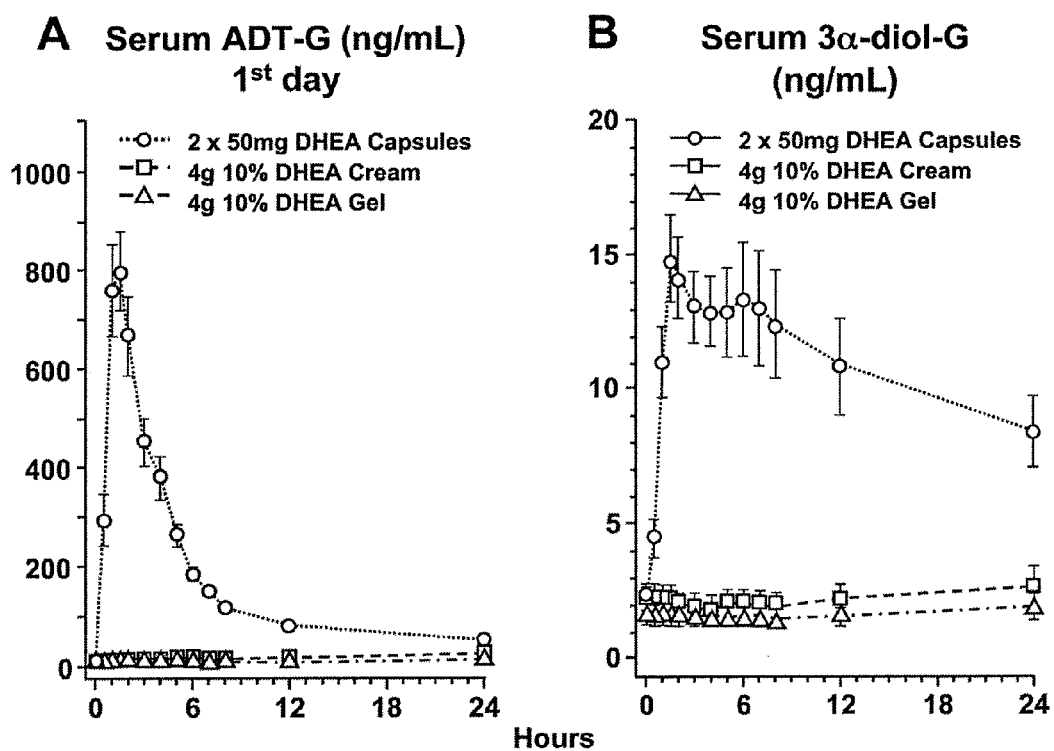
FIG. 15 shows a time-course of serum androsterone glucuronide (ADT-G) (A) and androstone 3α,17β-diol-glucuronide (3α-diol-G) (B) following daily oral administration of two 50-mg capsules of DHEA or the application of 4 g of 10% DHEA cream or gel to postmenopausal women.

Serum DHEA-S on the other hand followed a pattern similar, although slightly delayed, compared to DHEA and 5-diol following oral administration of two capsules of 50 mg DHEA (FIG. 14A). Thus, serum DHEA-S increased from 0.4±0.1 µg/ml to 7.7±1.0 µg/ml at 1 h to a maximal value of 8.4±0.6 µg/ml at 2 h with a progressive decrease to 2.7±0.3 µg/ml at 24 h. No significant change of serum DHEA-S was observed during the first 24 h after administration of DHEA in a cream or gel. Serum E1-S, on the other hand, did not change significantly during the first 24 h following the first Serum ADT-G, the main metabolite of androgens, increased from 14±3 ng/ml to 760±150 ng/ml at 1 h and 790±140 ng/ml at 2 h to then decrease progressively to 92±5 ng/ml at 12 h and 70±5 ng/ml at 24 h (FIG. 15A). Serum 3 α-diol-G, on the other hand, increased from 2.2±0.5 ng/ml to 14.5±2.0 ng/ml at 2 h (FIG. 15B). The decrease observed thereafter for 3 α-diol-G was however much slower than that of ADT-G, a decrease of only about 40% being observed between 2 h and 24 h after oral administration of DHEA. Following application of 4 g of 10% DHEA on the skin, there was no significant change of serum ADT-G or 3 α-diol-G up to 24 h (FIG. 15B).

Figure 16:
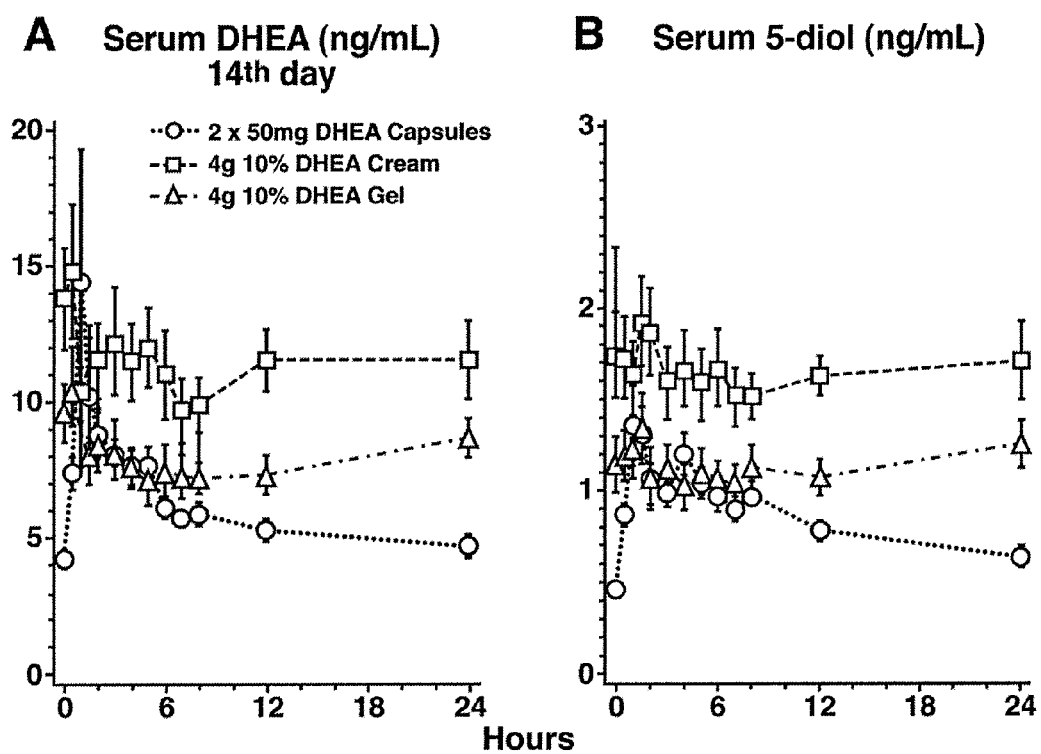
FIG. 16 shows a time-course of serum dehydroepiandrosterone (DHEA) (A) and andros-5-ene-3β,17β-diol (5-diol) (B) following daily oral administration of two 50-mg capsules of DHEA or the application of 4 g of 10% DHEA cream or gel to postmenopausal women. Measurements were made on the 14th day of dosing.

When the measurements of the same kinetic parameters were repeated on the 14th day of daily dosing, it could be seen that the administration of two capsules of 50 mg of DHEA led, from a predosing value of 4.2±0.4 ng/ml, to a maximal concentration of 14.8±4.4 ng DHEA/ml at 1 h followed by a progressive decrease thereafter to 4.5±0.4 ng/ml at 24 h (FIG. 16A). On the other hand, when DHEA was administered by cream or gel, no significant change was observed during the 24-h period and serum DHEA remained between 10 ng/ml and 15 ng/ml following application of the cream and between 7 ng/ml and 11 ng/ml following application of the gel.

Similarly, when serum 5-diol was measured on the 14th day of treatment, the serum concentration of this steroid increased from 0.46±0.04 ng/ml to 1.37±0.21 ng/ml at 1 h with a slow decrease thereafter to reach 0.64±0.06 ng/ml at 24 h (FIG. 16B). As observed for DHEA, serum 5-diol remained approximately constant during the 24-h period at about 1.5-1.9 ng/ml following application of the cream and 1.0-1.3 ng/ml following application of the gel.

Figure 17:
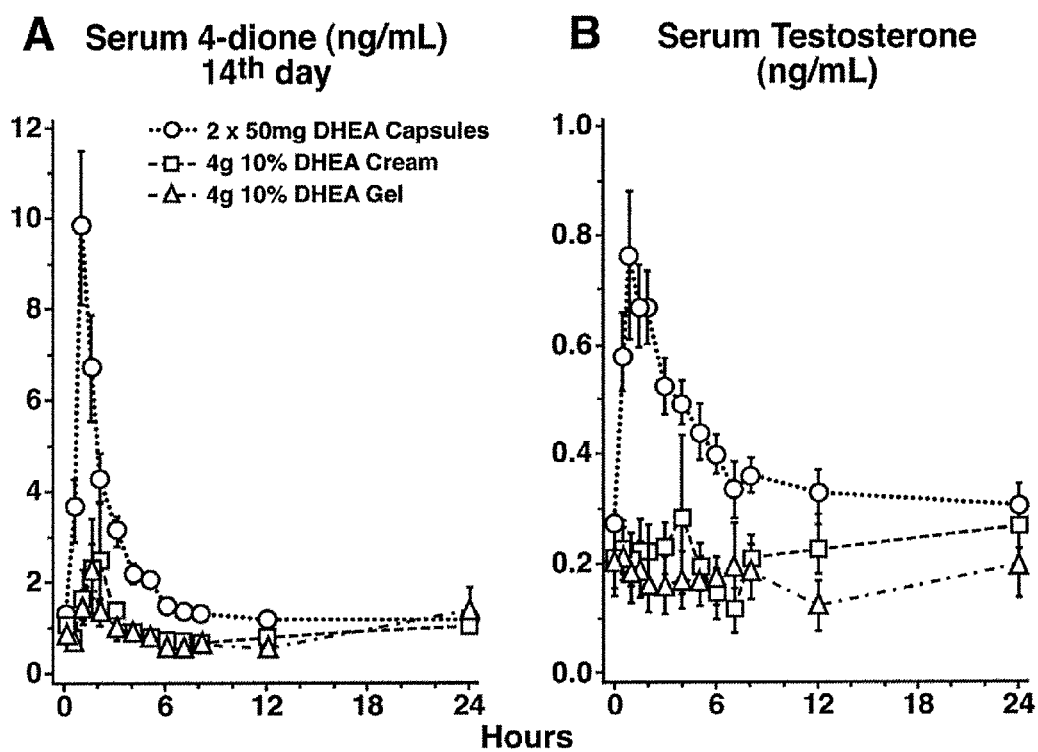
FIG. 17 shows a time-course of serum androstenedione (4-dione) (A) and testosterone (B) following daily oral administration of two 50-mg capsules of DHEA or the application of 4 g of 10% DHEA cream or gel to postmenopausal women. Measurements were made on the 14th day of dosing.

When serum 4-dione was measured on the 14th day of dosing, the serum concentration of this steroid increased from 1.3±0.2 ng/ml to a maximal value of 9.8±1.7 ng/ml at 1 h followed by a rapid decrease to 1.5±0.1 ng/ml at 6 h with a value of 1.2±0.1 ng/ml measured at 24 h (FIG. 17A). Following application of DHEA on the skin as a cream or gel, there was a non-significant increase of serum 4-dione to approximately 2.5 ng/ml at 2 h with values, thereafter, remaining on a plateau at 1.0-1.6 ng/ml up to 24 h (FIG. 17A).

Figure 18:
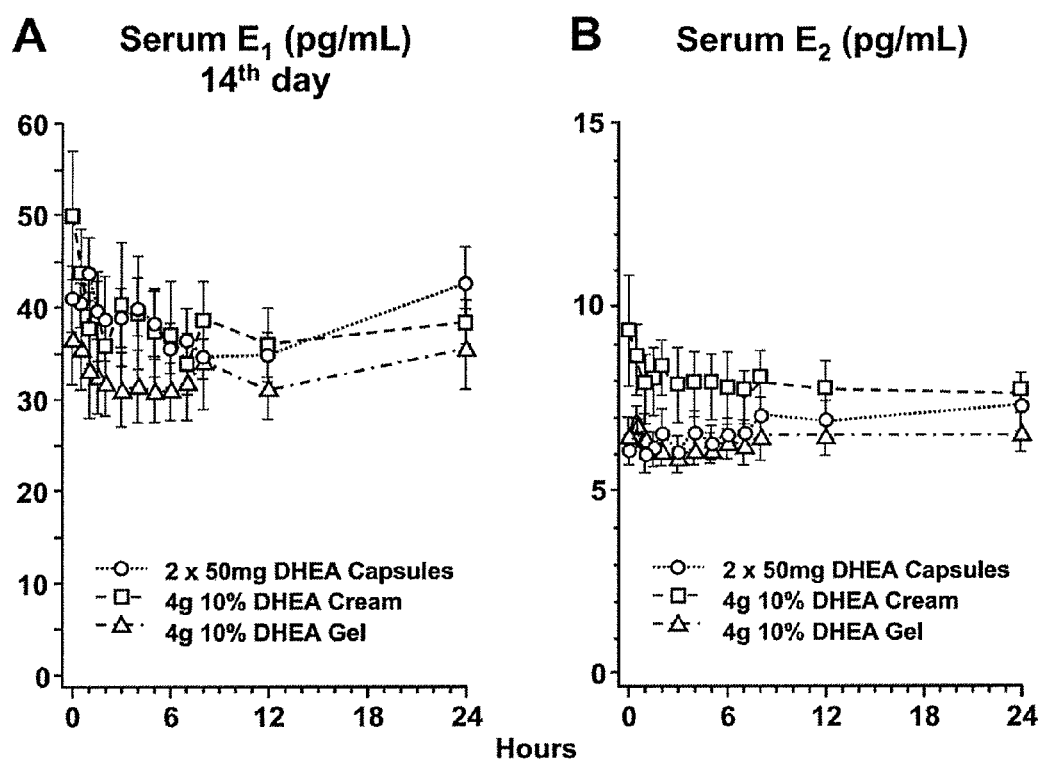
FIG. 18 shows a time-course of serum estrone ($E_1$) (A) and estradiol ($E_2$) following daily oral administration of two 50-mg capsules of DHEA or the application of 4 g of 10% DHEA cream or gel to postmenopausal women. Measurements were made on the 14th day of dosing.

Serum testosterone increased on the 14th day of dosing following oral administration of 100 mg of DHEA from 0.31±0.04 ng/ml to a maximal value of 0.83±0.11 ng/ml at 1 h followed by a progressive decrease to a value of 0.37±0.04 ng/ml at 24 h (FIG. 17B). Following DHEA application as a cream or a gel, serum levels of testosterone remained unchanged during the 24-h period at approximately 0.3 ng/ml, this value being not significantly different from pre-treatment. As observed on the first day, there was no significant change in the serum levels of E1 (FIG. 18A) or E2 (FIG. 18B) during the 24 h which followed the 14th daily administration of DHEA by the oral or percutaneous route.

Figure 19:
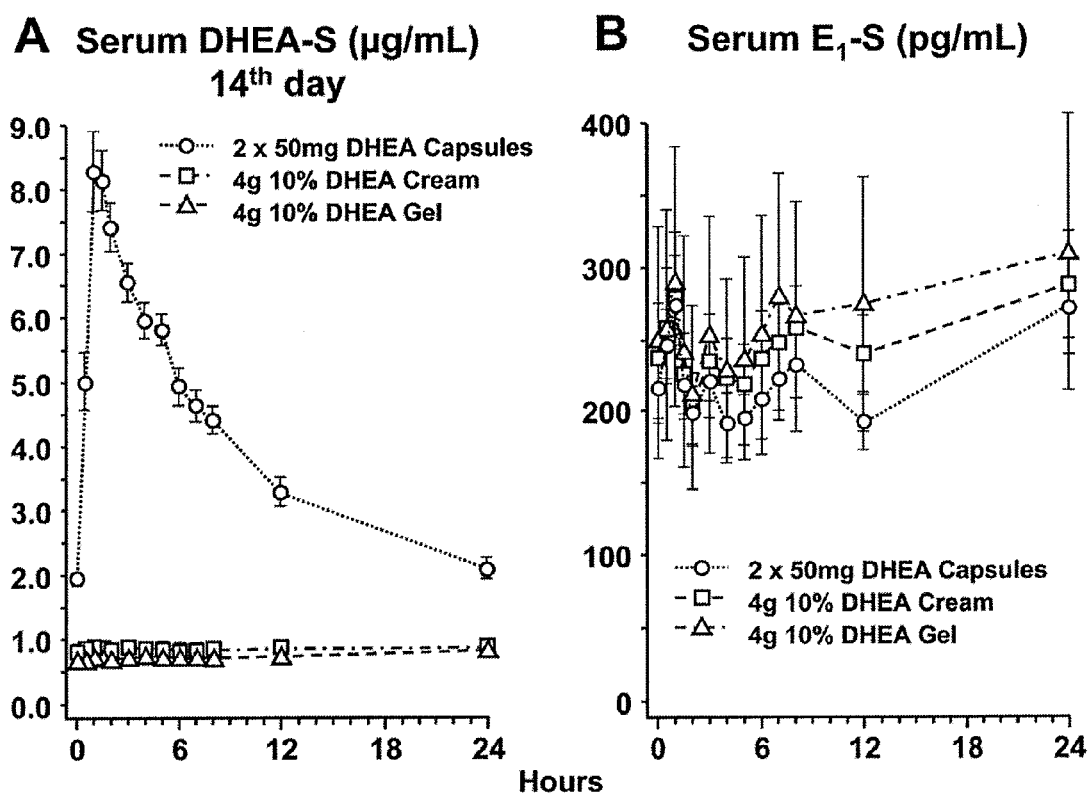
FIG. 19 shows a time-course of serum dehydroepiandrosterone sulfate (DHEA-S) (A) and estrone sulfate ($E_1$-S) (B) following daily oral administration of two 50-mg capsules of DHEA or the application of 4 g of 10% DHEA cream or gel to postmenopausal women. Measurements were made on the 14th day of dosing.

From a predosing level of 1.95±0.15 µg/ml, serum DHEA-S increased to 8.3±0.4 µg/ml at 1 h to decrease progressively to 2.6±0.3 µg/ml at 24 h (FIG. 19A). No significant change in serum DHEA-S was observed after application of DHEA on the skin. Serum $E_1$-S, on the other hand, did not change during the 24 h following the 14th daily administration of DHEA by the oral or percutaneous route (FIG. 19B).

Figure 20:
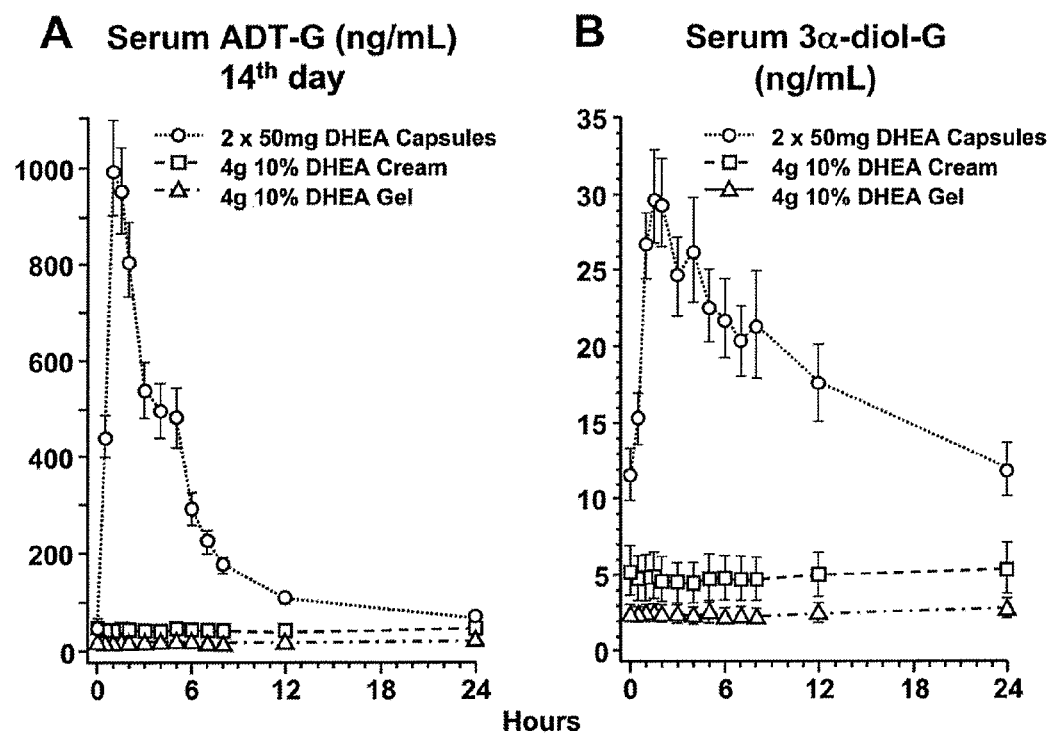
FIG. 20 shows a time-course of serum androsterone glucuronide (ADT-G) (A) and androstene-3α,17β-diol-G (3α-diol-G) (B) following daily oral administration of two 50-mg capsules of DHEA or the application of 4 g of 10% DHEA cream or gel to postmenopausal women. Measurements were made on the 14th day of dosing.

While starting at a higher level on day 14 than on day 1, serum ADT-G increased rapidly from 66±1 ng/ml to 996±105 ng/ml at 1 h to decrease progressively thereafter to 116 ng/ml at 12 h and 91±15 ng/ml at 24 h (FIG. 20A). No significant change in serum ADT-G levels occurred following the application of DHEA on the skin. Serum 3 α-diol-G, on the other hand, increased from 12±2.5 ng/ml to 29.4±5.5 ng/ml at 2 h to decrease slowly thereafter to reach 13±3.0 ng/ml at 24 h following 14th daily oral administration of 100 mg DHEA. No significant change was observed on serum 3 α-diol-G after percutaneous administration of DHEA (FIG. 20B).

In order to obtain a more precise measure of the accumulation of DHEA and its metabolites, we next compared the areas under the curves of the serum steroid concentrations ($AUC_{0-24 h}$ values) measured on the 1st and 14th days of dosing. As can be predicted from FIG. 11, FIG. 12, FIG. 13, FIG. 14, FIG. 15, FIG. 16, FIG. 17, FIG0.18, FIG0.19 and FIG. 20, the $AUC_{0-24 h}$ values of all steroids, except the metabolites of estrogens ($E_1$-5) and androgens (ADT-G and 3 α-diol-G), due to some accumulation of these steroids, are similar on the 1st and 14th days of administration of DHEA by the oral route (Table 4). Following percutaneous administration of DHEA, on the other hand, due to the slower absorption of DHEA following administration in a cream or gel, 155% and 86% higher values of the DHEA $AUC_{0-24 h}$ values are observed on the 14th day compared to the first day of dosing, respectively. Higher values are also observed for all the other steroids, except for $E_1$, $E_2$ and testosterone which showed no

TABLE 4

$AUC_{0-24 h}$ values measured on the 1st and 14th days of dosing as well as their ratio

| Steroid | DHEA (ng h/ml) | 5-Diol (ng h/ml) | 4-Dione (ng h/ml) | Testosterone (ng h/ml) | E1 (pg h/ml) | E2 (pg h/ml) | DHEA-S (µg h/ml) | E1-S (pg h/ml) | ADT-G (ng h/ml) | 3α-Diol-G (ng h/ml) |
|---|---|---|---|---|---|---|---|---|---|---|
| 2 × 50 mg capsules | | | | | | | | | | |
| 1st dosing | 153 (19) | 19.0 (20) | 40.2 (39) | 9.47 (31) | 745 (30) | 136 (20) | 108 (20) | 4.81 (39) | 4112 (24) | 259 (44) |
| 14th dosing | 144 (26) | 20.4 (25) | 43.6 (27) | 9.72 (23) | 910 (23) | 165 (25) | 95.0 (16) | 7.44 (36) | 5607 (28) | 453 (41) |
| 14th/1st | 0.94 | 1.07 | 1.08 | 1.03 | 1.22 | 1.21 | 0.88 | 1.55 | 1.36 | 1.75 |
| 4 g 10% cream | | | | | | | | | | |
| 1st dosing | 107 (33) | 13.7 (31) | 12.3 (43) | 8.35 (16) | 680 (48) | 147 (50) | 10.7 (45) | 4.83 (58) | 404 (62) | 50.6 (93) |
| 14th dosing | 273 (36) | 39.7 (31) | 22.8 (33) | 8.77 (16) | 847 (22) | 175 (27) | 19.9 (34) | 7.96 (39) | 977 (66) | 114 (104) |
| 14th/1st | 2.55 | 2.90 | 1.85 | 1.00 | 1.24 | 1.19 | 1.86 | 1.65 | 2.42 | 2.25 |
| 4 g 10% gel | | | | | | | | | | |
| 1st dosing | 101 (49) | 10.3 (55) | 13.3 (45) | 8.76 (11) | 620 (31) | 214 (137) | 11.2 (35) | 5.53 (84) | 254 (30) | 38.3 (86) |
| 14th dosi | 188 (30) | 27.2 (32) | 21.3 (51) | 8.04 (22) | 785 (40) | 152 (24) | 18.6 (34) | 9.11 (106) | 455 (23) | 60.3 (85) |
| 14th/1st | 1.86 | 2.64 | 1.60 | 0.96 | 1.27 | 0.71 | 1.66 | 1.65 | 1.79 | 1.57 |

Values within parenthesis represent % coefficient of variation. DHEA was administered by the oral route (2 × 50 mg capsules) or following application on the skin of 4 g of 10% DHEA cream or 4 g of 10% gel.

Figure 21:
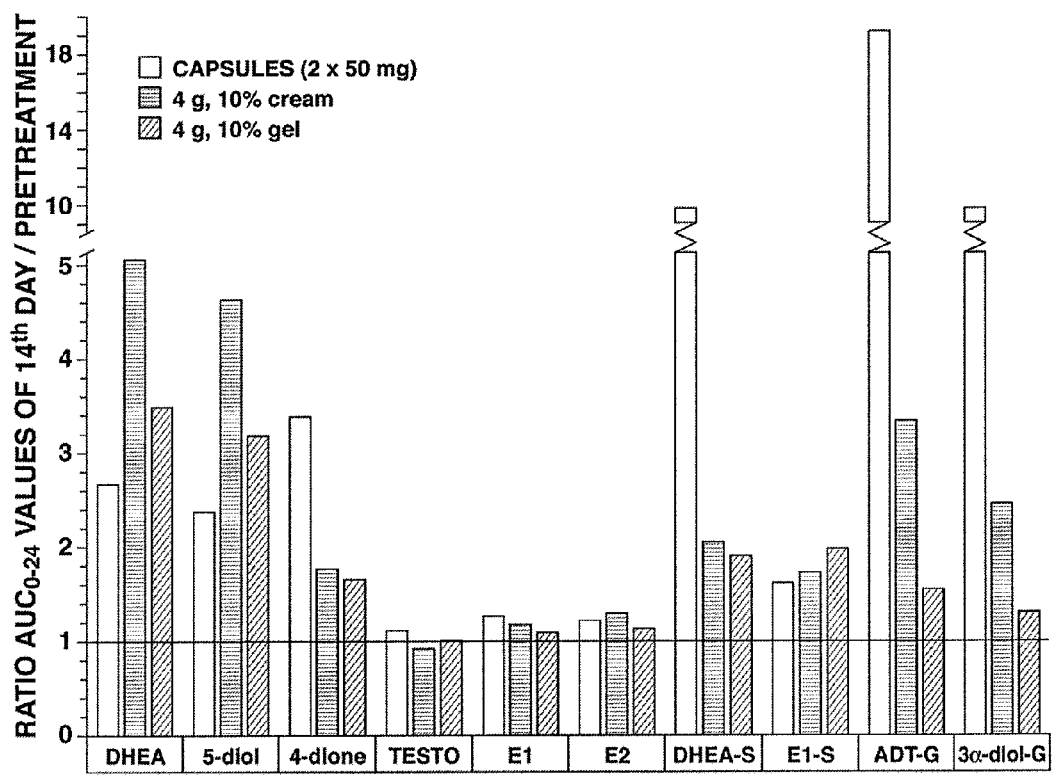
FIG. 21 shows ratios of the $AUC_{0-24\,h}$ values of DHEA and its metabolites on the 14th day of dosing compared to the pretreatment basal values. The corresponding numerical values can be found in Table 5.

As can be clearly seen in Table 5 and FIG. 21, there was no significant change in the serum $E_1$, $E_2$ or testosterone $AUC_{0-24 h}$ values measured on the 14th day of dosing compared to the predosing levels. Significant increases, however, were observed for all two other steroids. Thus, following daily oral dosing with 100 mg DHEA for 2 weeks, the area under the concentration curve of DHEA measured during the 24 h following administration of the steroid increased 167% over the pretreatment value while for 5-diol, 4-dione, DHEA-S, $E_1$-S, ADT-G and 3 α-diol-G, respective increases of 138%, 238%, 873%, 60%, 1820% and 874% were observed.

TABLE 5

Pretreatment and 14th day $AUC_{0-24\,h}$ values of DHEA and its metabolites

| Steroid | DHEA (ng h/ml) | 5-Diol (ng h/ml) | 4-Dione (ng h/ml) | Testosterone (ng h/ml) | E1 (pg h/ml) | E2 (pg h/ml) | DHEA-S (µg h/ml) | E1-S (pg h/ml) | ADT-G (ng h/ml) | 3α-Diol-G (ng h/ml) |
|---|---|---|---|---|---|---|---|---|---|---|
| Basal (pretreatment) | 53.9 | 8.56 | 12.9 | 8.72 | 717 | 135 | 9.76 | 4.64 | 292 | 46.6 |
| (A) 2 × 50 mg capsules | | | | | | | | | | |
| 14th day | 144 | 20.4 | 43.6 | 9.72 | 910 | 165 | 95.0 | 7.44 | 5607 | 453 |
| 14th/basal | 2.67 | 2.38 | 3.38 | 1.11 | 1.27 | 1.22 | 9.73 | 1.60 | 19.2 | 9.74 |
| (B) 4 g 10% cream | | | | | | | | | | |
| 14th day | 273 | 39.7 | 22.8 | 8.77 | 847 | 175 | 19.9 | 7.96 | 977 | 114 |
| 14th/basal | 5.06 | 4.63 | 1.77 | 1.01 | 1.18 | 1.30 | 2.04 | 1.72 | 3.34 | 2.45 |
| (C) 4 g 10% gel | | | | | | | | | | |
| 14th day | 188 | 27.2 | 21.3 | 8.04 | 785 | 152 | 18.6 | 9.11 | 455 | 60.3 |
| 14th/basal | 3.49 | 3.18 | 1.65 | 092 | 1.09 | 1.13 | 1.91 | 1.96 | 1.56 | 1.30 |

DHEA was administered by the oral route or percutaneously by cream or gel. Basal $AUC_{0-24\,h}$ values were calculated by multiplying the pretreatment basal serum steroid levels including screening by 24 h.

Except for DHEA and 5-diol, lower increases were observed following administration of DHEA cream or gel. In fact, following application of the DHEA cream, the DHEA-S $AUC_{0-24\,h}$ value increased by only 104% while the 4-dione, $E_1$-S, ADT-G and 3 α-diol-G $AUC_{0-24\,h}$ values increased by 77%, 72%, 234% and 145% over control, respectively. The AUC values for DHEA and 5-diol, on the other hand, increased by 406% and 363%, respectively (Table 5, FIG. 21). Comparable but somewhat lower increases were observed with the DHEA gel where the serum 4-dione, DHEA-S, $E_1$-S, ADT-G and 3 α-diol-G $AUC_{0-24\,h}$ values increased by 65%, 91%, 96%, 56% and 30% over control while the $AUC_{0-24\,h}$ values for DHEA and 5-diol increased by 249% and 238%, respectively.

Our recent findings (Labrie, Bélanger et al., 2007b) have shown that the serum DHEA changes observed following exogenous DHEA administration are at least a 100% overestimate of the true changes in sex steroid formation. In support of these data, FIG. 21 shows that following DHEA administration by cream or gel, the changes in serum DHEA are a marked overestimate of the changes in serum levels of all the steroids measured except for 5-diol, the immediate metabolite of DHEA. For the DHEA cream, the changes in the $AUC_{0-24\,h}$ values of serum 4-dione, DHEA-S, E1-S, ADT-G and 3 α-diol-G are only 77%, 104%, 72%, 234% and 145% compared to the 406% increase over pretreatment levels observed for serum DHEA.

For the androgens, it is now well established that uridine glucuronosyl transferase 2B7 (UGT 2B7), UGT 2B15 and UGT 2B17 are the three enzymes responsible for the glucuronidation of all androgens and their metabolites in the human (Bélanger et al. 2003). This recent completion of the identification and characterization of all the human UDT-glucuronosyl transferases makes possible the use of the glucuronide derivatives of androgens as markers of total androgenic activity in both women and men (Labrie, Bélanger et al., 2006; Labrie, Bélanger, et al, 2007b and Swanson et al. 2007). Accordingly, since all androgens are metabolized into ADT-G and 3 α-diol-G, the estimate of the percentage of efficacy of percutaneous DHEA for transformation into active androgens is thus estimated at 52% when adding the changes in ADT-G and 3α-δtoλ-Γ (a weighted 211% value compared to the DHEA changes of 406%). Similarly, following DHEA gel administration, the 249% increase in serum DHEA translates into only 65%, 91%, 96%, 56% and 30% increases in the $AUC_{0-24\,h}$ values of serum 4-dione, DHEA-S, E1-S1, ADT-G and 3 α-diol-G, respectively.

Since the high level of glucuronidation in the intestine and liver explains the high serum level of ADT-G and 3α-diol-G (Bélanger et al. 2003) following oral administration of DHEA, the relatively small increase in serum E1-S (60%) compared to the 167% increase in serum DHEA after oral DHEA indicates a 36% relative efficacy of transformation into estrogens. As shown earlier (Labrie, Bélanger et al., 1997; Labrie, Bélanger et al., 2006; Labrie, Bélanger, et al, 2007b), the present data indicate that DHEA administrated to postmenopausal women is predominantly transformed into androgens rather than into estrogens.

Discussion

The present data clearly show that during chronic treatment with DHEA by cream or gel, the concentration of all the steroids rapidly reaches a plateau with no detectable change in the serum concentration of any of the steroids measured during daily application of DHEA on the skin. Accordingly, from 24 h after first administration of DHEA percutaneously, the concentration of all steroids remains at the same level, thus showing that daily application of DHEA on the skin maintains constant serum levels of DHEA and all its metabolites. In postmenopausal women, it is already known that the circadian variation of serum DHEA is relatively small compared to the situation in normally cycling premenopausal women (Lui and Laughlin, 1990).

The present data also show that following daily oral administration of DHEA, there is no significant accumulation of DHEA or of its metabolites. Moreover, the metabolism of DHEA following its administration by the oral or percutaneous route is quantitatively similar, the quantitative differences being explained by the entero-hepatic metabolism following oral administration.

The higher $AUC_{0-24\,h}$ values of serum DHEA-S, ADT-G and 3 α-diol-G combined with the lower $AUC_{0-24\,h}$ values of DHEA and 5-diol following oral versus percutaneous administration indicate that metabolism through the gastrointestinal tract and/or first passage through the liver leads not only to a higher level of transformation of DHEA into DHEA-S through the activity of DHEA-sulfotransferase (Luu-The et al., 1995) but also to an increased metabolism of DHEA into androgens and their inactivation through the activity of liver glucuronosyltransferases (Bélanger et al. 2003; Turgeon et al., 2001 and Hum et al., 1999). In fact, as shown in Table 1, the exposure to DHEA of 144 ng h/ml ($AUC_{0-24\,h}$) on the 14th day of oral administration of 100 mg of DHEA leads to $AUC_{0-24\,h}$ values of 5607 ng h/ml and 453 ng h/ml for ADT-G and 3α-diol-G, respectively. On the other hand, after percutaneous administration with the 10% DHEA cream, the AUC values for DHEA, ADT-G and 3 α-diol-G are 273 ng h/ml, 977 ng h/ml and 114 ng h/ml, respectively. Thus, after oral administration, 1 ng h/ml of DHEA corresponds to an AUC value of 42.1 ng h/ml for the combination of the two metabolites of androgens (ADT-G+3α-diol-G) while following application of the DHEA cream, 1 ng h/ml of DHEA exposure corresponds to 4.0 ng h/ml for the sum of the two androgen metabolites. Such data indicate that administration of DHEA by the oral route leads to an approximately 10-fold higher level of transformation of DHEA into ADT-G and 3 α-diol-G than after percutaneous administration, at least at the doses used. When the same calculations are made for the data obtained after administration of DHEA by gel, an exposure to DHEA of 1 ng h/ml is accompanied by an $AUC_{0-24\,h}$ value of 2.7 ng h/ml for ADT-G+3 α-diol-G, thus indicating an even higher ratio between oral and percutaneous DHEA administration.

As shown in Table 4 while a DHEA $AUC_{0-24\,h}$ value of 1 ng h/ml leads to an $AUC_{0-24\,h}$ value of 660 ng h/ml for DHEA-S following oral administration of DHEA, corresponding values of 73 ng h/1 and 99 ng h/1 are observed after application of the precursor steroid by cream or gel. There is thus a 6.7-9.0-fold higher amount of DHEA-S in the circulation following the same exposure to circulating DHEA (serum $AUC_{0-24\,h}$ value) after oral compared to percutaneous administration of DHEA under the conditions tested. The present data show a comparable influence of the passage of DHEA through the gastro-intestinal tract and the liver on serum DHEA-S, ADT-G and 3 α-diol-G levels.

Although a lower difference is seen, relatively higher levels of serum 4-dione are observed after oral administration of DHEA compared to percutaneous administration of the precursor steroid. Thus, after oral administration of DHEA, a 1 ng h/ml value of the DHEA $AUC_{0-24\,h}$ leads to a 0.3 ng h/ml 4-dione $AUC_{0-24\,h}$ value while values of 0.08 ng h/ml and 0.11 ng h/ml are observed after administration of DHEA by cream and gel, respectively. As measured in the circulation, the transformation of DHEA into 4-dione is thus 2.70-3.76 times higher following oral compared to percutaneous administration of DHEA.

The data of Table 5 show that the DHEA $AUC_{0-24\,h}$ value is increased by 167% over control following the daily oral administration of 100 mg DHEA compared to pretreatment basal levels while the daily percutaneous administration of 4 g of 10% DHEA cream and gel increases the serum DHEA levels by 406% and 249%, respectively. Since 400 mg of DHEA were applied on the skin compared to 100 mg by the oral route, and assuming linearity, the present data indicate that the oral route is 2.9- and 4.8-fold more efficient compared to the formulation used for the DHEA cream and gel, respectively.

In a study also performed in postmenopausal women, the oral administration of 150 mg and 300 mg of micronized DHEA resulted in maximal serum DHEA-S, DHEA and testosterone of approximately 1.5 mg/ml, 15 ng/ml and 2.75 ng/ml after the 300 mg dose and 10 μg/ml, 12 μg/ml and 1.6 ng/ml after the 150 mg DHEA dose, respectively (Buster et al. 1992). Examination of these early results shows that a 20-fold increase in serum DHEA-S led to only a 6.9-fold increase in serum testosterone while serum DHEA was increased to 11.6-fold. Moreover, when the measured serum testosterone values are adjusted to one-third to take into account the two-thirds non-specific binding in the radioimmunoassay, the serum testosterone levels remained within the physiological levels during the 12 h which follow the administration of the 150 mg DHEA dose (Buster et al. 1992).

Similar differences observed between the oral and percutaneous routes for serum DHEA are seen for 5-diol which is transformed directly from DHEA by 17β-hydroxysteroid dehydrogenase (Labrie, Luu-The, et al. 2000). In fact, while the 5-diol $AUC_{0-24\,h}$ value is increased by approximately 138% over control after oral administration of 100 mg of DHEA, increases of 363% and 218% are measured after application of 400 mg of DHEA cream and gel, respectively.

As mentioned above, man is unique, with some other primates, in having adrenals that secrete large amounts of the precursor steroids DHEA and DHEA-S, which are converted into 4-dione and then into potent androgens and/or estrogens in peripheral intracrine tissues (Labrie, 1991; Labrie, Bélanger, et al, 1995; Labrie et al. 1996; Labrie, Luu-The, et al, 1997; Simpson, 2000; Labrie, Luu-the, et al. 2005; Labrie, Poulin, et al., 2006 and Labrie, Bélanger, et al., 1998). It is thus remarkable that man, in addition to possessing very sophisticated endocrine and paracrine systems, has largely vested in sex steroid formation in peripheral tissues Labrie, 1991) and (Bélanger, et al., 1998). In fact, while the ovaries and testes are the exclusive sources of androgens and estrogens in lower mammals, the situation is very different in man and higher primates, where active sex steroids are in large part or wholly synthesized locally in peripheral tissues, thus providing target tissues with controls which adjust the formation and metabolism of sex steroids to local requirements.

Adrenal secretion of DHEA and DHEA-S increases during adrenarche in children at the age of 6-8 years, and maximal values of circulating DHEA-S are reached between the ages of 20 and 30 years. Thereafter, serum DHEA and DHEA-S levels decrease markedly (Bélanger et al. 1994). In fact, at 70 years of age, serum DHEA-S levels are decreased to approximately 20% of their peak values, while they can decrease by 95% by the age of 85-90 years (Bélanger et al. 1994) and (Migeon et al., 1957). The 70-95% reduction in the formation of DHEA and DHEA-S by the adrenals during aging results in a dramatic reduction in the formation of androgens and estrogens in peripheral target tissues (Labrie, Bélanger et al., 2006). Such a marked decrease in the formation of sex steroids in peripheral tissues could well be involved in the pathogenesis of a series diseases associated with aging.

As mentioned earlier, transformation of DHEA and DHEA-S into active androgens and/or estrogens in peripheral target tissues depends upon the level of expression of the various steroidogenic and metabolizing enzymes in each cell type (Labrie, 1991). Elucidation of the structure of most of the tissue-specific genes that encode the steroidogenic enzymes responsible for the transformation of DHEA and DHEA-S into androgens and/or estrogens has permitted rapid progress in this area (Labrie, Bélanger et al., 1995; Labrie, Luu-The et al., 1997; Labrie, Simard et al., 1996; Labrie, Luu-The et al., 2005; Labrie, Poulin et al., Labrie, Luu-The, et al. 2000, Labrie, Sugimoto, et al. 1992, Labrie, Simard et al, 1992; Luu-The, et al. 1995; and Labrie, Durocher et al. 1995).

The data showing the presence of relatively high levels of androgen metabolites in normal women (Labrie, Bélanger, et al. 1997; Labrie, Bélanger et al., 2006; Labrie, and Bélanger, et al, 2007b) strongly suggest that the androgens play a major physiological but still underestimated role in women. The 44.5% fall which occurs in serum DHEA from 20 to 30 years of age to the age of 40-50 years in women (Bélanger et al., 2006) could well explain the bone loss which precedes menopause. In fact, age-related bone loss has been reported to begin in the fourth decade and changes in bone turnover have been found well before menopause (Mazess 1982; Riggs, et al. 1981, and Johnston et al. 1985). In agreement with these findings, bone density was lower at all sites examined in women classified as perimenopausal compared to premenopausal (Steinberg, et al., 1989). In agreement with these findings, the changes in precursor androgen secretion by the adrenals precede by 10-20 years the decrease in ovarian estrogen secretion which abruptly stops at menopause (Labrie, Bélanger, et al. 2006)

It is important to realize that not only serum DHEA and DHEA-S decrease by 50% between the ages of 21 years and 50 years but that a similar decrease is observed for serum testosterone (Zumoff et al. 1995). Such data could well suggest that hormone replacement therapy with androgens or their precursor(s) should start early at menopause in order to compensate for this early fall in the secretion of androgen precursors by the adrenals and the parallel decrease in serum testosterone (Labrie, 2006).

The active androgens and estrogens synthesized in peripheral target tissues exert their activity in the cells of origin and very little diffusion of the active sex steroids occurs, thus resulting in very low levels in the circulation. In fact, as observed previously (Labrie, Bélanger et al., 1997) and confirmed in the present study, the most striking effects of DHEA administration are seen on the circulating levels of the glucuronide derivatives of the metabolites of DHT, namely ADT-G and 3 α-diol-G while no significant or only minor changes are seen in the serum levels of testosterone, E1 or E2. These active steroids are produced locally in the peripheral intracrine tissues which possess the appropriate steroidogenic enzymes to synthesize DHT from the adrenal precursors DHEA and DHEA-S as well as the enzymes that transform DHT into the inactive metabolites ADT and 3α-diol which are further modified by glucuronidation (Bélanger et al. 2003).

In a recent study, daily oral administration of 50 mg of DHEA had no significant effect on serum testosterone or DHT while DHEA and ADT-G were increased to a similar extent (80-90%) (Arlt et al. 2001). In another study, predosing serum levels of DHEA-S in postmenopausal women were increased from 0.55 µg/ml to about 1.4 µg/ml (Casson et al. 1998), after daily oral administration of 25 mg of DHEA for 6 months. Serum DHEA and testosterone levels, however, measured 23 h after last administration of DHEA, were not changed significantly. Another study has indicated that the 50 mg daily oral dose of DHEA leads to serum androgen levels in the premenopausal range (Buster et al. 1992).

The present data clearly demonstrate that DHEA and DHEA-S are converted in specific peripheral intracrine tissues into active androgens and/or estrogens which can exert their biological effects at their site of synthesis with no or only small release of active steroids in the circulation. Accordingly, changes in serum levels of testosterone, E1 or E2 cannot be used as parameters of transformation of DHEA into androgens or estrogens (Labrie, Bélanger et al., 2006). In fact, the active steroids are metabolized in the same cells where they have been synthesized and exerted their action into inactive glucuronidated and sulfated metabolites which finally diffuse in the extracellular compartment and can be measured in the circulation (Labrie, Bélanger et al., 2006; Labrie, Bélanger et al., 1997 and Labrie, Bélanger et al. 2007). Measurement of the conjugated metabolites of androgens is the only approach that permits an accurate estimate of the total androgen pool in women. It is most likely that a similar situation exists for estrogens, although a precise evaluation of the pharmacokinetics of estrogen metabolism and identification of their metabolites remains to be established.

Example 3

Clinical Trail ERC-210

Intravaginal DHEA, the Physiological Treatment of Vaginal Atrophy

Subjects and Methods

This study is a phase III, prospective, multicenter, randomized, placebo-controlled, and double-blind trial of 50 subjects per arm (for a total of 200 subjects). Two hundred postmenopausal women were thus randomized to receive a daily ovule of the following DHEA concentrations: 0.0%, 0.25% (3.25 mg DHEA), 0.5% (6.5 mg DHEA) or 1.0% (13 mg DHEA) applied intravaginally with an applicator. The study was divided into two phases, namely screening followed by a treatment period of 12-week duration.

The inclusion criteria were the following:
Postmenopausal women who satisfy either a or b or c:
a. No menses for at least one year, or;
b. FSH levels ≥40 mIU/mL (within 60 days prior to Day 1) in women with no menses ≥6 months but <12 months, or hysterectomized women who were premenopausal at the time of hysterectomy or;
c. Six weeks or more (of screening visit) following bilateral oophorectomy.
Women who have self-identified at least one moderate to severe of the following symptoms:
Vaginal dryness (none, mild, moderate or severe).
Vaginal and/or vulvar irritation/itching (none, mild, moderate or severe).
Vaginal pain associated with sexual activity (none, mild, moderate or severe).
Women should identify which symptom is the most bothersome to her at start of treatment. The change of this symptom will be followed and will serve to evaluate the effect of treatment.
Women between 40 and 75 years of age.
Willing to participate in the study and sign an informed consent.
Women having a low maturation index (no greater part of guidance than 5% of superficial cells on vaginal smear).
Women having a vaginal pH above 5.
Normal mammography within 9 months of study start.
Normal breast examination.
A normal PAP smear (which includes inflammatory changes) within the last 12 months (of Day 1). For hysterectomized women, the PAP smear will consist of at least one slide.
No former or present narcotic addiction or alcoholism.
Body weight within the range of 18.5 to 35 of ideal body weight according to body mass index (BMI) (WHO).
No hepatic or renal impairment or condition known to affect drug or steroid metabolism.
Normal baseline hematology, clinical chemistry, and urinalysis.
Negative serology for HIV1/HIV2 and hepatitis B and C.
The exclusion criteria were:
Undiagnosed abnormal genital bleeding.
Previous diagnosis of cancer, except skin cancer (non melanoma).
Endometrial hyperplasia at biopsy performed at screening or endometrial cancer.
Active or history of thromboembolic disease.

Significant metabolic or endocrine disease.

Clinically significant gastrointestinal, liver or gallbladder disease.

Recurrent migraine headache not controlled by conventional therapy.

Diabetes mellitus not controlled by conventional therapy.

Significant complication on previous hormonal therapy.

Use of estrogen alone injectable drug therapy or progestin implant within 3 months prior to study entry (screening visit).

Use of estrogen pellet or progestin injectable drug within six months prior to study entry.

Oral estrogen, progestin or DHEA exposure or intrauterine progestin therapy in the eight weeks prior to baseline assessments.

Vaginal hormonal products (rings, creams or gels) or transdermal estrogen alone or estrogen/progestin products in the 4 weeks prior to baseline assessments.

Patients can washout as follows, but the questionnaire on vaginal atrophy must be answered after the required washout period:

At least an eight-week washout period for prior oral estrogen, DHEA and/or progestin therapy.
  At least a four-week washout period for prior transdermal hormone therapy
  At least a four-week washout period for locally delivered hormone replacement therapy for vaginal dryness.
  At least 6 months for prior estrogen pellet therapy or progestin injectable drug therapy.
  Eight weeks or longer for prior intrauterine progestin therapy.
  Six months or longer for prior progestin implants and estrogen alone injectable drug therapy.
  Previous treatment with androgens or anabolic steroids within 3 months prior to screening visit.
  Oral corticosteroid treatment within six weeks of study start.
  No chronic use of corticosteroid allowed (intermittent nasal spray or topical on skin, eyes or ears is permitted).
  Cardiac failure or manifest coronary heart disease.
  Hypertension equal to or above 160/95 mm Hg or not controlled by standard therapy.
  Confirmed clinically significant depression or confirmed history of severe psychiatric disturbance.
  The administration of any investigational drug within 30 days of screening visit.
  Clinically relevant abnormal serum biochemistry or haematology.
  Baseline cervical cytology showing low-grade squamous intraepithelial lesion (LGISIL) or worse.
  Smoking more than 10 cigarettes a day.
  Drugs that interfere with the metabolism of estrogens (eg, ketoconazole, steroid formation or action inhibitors).
  SERMs or drug interacting with steroid receptors.
  Known presence of uterine fibroma or palpable at gynecological exam.
  Coagulation disorders or on anticoagulant drug therapy.

Laboratory Tests

The usual laboratory tests, namely hematology (including complete blood count and coagulation), blood chemistry and urinalysis were performed at all visits. Serum FSH had to be measured only in women who had no menses for ≥6 months but <12 months or who were premenopausal at the time of hysterectomy. Serum steroid levels of DHEA, DHEA-S, androst-5-ene-3β, 17β-diol (5-diol), dihydrotestosterone (DHT), testosterone (testo), androstenedione (4-dione), estrone ($E_1$), estradiol ($E_2$), $E_1$-S, androsterone glucuronide (ADT-G), androstane-3α,17β-diol-3G (3α-diol-3G) and 3α-diol-17G were measured at the Laboratory of Molecular Endocrinology, CHUL Research Center by mass spectrometry as described (Labrie, Bélanger et al. 2006; Labrie, Bélanger et al. 2007; Labrie, Cusan et al. 2008).

Vaginal pH and Cytology

For the maturation index and Papanicolaou (PAP) smear, all samples were examined by the same cytopathologist (Dr. Robert Dubé, Department of cytology-pathology, Enfant-Jésus Hospital, Quebec City, Canada) blinded to the treatment regimens. A 100-cell count was performed to classify cells as superficial (S), intermediate (I) and parabasal (P) squamous cell types (Meisels 1967; Wied 1993).

Vaginal smears were obtained by scraping the middle third of the side wall of the vagina with the rounded end of an Ayre spatula. The material was then applied to a glass slide and immediately fixed with Spray-Cyte. These samples were sent to the central laboratory for determination of the maturation index.

Vaginal pH was measured by applying a pH indicator strip directly to the lateral wall of the vagina with a forceps. For the Papanicolaou smear—if not done in the last 12 months, specimens were obtained from the endocervix, exocervix and vaginal vault and immediately fixed with cytospray. The specimens were collected with an Ayre spatula.

Endometrial Biospy

Endometrial biopsy was performed at screening and at month 3 at end of study. All biopsies were examined by the same pathologist at the central laboratory (Dr. Robert Dubé, Department of cytology-pathology, Enfant-Jésus Hospital, Quebec City, Canada).

Vaginal Examination

At the same time intervals of 2, 4, 8 and 12 weeks, the gynaecologist or physician in charge of the study at each site performed a vaginal exam to evaluate the degree of severity (none, mild, moderate or severe, analyzed using values of 0, 1, 2 and 3, respectively) for the main signs of vaginal atrophy, namely vaginal secretions, vaginal color, vaginal epithelial integrity and vaginal epithelial surface thickness. As can be seen in FIGS. 26 to 29, a time-dependent dose-related and statistically significant improvement of all four signs of vaginal atrophy was seen. In fact, the beneficial effects observed by the gynaecologist and or physician are almost superimposable to those self-reported by women on their most bothersome symptoms.

Vaginal examination was performed at screening and then at day 1 and at 2, 4, 8 and 12 weeks. Vaginal secretions, vaginal color, vaginal epithelial integrity and vaginal epithelial surface thickness were evaluated according to the following degrees of severity: none, mild, moderate or severe. The definitions of severity were as follows:

a) Vaginal secretions

No atrophy: Normal clear secretions noted on vaginal walls.

Mild: Superficial coating of secretions, difficulty with speculum insertion.

Moderate: Scant not covering the entire vaginal vault, may need lubrication with speculum insertion to prevent pain.

Severe: None, inflamed, ulceration noted, need lubrication with speculum insertion to prevent pain.

b) Vaginal epithelial integrity

No atrophy: Normal.

Mild: Vaginal surface bleeds with scraping.

Moderate: Vaginal surface bleeds with light contact.

Severe: Vaginal surface has petechiae before contact and bleeds with light contact.

c) Vaginal epithelial surface thickness
  No atrophy: Rugation and elasticity of vault.
  Mild: Poor rogation with some elasticity noted of vaginal vault.
  Moderate: Smooth, some elasticity of vaginal vault.
  Severe: Smooth, no elasticity, constricts of the upper ⅓ of vagina or loss of vaginal tone (cystocele and rectocele).
d) Vaginal color
  No atrophy: Pink.
  Mild: Lighter in color.
  Moderate: Pale in color.
  Severe: Transparent, either no color or inflamed.

Statistics

Summary tabulations will be prepared that will display the number of observations, mean or geometric mean as appropriate, standard deviation, standard error of the mean, 95% two-sided confidence interval (CI), median, minimum, and maximum for continuous variables, and the number and percent per category for categorical data. Statistical analyses will be performed at the two-sided significance level of 0.05 unless otherwise stated. The categories for summarization will in general consist of the dose levels of the DHEA treatments, 0% (placebo), 0.25%, 0.5% and 1.0% DHEA.

The primary endpoints for analysis will consist of the following:

Statistically significant improvement in the moderate to severe symptom identified by the subject as most bothersome to her. The symptom severity is based on symptoms of increasing severity: none, mild, moderate or severe. These ratings will be analyzed using the values 0, 1, 2 and 3, respectively; all subjects must have at least one baseline symptom that is graded as 2 or 3. The symptoms of interest are vaginal dryness, vaginal and/or vulvar irritation/itching, and vaginal pain associated with sexual activity.

Statistically significant decrease in parabasal cells and a statistically significant increase in superficial cells. The data is measured in percentage. The maturation value will also be calculated.

Statistically significant lowering of vaginal pH.

Analysis Populations

The Intent-to-Treat (ITT) Population will consist of the treated subjects with a baseline and at least one post-baseline efficacy assessment. Subjects who may have received the wrong treatment will be analyzed as randomized. This analysis population is to be considered the primary analysis population. Subjects in this population who are missing observations post-baseline will have the last value carried forward for efficacy analyses.

The Per Protocol (PP) Population consists of the subset of the treated population that completes the study through the time point of 12 weeks with no major protocol violations considered to compromise efficacy data. Major protocol violations will be determined before the study blind is broken, based on review of data listings and monitoring reports of protocol deviations. Subjects in the PP population must have received at least 90% of the required number of applications of study treatment in the protocol-specified duration for that subject, based on the subject diary data. Subjects in the PP population must be compliant with the visit window schedule: ±3 days for Day 14, and ±7 days for Weeks 4, 8 and 12. Subjects who received the wrong treatment, but for whom the treatment received can be unequivocally confirmed, will be analyzed in the PP Population as treated, provided they have no other violations that compromise their data. The PP population will be a supportive population for efficacy data analysis.

The Safety Population will be defined as all subjects who receive an administration of either test article (DHEA at any dose or Placebo), and who have any safety information available. All safety data analyses will be based on this population. Analysis will be based on the treatment actually received.

Efficacy Evaluation

Efficacy analyses will be performed primarily on the ITT Population, and the Per-Protocol population will provide supportive efficacy analyses. The primary study objective is to evaluate the dose-response of vaginal mucosal parameters to the local action of DHEA in postmenopausal women suffering from vaginal atrophy, specifically by determination of the minimal dose of DHEA that produces maximal effect on the vaginal mucosa. The co-primary efficacy endpoints to address this objective are decrease in parabasal cells, decrease in vaginal pH, increase in superficial cells (collectively, these endpoints will be denoted as physiological parameters) and subject self-reported most bothersome symptom including vaginal dryness, vaginal and/or vulvar itching/irritation, and vaginal pain associated with sexual activity (collectively, these endpoints will be denoted as symptom score parameters). In addition to these primary endpoints, the maturation value will also be calculated. The self-reported symptom scores take the following values: none, mild, moderate or severe to be analyzed using values of 0, 1, 2 or 3, respectively. All endpoints must demonstrate statistically significant effects relative to placebo, therefore no statistical adjustment is required for multiple endpoints.

The primary timepoint for analysis will be the 12-week assessment, with additional presentations of the data for 2, 4 and 8 weeks. The change from baseline to post-baseline assessment will be used for analysis as well as the difference with placebo.

Results

Figure 22:
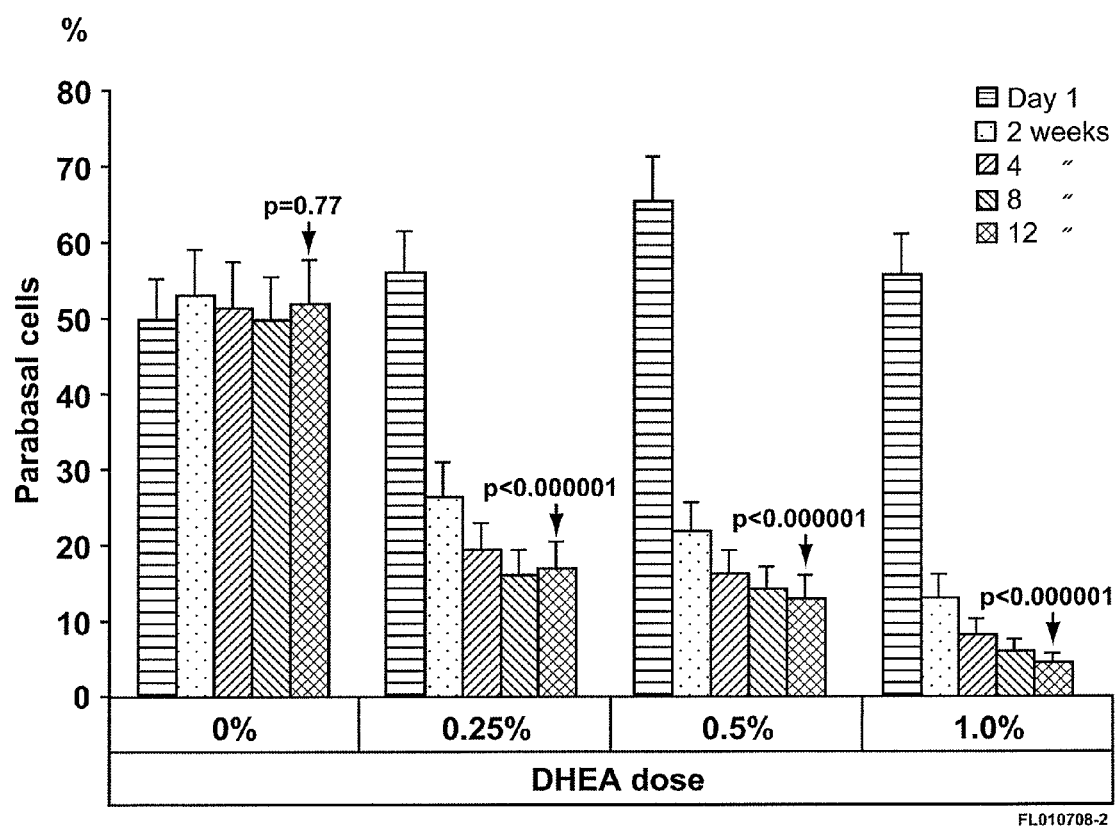
FIG. 22 shows the effect of daily intravaginal application of 0.0%, 0.25%, 0.5% and 1.0% DHEA (Prasterone) for 2, 4, 8 and 12 weeks on the percentage of vaginal parabasal cells in postmenopausal women. Data are expressed as means±SEM.

Since parabasal cells are usually the predominant category in the vaginal smear of postmenopausal women suffering from at least one moderate to severe symptom of vaginal atrophy, it can be seen in FIG. 22 and Table 6 that already at 2 weeks of treatment, the lowest dose of DHEA (0.25%) decreased the % of parabasal cells by 29.5±0.51% from 56.0 to 26.5% while decreases of 37.8±0.46% and 36.6% were observed, respectively, with the 0.5% and 1.0% DHEA doses at the same time interval. At the standard duration of 12 weeks of treatment, decreases of 39.5±0.57% (p<0.000001), 45.6±0.55% (p<0.000001) and 45.2±0.53% (p<0.000001) were observed with the 0.25%, 0.5% and 1.0% DHEA doses, respectively, while no significant effect was observed in the placebo group at any time interval.

Figure 23:
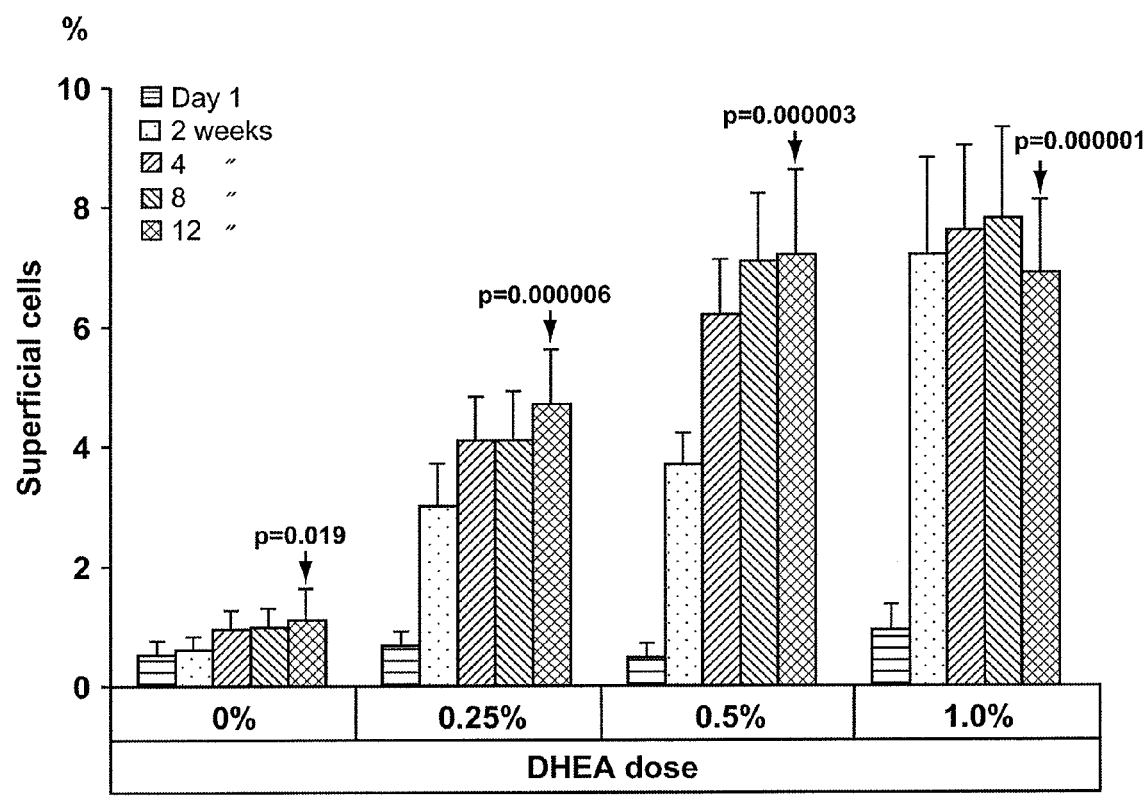
FIG. 23 shows the effect of daily intravaginal application of 0.0%, 0.25%, 0.5% and 1.0% DHEA (Prasterone) for 2, 4, 8 and 12 weeks on the percentage of vaginal superficial cells in postmenopausal women. Data are expressed as means±SEM.

While no significant effect was seen at 12 weeks in the placebo group on the % change in superficial cells (Table 6), increases of 3.96±0.10% (p=0.0002), 6.71±0.14% (p=0.00001) and 5.92±0.12% (p=0.00001) were measured in the 0.25%, 0.5% and 1.0% DHEA groups, respectively. It can also be seen that at the 0.5% DHEA dose, 48.0% of the maximal effect was reached at 2 weeks while at 4 and 8 weeks, 84.8% and 99.0% of the maximal effect were achieved. At the 1.0% DHEA dose, the maximal effect was already reached at 2 weeks. FIG. 23 illustrates the absolute values of the % of superficial cells at the different DHEA doses and time intervals.

Figure 24:
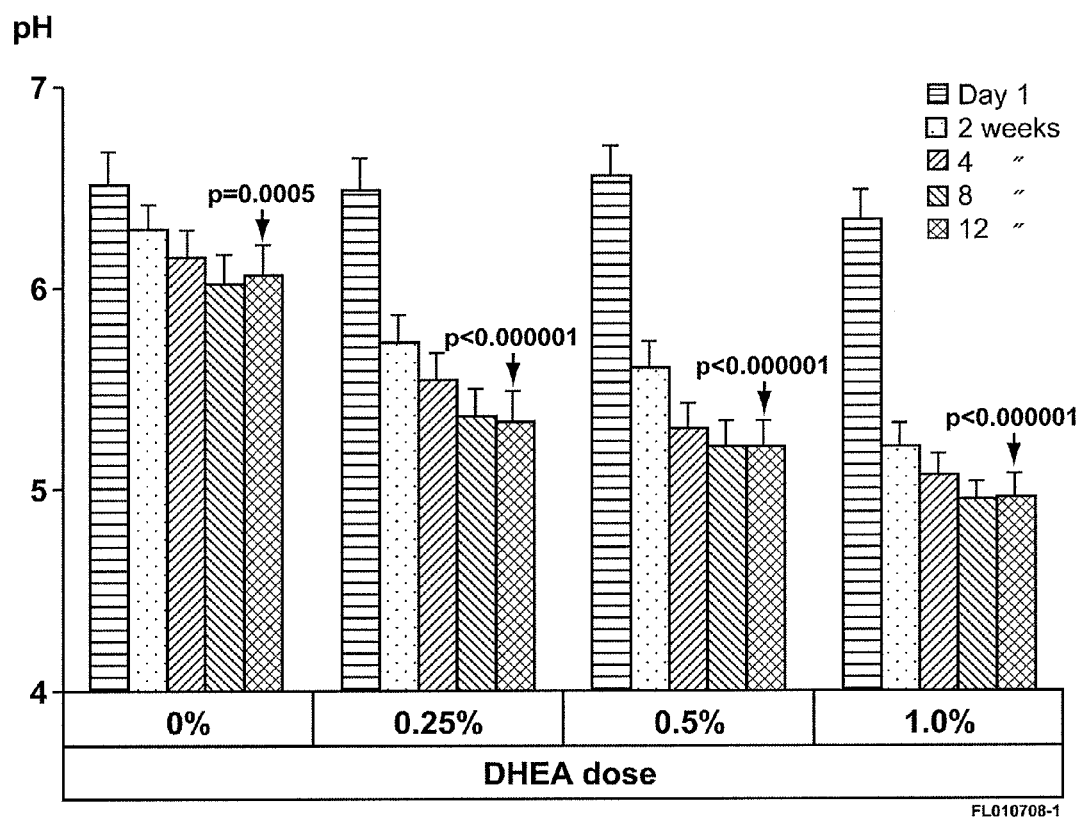
FIG. 24 shows the effect of daily intravaginal application of 0.0%, 0.25%, 0.5% and 1.0% DHEA (Prasterone) for 2, 4, 8 and 12 weeks on vaginal pH in postmenopausal women. Data are expressed as means±SEM.

Vaginal pH was decreased at 12 weeks by 0.47±0.11 from 6.52±0.13 units in the placebo group (Table 6, FIG. 24) while decreases of 1.12±0.11 (p=0.0005) from 6.49±0.12 units, 1.35±0.3 from 6.56±0.13 pH units, 1.35±0.13 from 6.56±0.13 pH units and of 1.39±0.14 from 6.34±0.3 pH units were observed in the 0.25%, 0.50% and 1.0% DHEA-treated groups, respectively (Table 7). It can be seen in the same table that at the 0.5% DHEA dose, 70.6% and 94.1% of the maximal effect on pH (reduction of 1.36 pH units) was achieved at 2 and 4 weeks of treatment, respectively. The low 0.25% DHEA dose, on the other hand, reached only 83.0% of the maximal effect of 0.5% DHEA at 12 weeks. No significant difference in the change of pH was observed between the 0.50% and 1.0% DHEA doses at 4, 8 and 12 weeks (Table 7). FIG. 24 illustrates the absolute pH values at the different DHEA doses and time intervals.

Figure 25:
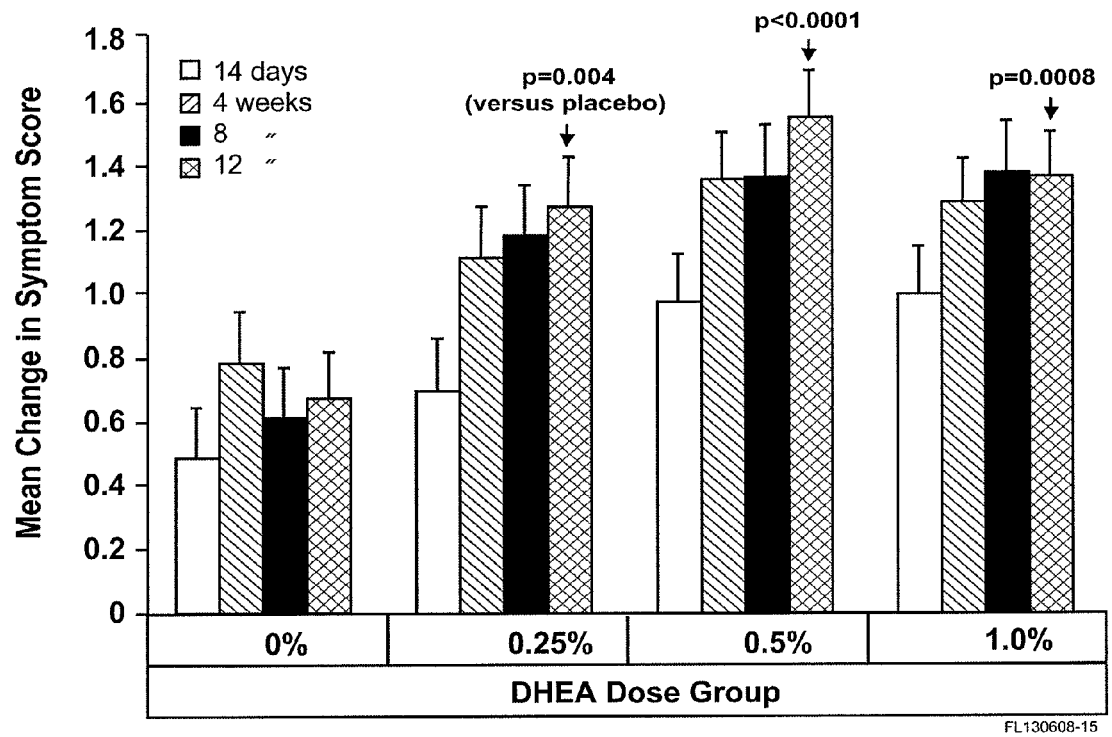
FIG. 25 shows the effect of daily intravaginal application of 0.0%, 0.25%, 0.5% and 1.0% DHEA (Prasterone) for 2, 4, 8 and 12 weeks on the change in severity of the symptom of vaginal atrophy judged by women themselves as being the most bothersome. Values are compared to day 1 and are expressed as means±SEM.
Figure 26:
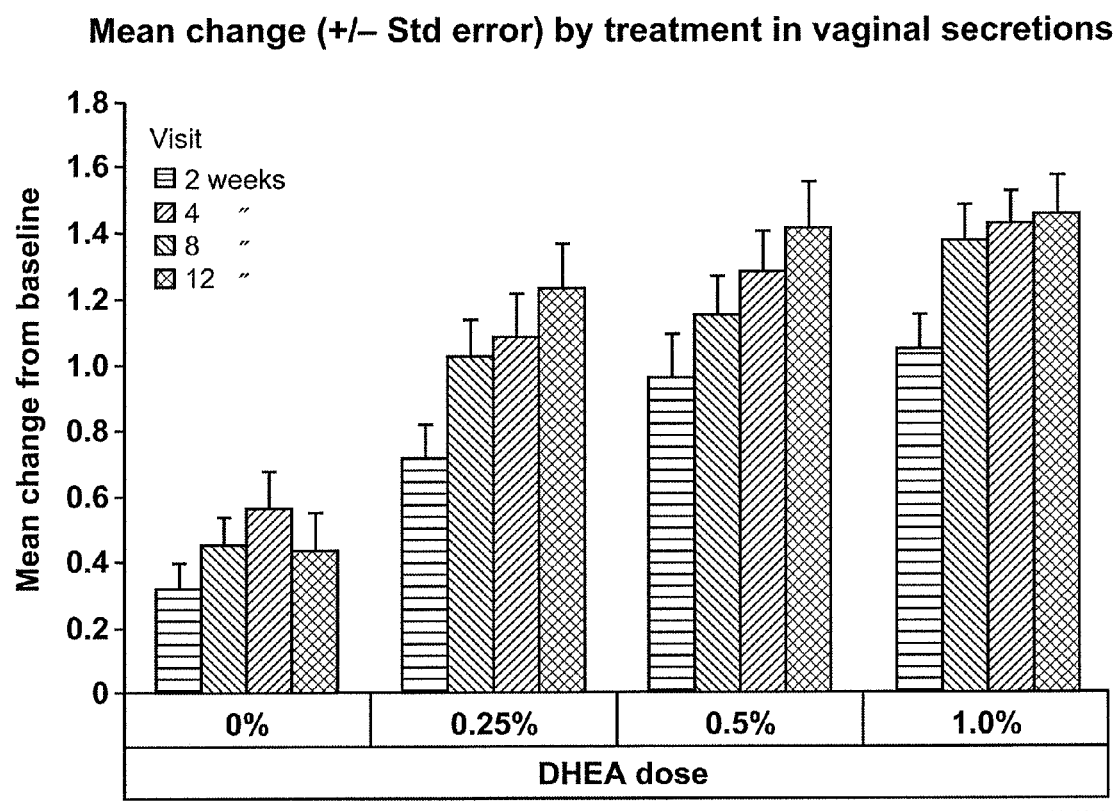
FIG. 26 shows the effect of daily intravaginal application of 0.0%, 0.25%, 0.5% and 1.0% DHEA (Prasterone) for 2, 4, 8 and 12 weeks on the change in vaginal secretions evaluated at vaginal examination. Data are expressed as means±SEM.
Figure 27:
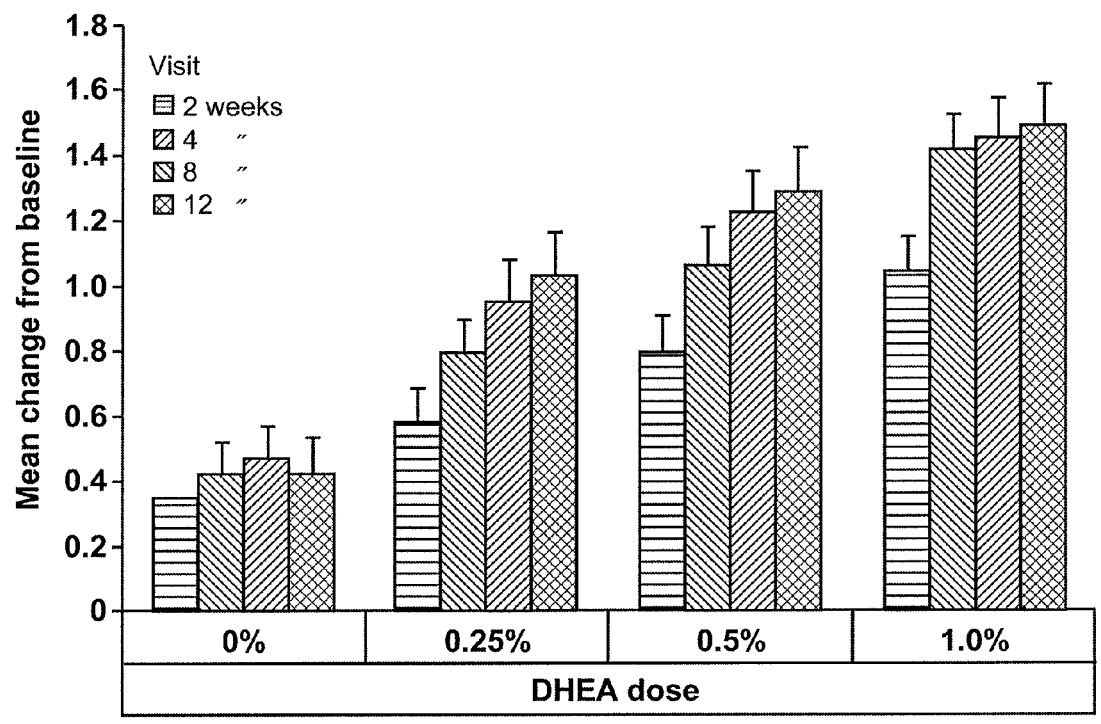
FIG. 27 shows the effect of daily intravaginal application of 0.0%, 0.25%, 0.5% and 1.0% DHEA (Prasterone) for 2, 4, 8 and 12 weeks on the change in vaginal color evaluated at vaginal examination. Data are expressed as means±SEM.
Figure 28:
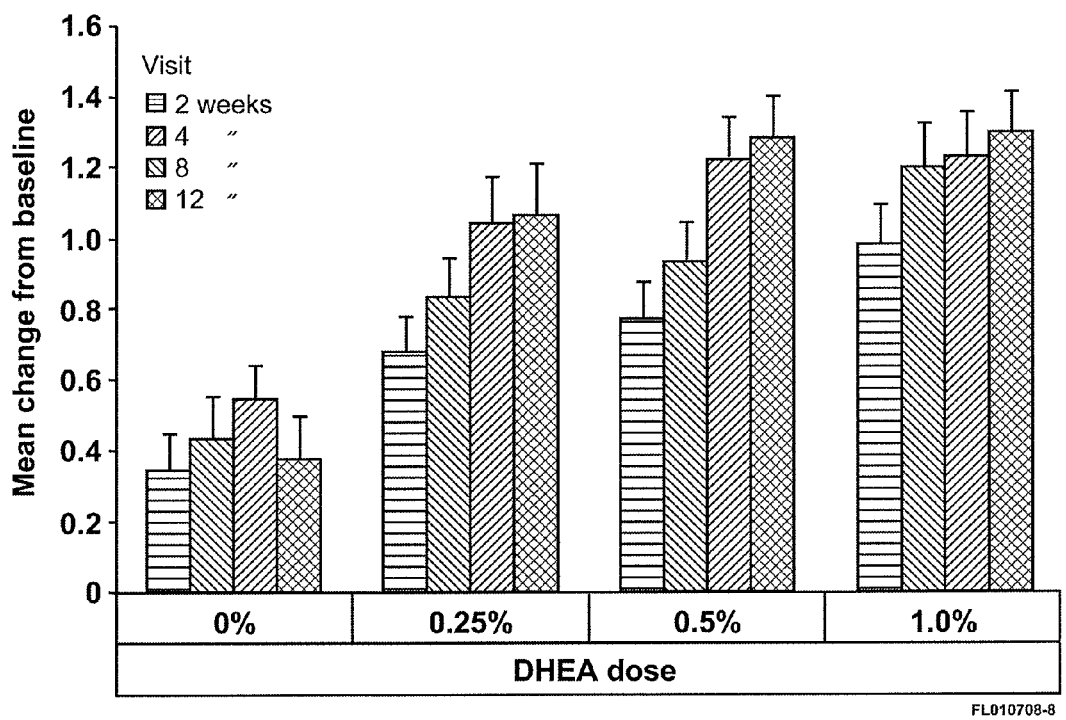
FIG. 28 shows the effect of daily intravaginal application of 0.0%, 0.25%, 0.5% and 1.0% DHEA (Prasterone) for 2, 4, 8 and 12 weeks on the change in vaginal epithelial integrity evaluated at vaginal examination. Data are expressed as means±SEM.
Figure 29:
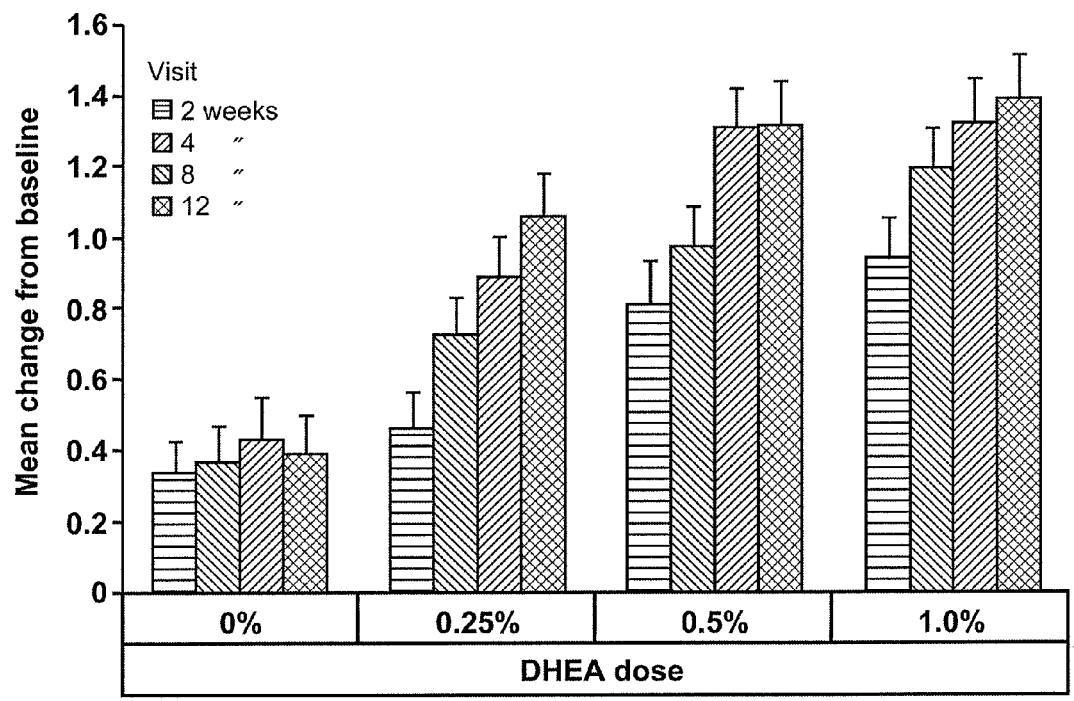
FIG. 29 shows effect of daily intravaginal application of 0.0%, 0.25%, 0.5% and 1.0% DHEA (Prasterone) for 2, 4, 8 and 12 weeks on the change in vaginal epithelial thickness evaluated at vaginal examination. Data are expressed as means±SEM.

All women needed to have at entry one or more of the following symptoms of vaginal atrophy evaluated by herself as moderate to severe: dryness, vaginal or vulval irritation/itching or vaginal pain at sexual activity. The self-identified symptoms reported as none, mild, moderate or severe were analysed using values of 0, 1, 2 and 3, respectively. As illustrated in Table 8, at the 12-week interval, the severity of the most bothersome symptom was reduced by 0.67±0.15 in the placebo group, 1.27±0.16 in the 0.25% DHEA group (p=0.004 vs placebo), 1.56±0.15 in the group receiving 0.5% DHEA (p<0.0001 vs placebo) and 1.37±0.14 in the group receiving the higher 1.0 DHEA dose (p=0.0008 vs placebo). FIG. 25 illustrates the degree of improvement of the most bothersome symptom at the different DHEA doses and time intervals. Vaginal dryness, pain associated with sexual activity and vaginal and/or vulvar irritation/itching were identified at baseline as the most bothersome symptom. In the placebo group, vaginal dryness accounted for % of the improvements noted by the participants.

As illustrated in FIG. 25, the improvement of the most bothersome symptom was already highly significantly different (p=0.004) at the 0.25% DHEA dose. The percentage of women with no change or a worsening of a score of 1 at 12 weeks went from 53.5% in the placebo group to 27.5%, 17.8% and 19.6% in the 0.25%, 0.5% and 1.0% groups, respectively (Table 9). The improvements by 2 or 3 categories of severity were observed in 21.8% of women treated with placebo while 50.0%, 53.3% and 47.9% of women who received the 0.25%, 0.5% and 1.0% DHEA formulations reported such an important improvement. Only 4.6% of women indicated a decrease from severe to none in the placebo group compared with 7.5%, 20% and 10.9% in the same DHEA-treated groups.

At the same time intervals of 2, 4, 8 and 12 weeks, the gynecologist or physician in charge of the clinical trial at each study site performed a vaginal exam to evaluate the degree of severity (none, mild, moderate or severe analyzed using values of 0, 1, 2, and 3, respectively) for the main signs of vaginal atrophy, namely vaginal secretions, vaginal color, vaginal epithelial integrity and vaginal epithelial surface thickness. As can be seen in FIGS. 26 to 29, a time-dependent and dose-related as well as highly statistically significant improvement of all four signs of vaginal atrophy was seen. In fact, the beneficial effects observed by the gynecologist or physician are almost superimposable to those self-reported by women on their most bothersome symptoms as well as to the effects on vaginal parabasal and superficial cells and pH which are objective parameters of DHEA action.

Figure 30:
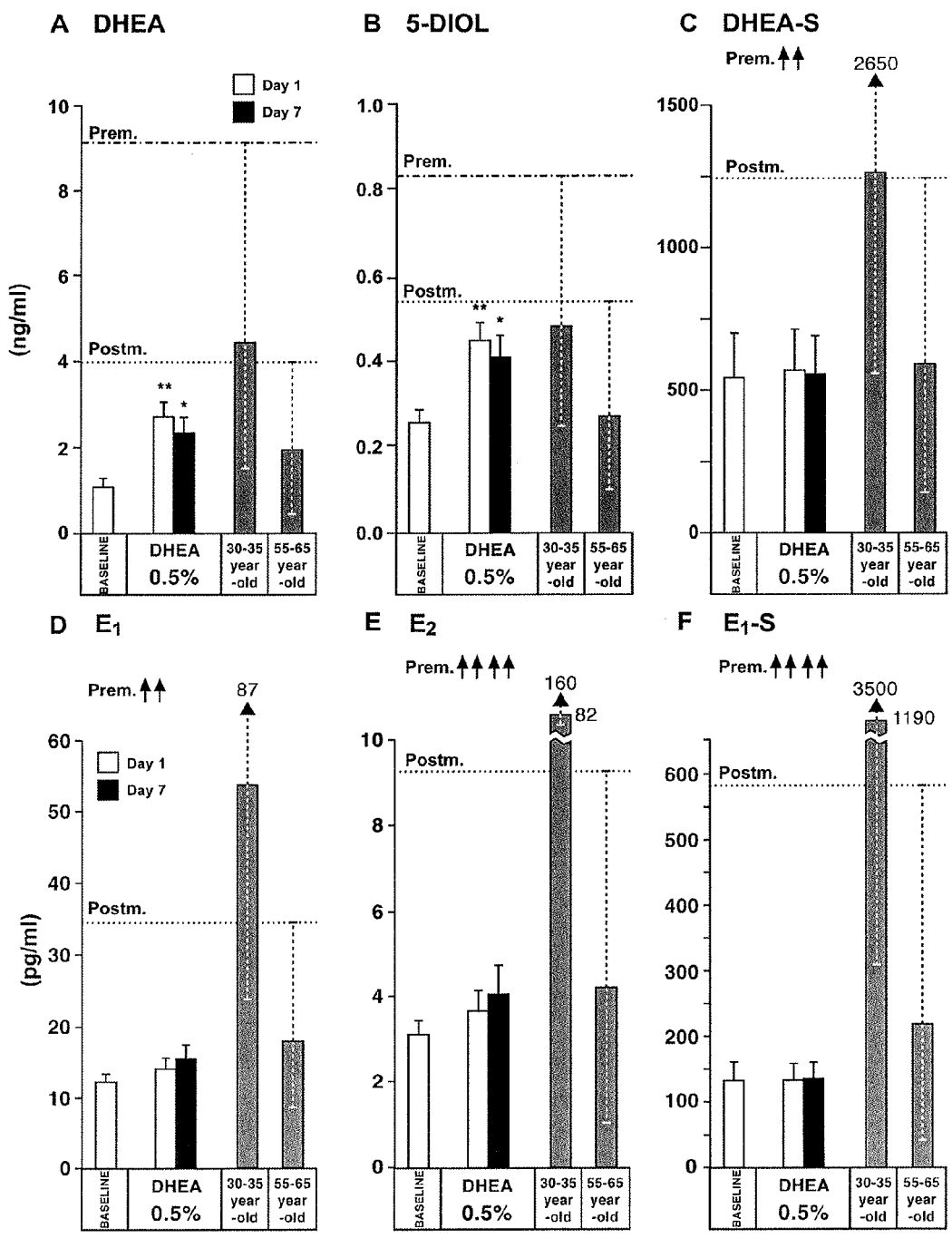
FIG. 30 shows the average 24-hour serum concentrations ($AUC_{0-24h}/24$) of DHEA, 5-Diol, DHEA-S, E1, E2 and E1-S measured on days 1 and 7 following once daily administration of vaginal ovule containing 0.5% DHEA. Data are expressed as means±SEM (n=10). Serum steroid concentrations measured in 30-35 year-old premenopausal (n=47) as well as in 55-65 year-old postmenopausal (n=369) women are added as reference data which are expressed as means and $5^{th}$ and $95^{th}$ centiles (dashed lines). *, p<0.05, **, p<0.01, experimental versus baseline. (Data are from Labrie, Cusan et al. 2008).
Figure 31:
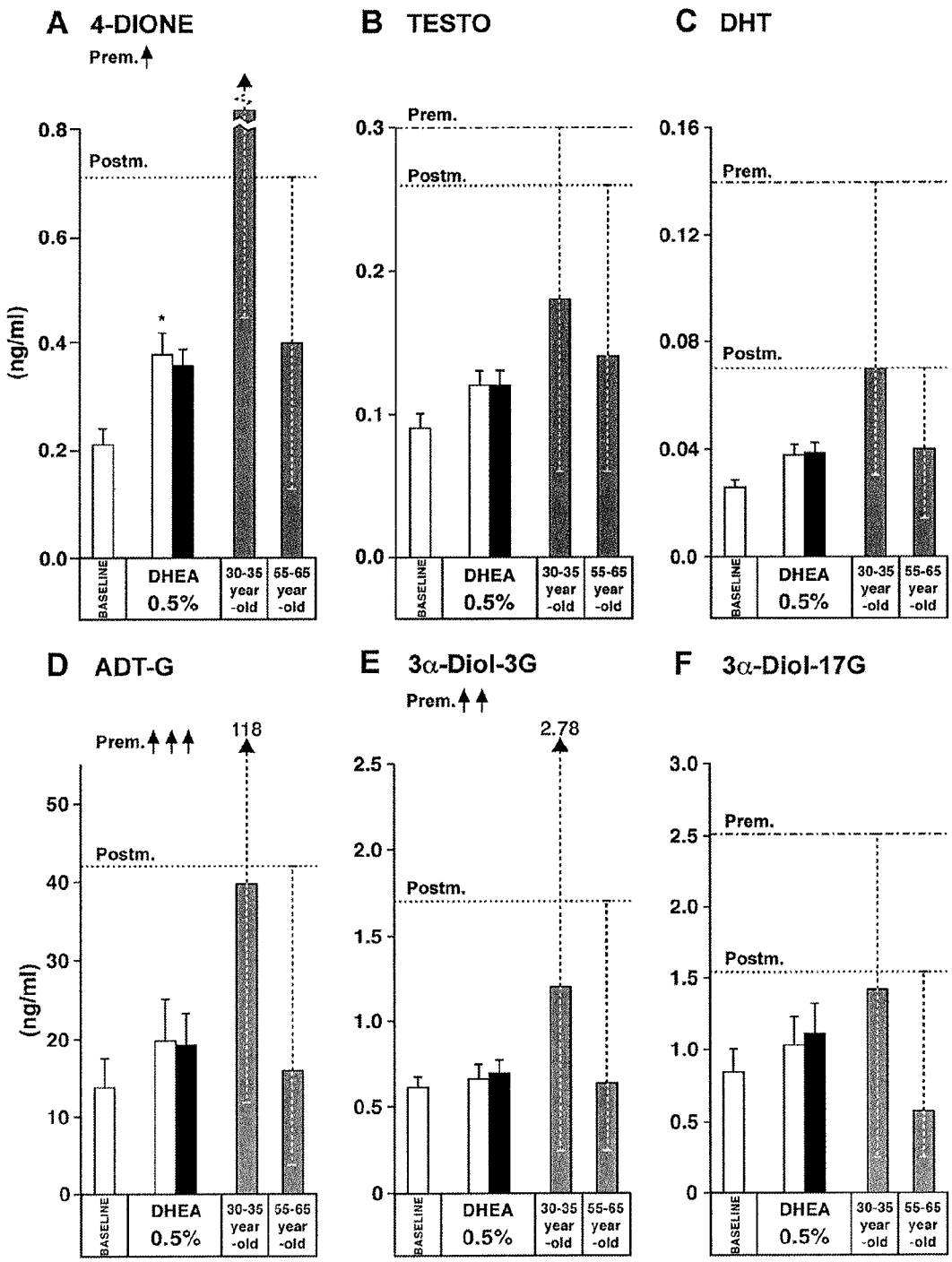
FIG. 31 shows the average 24-hour serum concentrations ($AUC_{0-24h}/24$) of 4-Dione, testosterone, DHT ADT-G, 3α-Diol-3G and 3α-Diol-17G measured on days 1 and 7 following once daily administration of vaginal ovule containing 0.5% DHEA. Data are expressed as means±SEM (n=10). Serum steroid concentrations measured in 30-35 year-old premenopausal (n=47) and 55-65 year-old postmenopausal (n=369) women are added as reference data which are expressed as means and $5^{th}$ and $95^{th}$ centiles (dashed lines). *, p<0.05, experimental versus baseline. (Data are from Labrie, Cusan et al. 2008).

FIGS. 30 and 31 illustrate the average 24 h (calculated from $AUC_{0-24h}$ values measured on days 1 and 7 of treatment) serum steroid levels of DHEA and eleven of its metabolites taken from a recent study (Labrie, Cusan et al. 2008). It can be seen that only serum DHEA and 5-diol (and 4-dione at day 1) are increased significantly but well within the limits of values found in postmenopausal women (Labrie, Bélanger et al. 2006). Serum estrogens ($E_1$, $E_2$ and $E_1S$) as well as serum androgens (testo and DHT) are not significantly affected.

TABLE 6

Change from day 1 in % parabasal and superficial cells during local treatment with increasing doses of DHEA*

| | 2 weeks | 4 weeks | 8 weeks | 12 weeks |
|---|---|---|---|---|
| Parabasal cells | | | | |
| 0.0% DHEA | +3.6 ± 0.32 | +0.02 ± 0.32 | −1.17 ± 0.37 | +1.04 ± 0.35 |
| 0.25% DHEA | −29.5 ± 0.51 | −38.4 ± 0.51 | −40.3 ± 0.55 | −39.5 ± 0.57 |
| 0.50% DHEA | −37.8 ± 0.46 | −43.4 ± 0.50 | −47.8 ± 0.49 | −45.6 ± 0.55 |
| 1.0% DHEA | −36.6 ± 0.50 | −42.5 ± 0.51 | −43.7 ± 0.50 | −45.2 ± 0.53 |
| Superficial cells | | | | |
| 0.0% DHEA | 0.10 ± 0.03 | 0.37 ± 0.03 | 0.40 ± 0.03 | 0.53 ± 0.05 |
| 0.25% DHEA | 2.32 ± 0.07 | 3.38 ± 0.08 | 3.42 ± 0.09 | 3.96 ± 0.10 |
| 0.50% DHEA | 3.22 ± 0.05 | 5.69 ± 0.09 | 6.64 ± 0.11 | 6.71 ± 0.14 |
| 1.0% DHEA | 6.26 ± 0.16 | 6.64 ± 0.14 | 6.88 ± 0.16 | 5.92 ± 0.12 |

*mean ± SEM

TABLE 7

Change from day 1 in vaginal pH during local treatment with increasing doses of DHEA*

| DHEA dose | 2 weeks | 4 weeks | 8 weeks | 12 weeks |
|---|---|---|---|---|
| 0.0% DHEA | −0.23 ± 0.08 | −0.37 ± 0.09 | −0.51 ± 0.10 | −0.47 ± 0.11 |
| 0.25% DHEA | −0.76 ± 0.12 | −0.93 ± 0.12 | −1.09 ± 0.10 | −1.12 ± 0.11 |
| 0.50% DHEA | −0.96 ± 0.14 | −1.28 ± 0.12 | −1.36 ± 0.12 | −1.35 ± 0.13 |
| 1.0% DHEA | −1.13 ± 0.12 | −1.30 ± 0.12 | −1.41 ± 0.12 | −1.39 ± 0.14 |

*mean ± SEM

TABLE 8

Change from day 1 in the most bothersome symptoms of vaginal atrophy during local treatment with increasing doses of DHEA*

| DHEA dose | 2 weeks | 4 weeks | 8 weeks | 12 weeks |
|---|---|---|---|---|
| 0.0% DHEA | −0.49 ± 0.16 | −0.79 ± 0.16 | −0.61 ± 0.16 | −0.67 ± 0.15 |
| 0.25% DHEA | −0.70 ± 0.17 | −1.11 ± 0.16 | −1.19 ± 0.16 | −1.27 ± 0.16 |
| 0.50% DHEA | −0.98 ± 0.15 | −1.36 ± 0.15 | −1.37 ± 0.17 | −1.56 ± 0.15 |
| 1.0% DHEA | −1.00 ± 0.15 | −1.29 ± 0.14 | −1.38 ± 0.17 | −1.37 ± 0.14 |

*mean ± SEM

TABLE 9

Change from day 1 in the most bothersome symptoms at 12 weeks of treatment with 0% (placebo), 0.25%, 0.50% and 1.0% DHEA. Change from one category (Severe → moderate → mild → none) was taken as −1 while a change of 2 categories was −2, etc . . .

| | Category change | | | | |
|---|---|---|---|---|---|
| | −3 | −2 | −1 | 0 | +1 |
| Doses | | | % women | | |
| 0.0% DHEA | 4.65 | 16.3 | 25.6 | 48.8 | 4.65 |
| 0.25% DHEA | 7.50 | 42.5 | 22.5 | 25.0 | 2.50 |
| 0.50% DHEA | 20.0 | 33.3 | 28.9 | 17.8 | 0.0 |
| 1.0% DHEA | 10.9 | 37.0 | 32.6 | 17.4 | 2.17 |

PHARMACEUTICAL COMPOSITION EXAMPLES

Set forth below, by way of example and not of limitation, are several pharmaceutical compositions utilizing preferred active sex steroid precursor DHEA. The concentration of active ingredient may be varied over a wide range as discussed herein. The amounts and types of other ingredients that may be included are well known in the art.

Example A

Vaginal or Oral Tablet

| Ingredient | Weight % (by weight of total composition) |
|---|---|
| DHEA | 5.0 |
| Gelatin | 6.5 |
| Lactose | 70.5 |
| Starch | 18.0 |

Example B 1.3 ml Vaginal Suppository

| Ingredient | Weight % (by weight of total composition) |
|---|---|
| DHEA | 0.50 |
| Whitepsol H-15 base | 99.50 |

DHEA suppositories were prepared using Whitepsol H-15 base (available from Medisca, Montreal, Canada). Any other lipophilic base such as but non limited to butter, cocoa butter, Cotomar, Dehydag Base, Fattibase, Hexaride Base 95, Hydrokote, Suppocire, Wecobee, theobroma oil, Japocire, Ovucire, Massa Estarinum or other combinations of the foregoing could used.

Example C

Vaginal or Topical Cream

| Ingredient | Weight % (by weight of total composition) |
|---|---|
| DHEA | 1.0 |
| Emulsifying Wax, NF | 18.0 |
| Light mineral oil, NF | 12.0 |
| Benzyl alcohol | 1.0 |
| Ethanol 95% USP | 34.0 |
| Purifed water, USP | 34.0 |

Vaginal or Oral Gelatin Capsule

Other sex steroid precursors may be substituted for DHEA in the above formulations. More than one precursor may be included in which case the combined weight percentage is preferably that of the weight percentage for the single precursor given in the examples above.

The invention has been described in terms of preferred embodiments and examples, but is not limited thereby. Those of skill in the art will readily recognize the broader applicability and scope of the invention which is limited only by the patent claims herein.

What is claimed is:

1. A method of treating or reducing the likelihood of acquiring a condition selected from the group consisting of vaginal atrophy, atrophic vaginitis, vaginal dryness, dyspareunia and sexual dysfunction in postmenopausal women comprising administering, to a human female in need of such treatment or reduction, a sex steroid precursor selected from the group consisting of dehydroepiandrosterone, dehydroepiandrosterone-sulfate, androst-5-ene-3β,17β-diol, and 4-androstene-3,17-dione, wherein said sex steroid precursor is administered intravaginally at a therapeutic amount of 13 mg per day or less.

2. The method of claim 1 wherein said therapeutic amount does not increase the level of circulating androgen metabolites and does not increase the circulating levels of estradiol above the values found in normal postmenopausal women in order to avoid the risk of breast and uterine cancer with increased circulating estrogens.

3. The method of claim 2 wherein the average 24 hour level of circulating estradiol is below 10 pg/mL.

4. The method of claim 1 wherein the therapeutic amount of sex steroid precursor is 3 to 13 mg per day.

5. The method of claim 2 wherein the therapeutic amount of sex steroid precursor is 3 to 13 mg per day.

6. The method of claim 3 wherein the therapeutic amount of sex steroid precursor is 3 to 13 mg per day.

7. The method of claim 1 wherein the therapeutic amount of sex steroid precursor is 6.5 mg per day or less.

8. The method of claim 2 wherein the therapeutic amount of sex steroid precursor is 6.5 mg per day or less.

9. The method of claim 3 wherein the therapeutic amount of sex steroid precursor is 6.5 mg per day or less.

10. The method of claim 1 wherein the therapeutic amount of sex steroid precursor is 3.25 per day or less.

11. The method of claim 2 wherein the therapeutic amount of sex steroid precursor is 3.25 per day or less.

12. The method of claim 3 wherein the therapeutic amount of sex steroid precursor is 3.25 per day or less.

13. The method of claim 1 wherein the sex steroid precursor is dehydroepiandrosterone.

14. The method of claim 2 wherein the sex steroid precursor is dehydroepiandrosterone.

15. The method of claim 3 wherein the sex steroid precursor is dehydroepiandrosterone.

16. The method of claim 4 wherein the sex steroid precursor is dehydroepiandrosterone.

17. The method of claim 5 wherein the sex steroid precursor is dehydroepiandrosterone.

18. The method of claim 6 wherein the sex steroid precursor is dehydroepiandrosterone.

19. The method of claim 7 wherein the sex steroid precursor is dehydroepiandrosterone.

20. The method of claim 8 wherein the sex steroid precursor is dehydroepiandrosterone.

21. The method of claim 9 wherein the sex steroid precursor is dehydroepiandrosterone.

22. The method of claim 10 wherein the sex steroid precursor is dehydroepiandrosterone.

23. The method of claim 11 wherein the sex steroid precursor is dehydroepiandrosterone.

24. The method of claim 12 wherein the sex steroid precursor is dehydroepiandrosterone.

25. The method of claim 1 wherein the sex steroid precursor is administered by means of an intravaginal formulation selected from the group consisting of cream, lotion, gel, ointment, ovule, suppository and ring.

26. The method of claim 25 wherein the formulation is a vaginal suppository.

27. A method of treating a condition selected from the group consisting of vaginal atrophy, atrophic vaginitis, vaginal dryness, dyspareunia and sexual dysfunction in postmenopausal women comprising administering, to a human female in need of such treatment, a vaginal suppository comprising 13 mg or less of dehydroepiandrosterone.

28. A method of treating a condition selected from the group consisting of vaginal atrophy, atrophic vaginitis, vaginal dryness, dyspareunia and sexual dysfunction in postmenopausal women comprising administering, to a human female in need of such treatment, a vaginal suppository comprising 3-13 mg of dehydroepiandrosterone.

* * * * *